United States Patent
Ho

(10) Patent No.: US 9,375,493 B2
(45) Date of Patent: Jun. 28, 2016

(54) BACTERIAL IMAGING AGENTS AND METHODS OF USING SAME

(71) Applicant: VisEn Medical, Inc., Waltham, MA (US)

(72) Inventor: Guojie Ho, Sudbury, MA (US)

(73) Assignee: VisEn Medical, Inc., Waltham, MA (US)

( * ) Notice: Subject to any disclaimer, the term of this patent is extended or adjusted under 35 U.S.C. 154(b) by 0 days.

(21) Appl. No.: 13/837,323

(22) Filed: Mar. 15, 2013

(65) Prior Publication Data

US 2013/0309168 A1 Nov. 21, 2013

Related U.S. Application Data

(60) Provisional application No. 61/618,291, filed on Mar. 30, 2012.

(51) Int. Cl.
| | |
|---|---|
| *A61K 51/00* | (2006.01) |
| *A61M 36/14* | (2006.01) |
| *A61K 49/00* | (2006.01) |
| *C12Q 1/04* | (2006.01) |
| *G01N 33/534* | (2006.01) |
| *G01N 33/58* | (2006.01) |
| *C07C 53/10* | (2006.01) |
| *C07D 487/08* | (2006.01) |
| *G01N 21/64* | (2006.01) |

(52) U.S. Cl.
CPC ............. *A61K 49/0002* (2013.01); *C07C 53/10* (2013.01); *C07D 487/08* (2013.01); *C12Q 1/04* (2013.01); *G01N 21/6486* (2013.01); *G01N 33/534* (2013.01); *G01N 33/58* (2013.01); *A61K 49/0017* (2013.01)

(58) Field of Classification Search
None
See application file for complete search history.

(56) References Cited

U.S. PATENT DOCUMENTS

| | | |
|---|---|---|
| 4,647,447 A | 3/1987 | Gries et al. |
| 4,981,977 A | 1/1991 | Southwick et al. |
| 5,268,486 A | 12/1993 | Waggoner et al. |
| 5,486,616 A | 1/1996 | Waggoner et al. |
| 5,569,587 A | 10/1996 | Waggoner |
| 5,569,766 A | 10/1996 | Waggoner et al. |
| 5,593,658 A | 1/1997 | Bogdanov et al. |
| 5,627,027 A | 5/1997 | Waggoner |
| 5,808,044 A | 9/1998 | Brush et al. |
| 5,877,310 A | 3/1999 | Reddington et al. |
| 6,002,003 A | 12/1999 | Shen et al. |
| 6,004,536 A | 12/1999 | Leung et al. |
| 6,008,373 A | 12/1999 | Waggoner et al. |
| 6,043,025 A | 3/2000 | Minden et al. |
| 6,083,485 A | 7/2000 | Licha et al. |
| 6,083,486 A | 7/2000 | Weissleder et al. |
| 6,127,134 A | 10/2000 | Minden et al. |
| 6,130,094 A | 10/2000 | Waggoner et al. |
| 6,133,445 A | 10/2000 | Waggoner et al. |
| 6,136,612 A | 10/2000 | Ciana et al. |
| 6,258,340 B1 | 7/2001 | Licha et al. |
| 6,448,008 B1 | 9/2002 | Caputo et al. |
| 6,534,041 B1 | 3/2003 | Licha et al. |
| 6,592,847 B1 | 7/2003 | Weissleder et al. |
| 6,740,755 B2 | 5/2004 | Caputo et al. |
| 6,747,159 B2 | 6/2004 | Caputo et al. |
| 6,869,593 B2 | 3/2005 | Frangioni |
| 6,913,743 B2 | 7/2005 | Licha et al. |
| 6,926,885 B2 | 8/2005 | Licha et al. |
| 7,025,949 B2 | 4/2006 | Licha et al. |
| 7,374,746 B2 | 5/2008 | Frangioni |
| 7,445,767 B2 | 11/2008 | Licha et al. |
| 7,655,217 B2 | 2/2010 | Licha et al. |
| 7,833,737 B2 | 11/2010 | Supuran et al. |
| 7,947,256 B2 | 5/2011 | Rajopadhye et al. |
| 8,173,819 B2 | 5/2012 | Rajopadhye et al. |
| 8,221,721 B2 | 7/2012 | Narayanan |
| 8,420,055 B2 | 4/2013 | Gaw et al. |
| 8,455,651 B2 | 6/2013 | Rajopadhye et al. |
| 8,486,373 B2 | 7/2013 | Weissleder et al. |
| 8,685,370 B2 | 4/2014 | Rajopadhye et al. |
| 8,771,646 B2 | 7/2014 | Rajopadhye et al. |
| 8,815,214 B2 | 8/2014 | Rajopadhye et al. |
| 2005/0169843 A1 | 8/2005 | Weissleder et al. |
| 2008/0171351 A1 | 7/2008 | Smith |
| 2008/0226562 A1 | 9/2008 | Groves et al. |
| 2009/0068115 A1 | 3/2009 | Gaw et al. |
| 2009/0130024 A1 | 5/2009 | Narayanan et al. |
| 2009/0220430 A1 | 9/2009 | Rajopadhye et al. |
| 2010/0074847 A1 | 3/2010 | Madden et al. |
| 2010/0129293 A1 | 5/2010 | Licha et al. |
| 2010/0166659 A1 | 7/2010 | Licha et al. |

(Continued)

FOREIGN PATENT DOCUMENTS

| | | |
|---|---|---|
| EP | 1065250 | 1/2001 |
| WO | WO-97/40104 | 10/1997 |

(Continued)

OTHER PUBLICATIONS

Deligeorgiev et al. (Dyes and Pigments 2007, 75, 658-663).*
Ozmen et al. (2000) Infrared fluorescence sensing of submicromolar calcium: pushing the limits of photoinduced electron transfer, *Tetrahedron Letters* 41(47): 9185-9188.
Abel et al., "Preparation and investigation of antibacterial carbohydrate-based surfaces," *Carbohydrate Research*, vol. 337, pp. 2495-2499 (2002).

(Continued)

*Primary Examiner* — Michael G Hartley
*Assistant Examiner* — Melissa Perreira
(74) *Attorney, Agent, or Firm* — Goodwin Procter LLP

(57) ABSTRACT

The invention provides a family of agents that target bacterial infection, which can be used as imaging agents or therapeutic agents. The agents can be used to image sites of bacterial infection as well as other physiological processes in a subject.

18 Claims, 5 Drawing Sheets

(56) References Cited

U.S. PATENT DOCUMENTS

| | | |
|---|---|---|
| 2010/0172841 A1 | 7/2010 | Peterson et al. |
| 2010/0189657 A1 | 7/2010 | Weissleder et al. |
| 2010/0268070 A1 | 10/2010 | Jaffer et al. |
| 2011/0152501 A1 | 6/2011 | Weissleder et al. |
| 2011/0171136 A1 | 7/2011 | Poss et al. |
| 2011/0256065 A1 | 10/2011 | Frangioni |
| 2012/0321563 A1 | 12/2012 | Groves et al. |
| 2013/0137873 A1 | 5/2013 | Narayanan |
| 2013/0272967 A1 | 10/2013 | Rajopadhye et al. |
| 2014/0050662 A1 | 2/2014 | Ho |

FOREIGN PATENT DOCUMENTS

| | | |
|---|---|---|
| WO | WO-99/51702 | 10/1999 |
| WO | WO-01/21624 | 3/2001 |
| WO | WO-2006/137092 | 12/2006 |
| WO | WO-2008/124703 | 10/2008 |
| WO | WO-2010/065906 | 6/2010 |
| WO | WO-2010/147666 | 12/2010 |

OTHER PUBLICATIONS

Anaya et al., "Detection and identification of bacterial cell surface proteins by fluorescent labeling," *Proteomics*, vol. 7, pp. 215-219 (2007).

Cohen et al., "Polycations. 15. Polyammonium Surfaces—A New Approach to Antifungal Activity," *Letters in Drug Design and Discovery*, vol. 1, pp. 88-90 (2004).

Fabian et al., "Polycations: Syntheses of Polyammonium Strings as Antibacterial Agents," *Synlett*, pp. 1007-1009 (1997).

Hanshaw et al., "Fluorescent Detection of Apoptotic Cells by Using Zinc Coordination Complexes with a Selective Affinity for Membrane Surfaces Enriched with Phosphatidylserine," *Chembiochem*, vol. 6, pp. 2214-2220 (2005).

Hoey et al., "Chemistry of X-Ray Contrast Media," *M. Sovak (ed.), Radiocontrast Agents*, pp. 23-125 (1984).

International Search Report and Written Opinion for International Application No. PCT/US2013/032126, mailed Aug. 8, 2013 (11 pages).

Jacques et al., "Comparison of Different Cationic Probes for Electron Microscopic Visualization of Bacterial Polyanionic Capsular Material," *Current Microbiology*, vol. 18, pp. 313-318 (1989).

Kurtaliev, "Spectral-luminescent and photochemical characteristics of homodimers of the styrylcyanine dye Sbt in solutions," *Spectrochimica Acta. Part A: Molecular and Biomolecular Spectroscopy*, vol. 81, pp. 449-457 (2011).

Leevy et al., "Noninvasive Optical Imaging of *Staphylococcus aureus* Bacterial Infection in Living Mice Using a Bis-Dipicolylamine-Zinc(II) Affinity Group Conjugated to a Near-Infrared Fluorophore," *Bioconjugate Chem*, vol. 19, pp. 686-692 (2008).

Ning et al., "Maltodextrin-based imaging probes detect bacteria in vivo with high sensitivity and specificity," *Nature Materials*, vol. 10, pp. 602-607 (2011).

Ratcliffe et al., "Synthesis and Properties of 2-(Naphthosultamyl)Methyl-Carbapenems with Potent Anti-MRSA Activity: Discovery of L-786,392," *Bioorganic & Medical Chemistry Letters*, vol. 9, pp. 679-684 (1999).

Smith et al., "Optical Imaging of Mammary and Prostate Tumors in Living Animals using a Synthetic Near Infrared Zinc(II)-Dipicolylamine Probe for Anionic Cell Surfaces," *J. Am. Chem. Soc.*, vol. 132, pp. 67-69 (2010).

Swanson et al., "Enhancement Agents for Ultrasound: Fundamentals," *Pharmaceuticals in Medical Imaging*, pp. 682-687 (1990).

Tiller et al., "Designing surfaces that kill bacteria on contact," *Proc. Natl. Acad. Sci. USA*, vol. 98, 5981-5985 (2001).

Tyler et al., "In Vivo Enhancement of Ultrasonic Image Luminance by Aqueous Solutions with High Speed of Sound," *Ultrasonic Imaging*, vol. 3, pp. 323-329 (1981).

Vasilev et al. "Synthesis of novel tetracationic asymmetric monomeric monomethine cyanine dyes—highly fluorescent dsDNA probes," *Coloration Technology*, vol. 127, pp. 69-74 (2010).

\* cited by examiner

BACTERIAL IMAGING AGENTS AND METHODS OF USING SAME

RELATED APPLICATIONS

This application claims the benefit of and priority to U.S. Provisional Patent Application No. 61/618,291, filed Mar. 30, 2012, the contents of which are hereby incorporated by reference.

FIELD OF THE INVENTION

The invention provides compositions and methods for detecting bacteria in a subject. The compositions generally contain a bacterial targeting moiety and an imaging reporter, which may be a fluorophore.

BACKGROUND

Current approaches for assessing molecular endpoints in certain diseases usually require tissue and blood sampling, surgery, and in the case of experimental animals, sacrifice at different time points. Despite improvements in non-invasive imaging, more sensitive and specific imaging agents and methods are needed. Imaging techniques capable of visualizing specific molecular targets and/or entire pathways would significantly enhance our ability to diagnose and assess treatment efficacy of therapeutic interventions for many different disease states. Most current imaging techniques report primarily on anatomical or physiological information (e.g., magnetic resonance imaging (MRI), computed tomography (CT), and ultrasound). Newer modalities such as optical imaging and new molecular imaging probes have the potential to revolutionize the way disease is detected, treated, and monitored.

The common paradigm for molecular imaging involves the use of a "molecular" probe or agent that selectively targets a particular gene, protein, receptor or a cellular function, with the absence, presence or level of the specific target being indicative of a particular disease state.

In particular, optical imaging offers several advantages that make it a powerful molecular imaging approach, both in the research and clinical settings. Specifically, optical imaging can be fast, safe, cost effective and highly sensitive. Scan times are on the order of seconds to minutes, there is no need for ionizing radiation, and the imaging systems can be relatively simple to use. In addition, optical probes can be designed as dynamic molecular imaging agents that may alter their reporting profiles in vivo to provide molecular and functional information in real time. In order to achieve maximum penetration and sensitivity in vivo, the choice for most optical imaging in biological systems is within the red and near-infrared (NIR) spectral region (600-900 nm), although other wavelengths in the visible region can also be used. In the NIR wavelength range, absorption by physiologically abundant absorbers such as hemoglobin or water, as well as tissue autofluorescence, is minimized.

Gram negative and gram-positive bacteria are the most common causes of infection such as peri-prosthetic, joint, bone, vascular prosthetic graft, inguinal, umbilical or incisional hernia mesh infections, and one of the challenging complications of surgery. Conventional diagnostic methods relying on the analysis of cultured bacteria recovered from suspected sites are time-consuming, insensitive, and not always feasible. Anatomic imaging techniques such as MRI and CT do not consistently distinguish infection from sterile inflammation and are therefore unreliable. More recently, the use of radiolabeled antibiotics and peptides directed to specific organisms has been studied, but clinical use has been limited, in part because of suboptimal specificity or sensitivity.

Early detection of bacterial infection is correlated with greater prognosis for full recovery. The unique cellular architecture of bacteria presents a number of different avenues for detecting and labeling bacteria at sites of infection. The cellular membrane, DNA and cell wall are three, well-studied bacterial structures. The cell surface of bacteria are highly negatively charged, more so than healthy mammalian cells. Positively-charged cationic probes can be used to selectively target and bind the anionic surfaces of bacterial cells over healthy mammalian cells.

Mammalian cells undergoing apoptosis, or programmed cell death, also express a much higher negative charge than normal cells. Positively charged cationic probes that target bacteria or bacterially compromised cells could also recognize and bind unhealthy, apoptotic mammalian cells as well.

Using such an approach, cationic molecules specific for anionic surfaces, such as those found in bacterial and apoptotic cells, can be linked to fluorescent molecules and used to probe for sites/areas of bacterial infection and/or apoptosis.

The ability to more accurately and efficiently detect and quantify sites of bacterial infection and apoptosis will aid in the understanding of biological phenomena such as pathogenesis, infection and cell death, as well as in the determination of the most appropriate treatment regimens.

SUMMARY OF THE INVENTION

The invention provides a novel class of fluorescent imaging agents that bind anionic surfaces on bacterial and apoptotic cells, and can be used in a variety of in vitro and in vivo applications, including but not limited to the identification of bacterial cells such as would be found in a microbial-based infection. Also provided are cationic agents/ligands that are fluorescent in the far-red or near-infrared region that are of particular utility for in vivo imaging of bacteria in live animals. In addition, provided are agents that, independently, contain a far-red or near-infrared fluorophore that has been modified by a plurality of chemical modifying groups that can be used for optimization of in vitro and in vivo properties of the agent.

In certain embodiments, the bacterium targeting agent includes: a bacterium targeting moiety comprising a positively charged moiety optionally substituted with an aliphatic, aromatic or hetero aromatic moiety; and an imaging reporter chemically linked, optionally through a linker (L) moiety, to the bacterium targeting moiety.

In certain embodiments, the positively charged moiety of the bacterium targeting agent is one of the following:

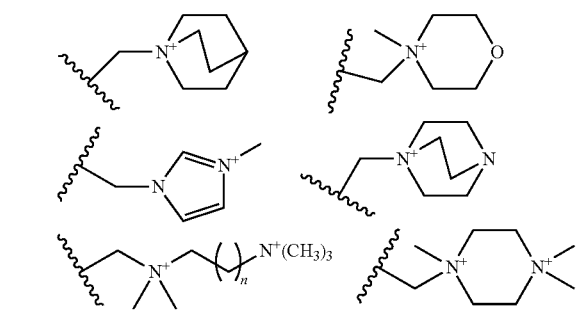

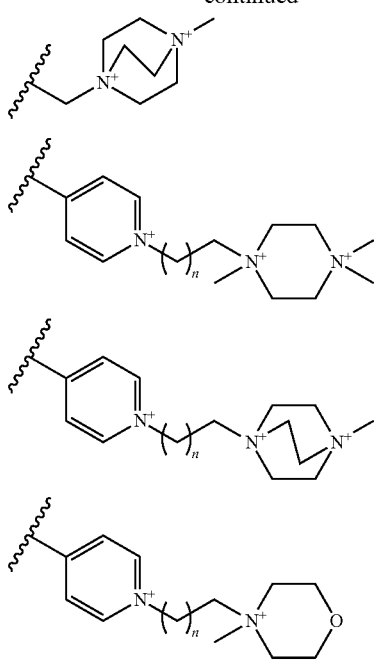

wherein n is 1, 2, 3, 4, 5, or 6.

In certain embodiments, the positively charged moiety is double-positively charged and represented by one of the following:

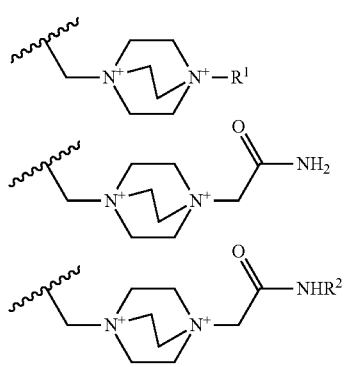

wherein $R^1$ and $R^2$ are, independently for each occurrence, substituted or unsubstituted aryl, $C_1$-$C_{18}$ alkyl, oligo- or polyethylene glycol. In certain embodiments, $R^1$ and $R^2$ are, independently for each occurrence substituted or unsubstituted heteroaryl.

In other embodiments, the bacterium targeting agent includes: a bacterium targeting moiety comprising a positively charged 1,4-diazabicyclo[2.2.2]octane (DABCO) moiety optionally substituted with an aliphatic, aromatic or heteroaromatic moiety; and an imaging reporter chemically linked, optionally through a linker (L) moiety to the bacterium targeting moiety.

In certain embodiments, the imaging reporter is selected from a group including: a fluorescent moiety, a magnetic moiety, and a radioisotope. Furthermore, the imaging reporter bears a plurality of chemical modifying moieties.

Another aspect of the invention provides a compound of formula (I):

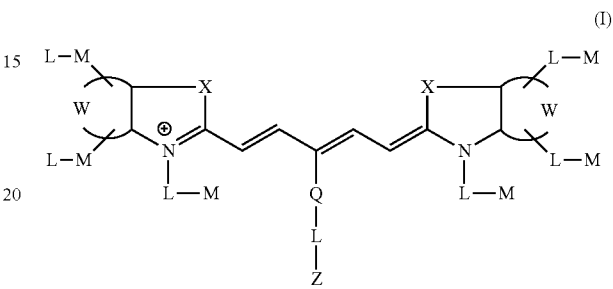

or a salt thereof, wherein the variables are as defined in the detailed description.

Another aspect of the invention provides a compound of formula (II):

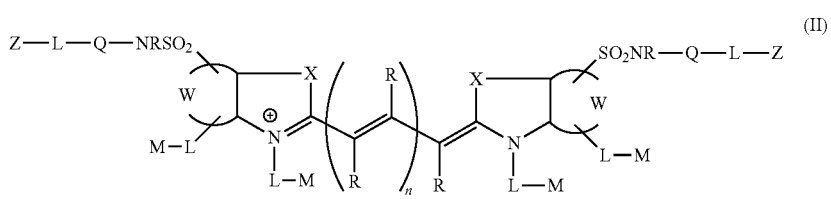

or a salt thereof, wherein the variables are as defined in the detailed description.

Another aspect of the invention provides a compound of formula (III):

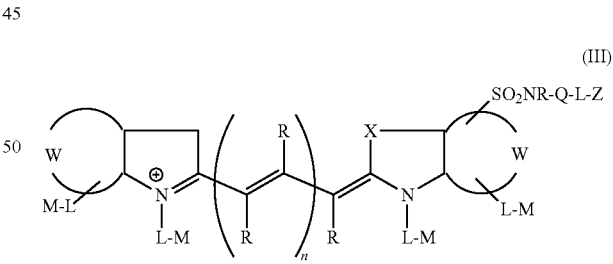

or a salt thereof, wherein the variables are as defined in the detailed description.

In certain embodiments, the bacterial targeting agent (such as a compound of Formula I, II, or III) is fluorescent in the far-red or near-infrared wavelengths.

Another aspect of the invention provides a compound of formula (IV):

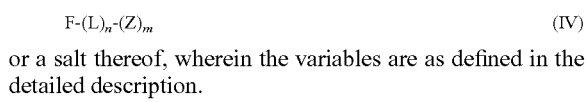

or a salt thereof, wherein the variables are as defined in the detailed description.

In certain embodiments, the chemical modifying moiety (M) is selected from the group consisting of a hydrogen, alcohol, sulfonate, polysulfonate, cysteic acid, sulfonamide, sulfoxide, sulfone, carboxylate, ketone, phosphonate, phosphate; iminodiacetate, ethylenediamine tetraacetic acid, diethylenetriamine pentaacetic acid, tetraazacyclododecane tetraacetic acid, an amino acid or polyamino acid, oligo- or polyethylene glycol, amine, quaternary ammonium ion, sugars, glucosamine, galactosamine, mannosamine, polyethylene glycol (PEG) and derivatives thereof, for example, alkoxy polyethylene glycol (for example, methoxypolyethylene glycol, ethoxypolyethylene glycol and the like), branched polypropylene glycol, polypropylene glycol, a graft copolymer of poly-lysine and methoxypolyethyleneglycol, peptides, lipids, fatty acids, palmitate, phospholipids, phospholipid-PEG conjugates, carbohydrates (such as dextran, amino-dextran, carboxymethyl-dextran), iron oxide nanoparticles, naphthylalanine, phenylalanine, 3,3-diphenylpropylamine, taurine, phosphonates, phosphates, carboxylates and polycarboxylates. In other embodiments, the chemical modifier(s) M reduce the nonspecific cell membrane permeability of the agent. In other embodiments, the chemical modifier(s) M reduce the nonspecific tissue accumulation of the agent when administered to a live animal.

In certain embodiments, the bond or linker moiety (L) comprises a diradical of a moiety selected from the group consisting of glycine, alanine, β-alanine, —NH—$(CH_2)_n$—C(=O)— where n=1-8,4-aminomethylbenzoic acid, cysteic acid, glutamic acid, amino-polyethylene glycol-carboxylic acid, amino-polyethylene glycol amine, ethylenediamine, propylenediamine, spermidine, spermine, hexanediamine, and diamine-amino acids, such as homolysine, lysine, ornithine, diaminobutyric acid and diaminopropionic acid, succinic acid, glutaric acid, suberic acid, adipic acid, amide, triazole, urea, or thiourea.

Additional exemplary bacterium targeting agents include compounds embraced by Formula V, VI, and VII described in the detailed description.

Another aspect of the invention provides a pharmaceutically acceptable composition suitable for administration to a subject including a compound described herein (such as a bacterium imaging agent) and a pharmaceutically acceptable excipient.

Another aspect of the invention provides a method of in vivo imaging, the method including: (a) administering to a subject an agent described here (such as a bacterium imaging agent); (b) allowing the agent to distribute within the subject; and (c) detecting a signal emitted by the agent.

Another aspect of the invention provides a method of in vivo optical imaging, the method including: (a) administering to a subject an agent described herein (such as a bacterium imaging agent), wherein the agent comprises a fluorochrome; (b) allowing the agent to distribute within the subject; (c) exposing the subject to light of a wavelength absorbable by the fluorochrome; and (d) detecting a signal emitted by the agent.

Another aspect of the invention provides a method of in vivo imaging, wherein the signal emitted by the agent is used to construct an image. In certain embodiments, the image is a tomographic image. In certain embodiments, the invention provides a method of in vivo optical imaging, wherein steps (a)-(c) are repeated at predetermined time intervals thereby to permit evaluation of the emitted signals of the agent (such as a bacterium imaging agent) in the subject over time. In certain embodiments, the invention provides a method of in vivo optical imaging, wherein steps (a)-(d) are repeated at predetermined time intervals thereby to permit evaluation of the emitted signals of the agents (such as a bacterium imaging agents) in the subject over time. In certain embodiments, the invention provides a method of in vivo imaging, wherein the subject is an animal or a human. In certain embodiments, the invention provides a method of in vivo imaging, wherein in step (a) two or more imaging probes whose signal properties are distinguishable from one another are administered to a subject, wherein at least one of the imaging probes is an agent described herein (such as a bacterium imaging agent). In certain embodiments, the invention provides a method of in vivo optical imaging, wherein the illuminating and detecting steps are performed using an endoscope, catheter, tomographic system, hand-held optical imaging system, or an intraoperative microscope. In certain embodiments, the invention provides a method of in vivo imaging, wherein the presence, absence, or level of emitted signal is indicative of a disease state. In certain embodiments, the invention provides a method of in vivo imaging, wherein the method is used to detect and/or monitor a disease. In certain embodiments, the disease is selected from the group consisting of bone disease, cancer, cardiovascular disease, environmental disease, dermatological disease, immunologic disease, inherited disease, infectious disease, inflammatory disease, metabolic disease, ophthalmic disease, and respiratory disease.

Another aspect of the invention provides a method of in vivo imaging, wherein, in step (a), cells labeled with an agent described herein (such as a bacterium imaging agent) are administered to the subject. In other embodiments, the signal emitted by the agent (such as a bacterium imaging agent) is used to monitor trafficking and localization of the cells.

Another aspect of the invention provides a method of imaging bacterium infection in a subject, the method comprising the steps of: (a) administering an agent to a subject; and (b) detecting the presence of the agent thereby to produce an image representative of bacterium infection. In certain embodiments, the invention provides a method of treating a disease in a subject comprising administering to a subject, either systemically or locally, an agent, wherein the agent comprises a radiolabel that localizes in the disease area and delivers an effective dose of radiation.

Another aspect of the invention provides an in vitro imaging method, the method comprising: (a) contacting a sample with an agent; (b) allowing the agent to bind to a biological target; (c) optionally removing unbound agent; and (d) detecting signal emitted from the agent thereby to determine whether the agent has been activated by or bound to the biological target. In other embodiments, the sample is a biological sample.

Compounds described herein are efficacious for the binding of anionic surfaces, especially cell membranes of bacteria, as well as for in vitro and in vivo fluorescence imaging of bacteria and therefore can be used for both therapeutic and diagnostic applications.

Another aspect of the invention provides methods for in vitro and in vivo imaging using the fluorescent bacterium imaging agents. With respect to optical in vivo imaging, the method comprises (a) administering to a subject bacterium targeting agents of the invention; (b) allowing the bacterium targeting agents to distribute within the subject; (c) exposing the subject to light of a wavelength absorbable by the fluorophore of the bacterium targeting agent; and (d) detecting an optical signal emitted by the bacterium targeting agent. The signal emitted by the agent can be used to construct an image. In certain embodiments, certain of the images are a tomographic image. Furthermore, it is understood that the foregoing steps can be repeated at predetermined intervals thereby permitting evaluation of the subject over time.

The bacterium targeting agents can be formulated into a pharmaceutical composition suitable for administration to a subject, for example, an animal and/or a human subject. The pharmaceutical composition can include one or more of the bacterium targeting agents and one or more stabilizers in a physiologically acceptable carrier.

The subject may be a vertebrate, for example, a mammal, for example, a human. The subject may also be a non-vertebrate (for example, C. elegans, drosophila, or another model research organism, etc.) used in laboratory research.

The bacterium targeting agent, can include, for example, one to five bacterium targeting binding moieties (for example, from two to five, three to five, or four to five bacterium targeting binding moieties), each chemically linked to the imaging reporter. The agents can comprise a plurality of bacterium targeting moieties each chemically linked to the imaging reporter.

Imaging reporters can be chosen, for example, from a fluorophore reporter, a fluorochrome reporter, an optical reporter, a magnetic reporter, a radiolabel, an X-ray reporter, an ultrasound imaging reporter, a nanoparticle-based reporter, or combination thereof. The bacterium imaging agent can further comprise a biological modifier chemically linked to the bacterium targeting moiety or to the imaging reporter.

In addition, another aspect of the invention provides methods for in vitro and in vivo imaging using the bacterium targeting agents. With respect to optical in vivo imaging, one exemplary method comprises (a) administering to a subject one or more of the foregoing bacterium targeting agents of the technology described here, wherein the agents comprise one or more fluorochromes; (b) allowing the agent to distribute within the subject; (c) exposing the subject to light of a wavelength absorbable at least one fluorochrome; and (d) detecting a signal emitted by the bacterium targeting agent. The signal emitted by the agent can be used to construct an image, for example, a tomographic image. Furthermore, it is understood that the foregoing steps can be repeated at predetermined intervals, which permit evaluation of the subject over time.

The bacterium targeting agents can be used to measure bacterial cell numbers (bacterial infection) or other physiological processes such as cell death in a subject. One exemplary method comprises (a) administering one or more of the foregoing bacterium targeting agents to a subject; (b) detecting the presence of the agent(s) thereby to produce an image representative of sites of bacterial infection within the subject.

In each of the foregoing methods, the subject can be a vertebrate, for example, a mammal, for example, a human. The subject also can be a non-vertebrate (for example, C. elegans, drosophila, or another model research organism, etc.) used in laboratory research.

In addition, the bacterium targeting agents can be incorporated into a kit, for example, a kit with optional instructions for using the bacterium targeting agents in in vivo or in vitro imaging methods. The kit optionally can include components that aid in the use of the bacterium targeting agents, for example, buffers, and other formulating agents. Alternatively, the kit can include medical devices that aid in the administration and/or detection of the bacterium targeting agents to subjects.

Other features and advantages of the invention will be apparent from the following figures, detailed description, and the claims.

BRIEF DESCRIPTION OF THE DRAWINGS

FIG. 1 depicts in vitro binding studies between a bacterium targeting agent (compound A7) and the bacterial species Escherichia coli and Staphylococcus epidermidis.

FIG. 2 depicts tomographic images and total fluorescence for sites of S. epidermidis bacterial infection detected in mice using a bacterium targeting agent (compound A7).

FIG. 3 depicts tomographic images of mice one, two, and three hours post-infection.

DETAILED DESCRIPTION

Figure 1A:
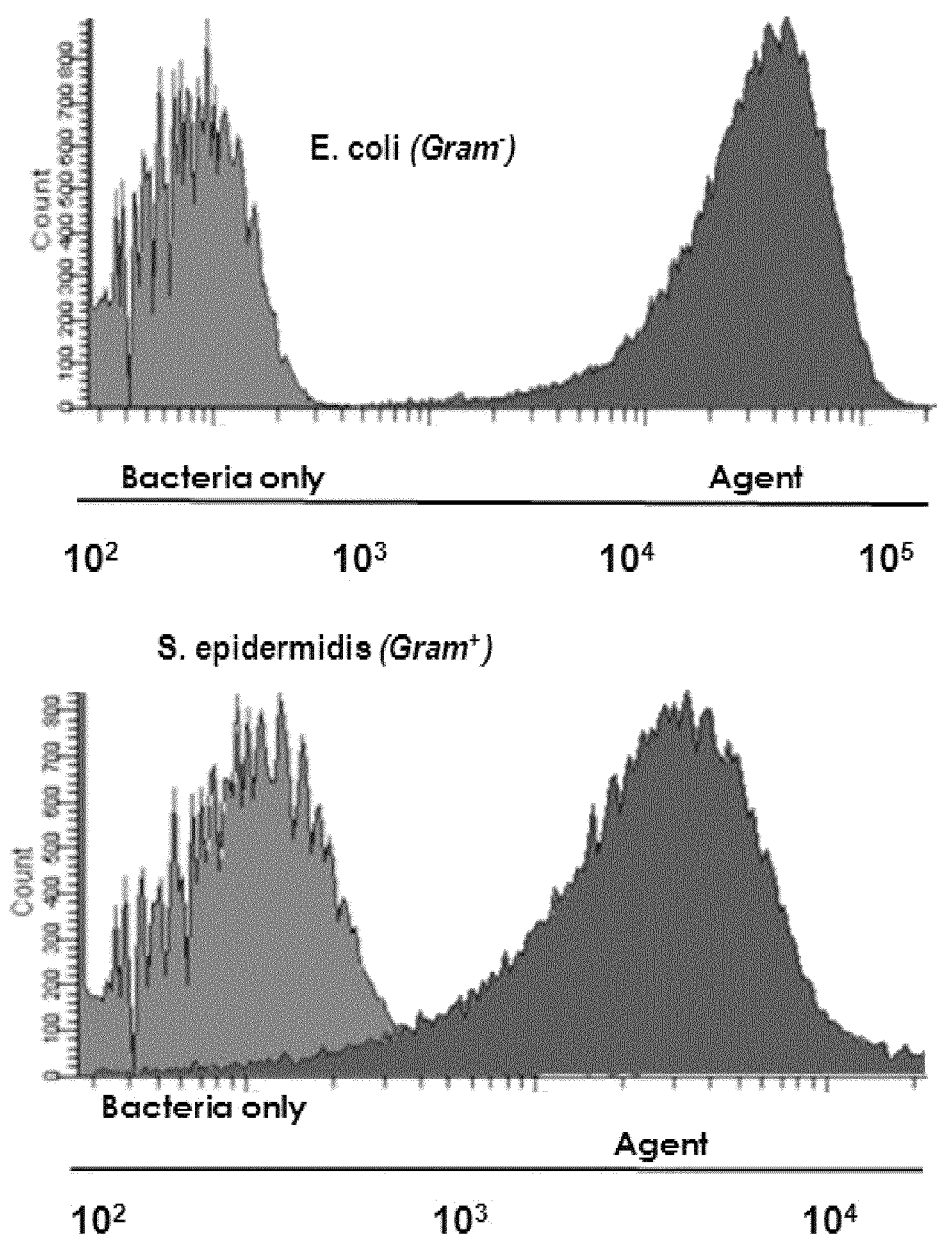
FIG. 1A is a series of scatter plots comparing bacteria unbound and bound to a bacterium targeting agent using flow cytometry.

The invention provides compositions and methods for detecting bacteria in a subject. Technology described herein is based, in part, upon the discovery that it is possible to produce fluorescent bacterium targeting agents that are stable, biocompatible, exhibit low nonspecific cellular uptake in vitro and low nonspecific tissue uptake in vivo, and can be used in a variety of in vitro and in vivo assays and imaging applications, as well as in a variety of therapeutic applications. Various aspects of the bacterial targeting agents and their use are described in the sections below. Aspects of the invention described in one particular section are not to be limited to any particular section. Further, if a variable is not accompanied by a definition, then the previous definition of the variable controls.

I. Bacterial Targeting Agents

One aspect of the invention provides bacterial targeting agents. The bacterial targeting agents generally comprise (i) a bacterial targeting moiety and (ii) an imaging reporter, which may be a fluorophore. The bacterial targeting moiety may be connected to the imaging reporter via a linker, as represented by the following formula:

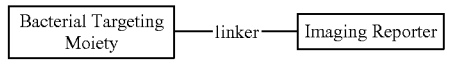

Properties of the bacterial targeting agent may be adjusted by selecting particular types of imaging reporter moieties, linker, and bacterial targeting agent. In addition, properties of the bacterial targeting agent can be adjusted by attaching one or more chemical modifying groups (M). The bacterial targeting moiety, linker, imaging reporter, and chemical modifying moieties are described in more detail in the sub-sections below.

The "imaging reporter" or "IR" can be any suitable chemical or substance which is used to provide the contrast or signal in imaging and that is detectable by imaging techniques. In certain embodiments, the imaging reporter comprises one or more fluorophores, photoluminescent nanoparticles, radioisotopes, superparamagnetic agents, X-ray contrast agents, and ultrasound agents. It is understood that the IR can also comprise a therapeutic reporter such as a porphyrin used in photodynamic therapy and radionuclide used in radiotherapy.

The term "chemical modifying group" or "M" is understood to mean any moiety that can be used to alter the physical, chemical or biological properties of the bacterium targeting agent, such as, without limitations, making it more water soluble or more dispersible in media for administration, increasing binding specificity, increasing or decreasing net molecular charge, decreasing immunogenicity or toxicity, or modifying cell uptake, pharmacokinetic or biodistribution profiles compared to the non-M modified bacterium targeting agents.

Additional information relating to bacterial targeting agents can be found in, for example, U.S. Pat. No. 7,833,737; and International Application Publication Nos. WO2006/137092, WO2008/124703, WO 2010/147666, and WO2010/065906, all of which are incorporated herein by reference in their entirety.

A. Bacterium Targeting Moiety

The bacterial targeting moiety is generally an organic functional group containing at least one ammonium group. Exemplary bacterial modifying moieties include (i) a substituted heterocyclyl containing one quaternary ring nitrogen atom, (ii) a substituted heterocyclyl containing two quaternary ring nitrogen atoms, and (iii) an ammonium substituted heteroalkyl group. In certain embodiments, the bacterium targeting moiety is one of the following:

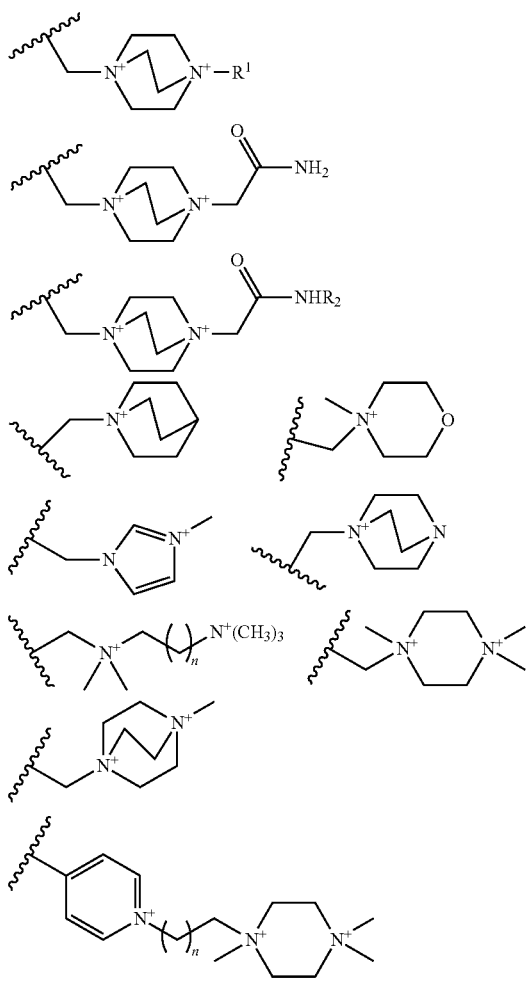

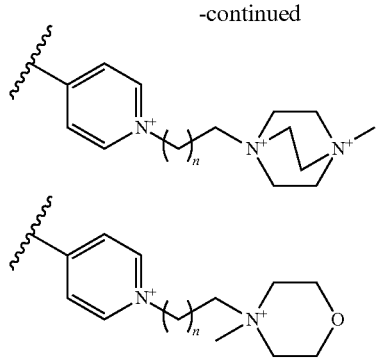

wherein $R^1$ is alkyl, and $R^2$ is alkyl or -alkylene-C(O)N($R^3$)$_2$, wherein $R^3$ represents independently for each occurrence hydrogen, alkyl, or two occurrences of $R^3$ are taken together with the nitrogen to which they are attached to form a heterocycle.

In certain other embodiments, the bacterium targeting moiety is one of the following: (a) substituted heterocyclyl containing one quaternary ring nitrogen atom, such as an alkyl-substituted piperazine or alkyl-substituted DABCO, (b) substituted heterocyclyl containing two quaternary ring nitrogen atoms, such as an alkyl-substituted piperazine or alkyl-substituted DABCO, or (c)

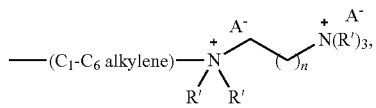

wherein R' represents independently for each occurrence alkyl or hydrogen; n is 1, 2, 3, or 4; and A represents independently for each occurrence an anion, such as alkyl-$CO_2^-$.

Additional exemplary bacterium targeting moieties contemplated to be amenable for use in the present invention include those described in, for example, U.S. Pat. Nos. 7,833,737; and International Application Publication Nos. WO2006/137092, WO2008/124703, WO2010/147666, and WO2010/065906, all of which are incorporated herein by reference in their entirety.

B. Imaging Reporters

A variety of imaging reporters, for example, fluorescent and non-fluorescent reporters are contemplated to be amenable for use in the present invention. Exemplary imaging reporters are described below, including imaging reporters that have a fluorescent moiety, a magnetic moiety, or a radioisotope. The imaging reporter may be substituted with a plurality of chemical modifying moieties.

(a) Fluorescent Reporters

In certain embodiments, the imaging reporter is a fluorophore molecule. A "fluorophore" includes, but is not limited to, a fluorochrome, a fluorochrome quencher molecule, any organic or inorganic dye, metal chelate, or any fluorescent enzyme substrate, including protease activatable enzyme substrates.

In certain embodiments, the bacterium targeting agents comprise a fluorophore. In certain embodiments, the fluorophores are far red and near infrared fluorochromes (NIRFs)

with absorption and emission maximum between about 600 and about 1200 nm, more preferably between about 600 nm and about 900 nm. It will be appreciated that the use of fluorochromes with excitation and emission wavelengths in other spectrums can also be employed in the compositions and methods of the present invention. Exemplary fluorochromes include but are not limited to a carbocyanine fluorochrome and an indocyanine fluorochrome.

The near infrared fluorochromes preferably have an extinction coefficient of at least 50,000 $M^{-1}cm^{-1}$ per fluorochrome molecule in aqueous medium. The near infrared fluorochromes preferably also have (1) high quantum yield (i.e., quantum yield greater than 5% in aqueous medium), (2) narrow excitation/emission spectrum, spectrally separated absorption and emission spectra (i.e., excitation and emission maxima separated by at least 15 nm), (3) high chemical and photostability, (4) non-toxicity, (5) good biocompatibility, biodegradability and excretability, and (6) commercial viability and scalable production for large quantities (i.e., gram and kilogram quantities) required for in vivo and human use.

Certain carbocyanine or polymethine fluorescent dyes can be used to produce the bacterium targeting agents of the invention and include, for example, those described in U.S. Pat. No. 6,747,159; U.S. Pat. No. 6,448,008; U.S. Pat. No. 6,136,612; U.S. Pat. Nos. 4,981,977; 5,268,486; U.S. Pat. No. 5,569,587; U.S. Pat. No. 5,569,766; U.S. Pat. No. 5,486,616; U.S. Pat. No. 5,627,027; U.S. Pat. No. 5,808,044; U.S. Pat. No. 5,877,310; U.S. Pat. No. 6,002,003; U.S. Pat. No. 6,004,536; U.S. Pat. No. 6,008,373; U.S. Pat. No. 6,043,025; U.S. Pat. No. 6,127,134; U.S. Pat. No. 6,130,094; U.S. Pat. No. 6,133,445; also WO 97/40104, WO 99/51702, WO 01/21624, and EP 1 065 250 A1; and Tetrahedron Letters 41, 9185-88 (2000).

Various fluorochromes are commercially available and can be used to construct the bacterium targeting agents of the invention. Exemplary fluorochromes include, for example, Cy5.5, Cy5 and Cy7 (GE Healthcare); AlexaFluor660, AlexaFluor680, AlexaFluor750, and AlexaFluor790 (Invitrogen); VivoTag680, VivoTag-5680, and VivoTag-5750 (V isEn Medical); Dy677, Dy682, Dy752 and Dy780 (Dyomics); DyLight547, DyLight647 (Pierce); HiLyte Fluor 647, HiLyte Fluor 680, and HiLyte Fluor 750 (AnaSpec); IRDye 800CW, IRDye 800RS, and IRDye 700DX (Li-Cor); and ADS780WS, ADS830WS, and ADS832WS (American Dye Source) and Kodak X-SIGHT 650, Kodak X-SIGHT 691, Kodak X-SIGHT 751 (Carestream Health).

Table 1 lists a number of exemplary commercial fluorochromes useful in the practice of the invention together with their spectral properties.

TABLE 1

| Fluorochrome | $\epsilon_{max}$ $M^{-1}$ $cm^{-1}$ | Absorbance max (nm) |
|---|---|---|
| Cy5 | 250,000 | 649 |
| Cy5.5 | 250,000 | 675 |
| Cy7 | 250,000 | 743 |
| AlexaFluor660 | 132,000 | 663 |
| AlexaFluor680 | 184,000 | 679 |
| AlexaFluor750 | 280,000 | 749 |
| VivoTag680 (VT680) | 100,000 | 670 |
| VivoTag-S680 | 220,000 | 674 |

TABLE 1-continued

| Fluorochrome | $\epsilon_{max}$ $M^{-1}$ $cm^{-1}$ | Absorbance max (nm) |
|---|---|---|
| VivoTag-S750 | 100,000 | 750 |
| Dy677 | 180,000 | 673 |
| Dy682 | 140,000 | 690 |
| Dy752 | 270,000 | 748 |
| Dy780 | 170,000 | 782 |
| DyLight547 | 150,000 | 557 |
| DyLight647 | 250,000 | 653 |
| IRDye800CW | 240,000 | 774 |
| IRDye800RS | 200,000 | 767 |
| IRDye700DX | 165,000 | 689 |
| ADS780WS | 170,000 | 782 |
| ADS830WS | 240,000 | 819 |
| ADS832WS | 190,000 | 824 |

In certain embodiments, the fluorophore is substituted by a plurality of chemical modifying groups. In certain embodiments, the fluorophore is represented by formula A:

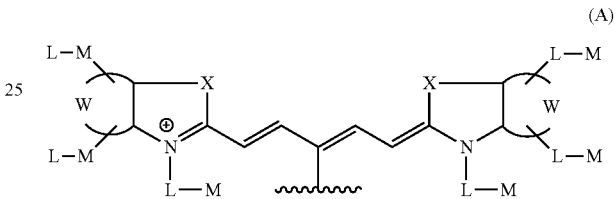

(A)

or a salt thereof, wherein:

W represents a benzo-condensed, a naphtho-condensed or a pyrido-condensed ring;

X, independently for each occurrence, is selected from the group consisting of $C(CH_2Y_1)(CH_2Y_2)$, O, S, and Se;

$Y_1$ and $Y_2$ are independently selected from the group consisting of hydrogen and $C_1$-$C_{20}$ aliphatic group optionally substituted with L-M;

L, independently for each occurrence, represents a bond or a linker moiety;

M, independently for each occurrence, represents a chemical modifying moiety; and ∼∼∼ represents a point of attachment of the fluorochrome to the linker or to the imaging reporter.

In one embodiment, the fluorochrome is represented by formula B:

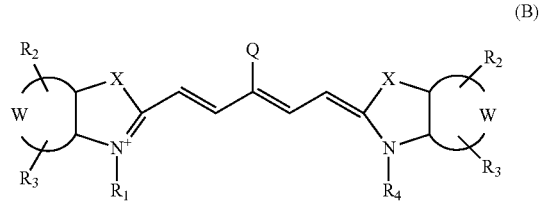

(B)

or a salt thereof, wherein:

X is independently selected from the group consisting of $C(CH_2Y_1)(CH_2Y_2)$, O, S, and Se;

$Y_1$ and $Y_2$ are independently selected from the group consisting of H, $C_1$-$C_{20}$ aliphatic group, and a $C_1$-$C_{20}$ aliphatic group substituted with —OR*, N(R*)$_2$ or —SR*;

W represents a benzo-condensed, a naphtho-condensed, or a pyrido-condensed ring;

R* is alkyl;

R$_1$ is selected from the group consisting of $(CH_2)_xCH_3$, $(CH_2)_1SO_3^-$ and $(CH_2)_1SO_3H$, wherein x is an integer selected from 0 to 6 and n is an integer selected from 2 to 6;

R$_4$ is selected from the group consisting of $(CH_2)_xCH_3$, $(CH_2)_1SO_3^-$ and $(CH_2)_1SO_3H$, wherein x is an integer selected from 0 to 6 and n is an integer selected from 2 to 6;

R$_2$ and R$_3$ are independently selected from the group consisting of H, carboxylate, carboxylic acid, carboxylic ester, amine, amide, sulfonamide, hydroxyl, alkoxyl, a sulphonic acid moiety and a sulphonate moiety;

Q is selected from the group consisting of a heteroaryl ring substituted with a carboxyl group and 6-membered heteroaryl ring substituted with a carbonyl group; or Q is selected from a group consisting of (i) a carboxyl functionalized heterocyclic ring, (ii) a carboxyl functionalized nitrogen containing heterocyclic ring, (iii) a carboxyl functionalized nitrogen containing 6-membered heterocyclic ring, such as pyridine, pyrimidone, pyrazine, or pyridazine, (iv) a carboxyl functionalized nitrogen containing 6-membered heterocyclic ring, such as pyridine, (v) a carbonyl functionalized nitrogen containing 6-membered heterocyclic ring, such as pyridine, (vi) an isonicotinic acid, nicotinic acid and picolinic acid, and a group selected from one of the following:

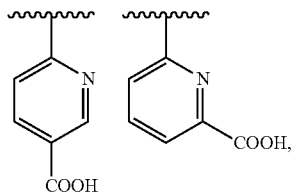

wherein, the carboxyl group is also in the form of an ester, an activated ester or carbonyl halide that is capable of reacting with nucleophiles, and can be, for example, a —C(O)—O-benzotriazolyl, —C(O)—O—(N-hydroxysuccinimidyl), —C(O)—O-tetrafluorophenyl, —C(O)—O-pentafluorophenyl, —C(O)—O-imidazole, and —C(O)—O-p-nitrophenyl.

A radical of a fluorochrome represented by formula B could be bonded to a linker or directly bonded to an imaging reporter. In certain embodiments, the radical of Formula B is where one or more variable R$_2$ groups are —S(O$_2$)N(alkyl)-.

In another embodiment, the fluorochrome is represented by Formula C:

or a salt thereof, wherein:

X$_1$ and X$_2$ are independently selected from the group consisting of $C(CH_2K_1)(CH_2K_2)$, O, S and Se;

K$_1$ and K$_2$ are independently H or C$_1$-C$_{20}$ aliphatic; or K$_1$ and K$_2$ together are part of a substituted or unsubstituted carbocyclic or heterocyclic ring;

Y$_1$ and Y$_2$ are each independently a benzo-condensed ring, a naphtha-condensed ring, or a pyrido-condensed ring;

n$_1$ is 1, 2, or 3;

R$_2$, R$_{11}$ and R$_{12}$ are independently H, halogen, alkyl, alkoxy, aryloxy, aryl, a sulfonate, an iminium ion, or any two adjacent R$_{12}$ and R$_{11}$ substituents, when taken in combination, form a 4-, 5-, or 6-membered carbocyclic ring optionally substituted one or more times by C$_1$-C$_6$ alkyl or halogen;

R$_1$ and R$_{13}$ are $(CH_2)_xCH_3$, when x is an integer selected from 0 to 6; or R$_1$ and R$_{13}$ are independently $(CH_2)_1SO_3^-$ or $(CH_2)_nSO_3H$ when n is an integer selected from 2 to 6;

R$_3$, R$_4$ and R$_5$ are independently selected from the group consisting of H, carboxylate, carboxylic acid, carboxylic ester, amine, amide, sulfonamide, hydroxyl, alkoxyl, a sulphonic acid moiety and a sulphonate moiety;

R$_6$ is unsubstituted C$_1$-C$_{20}$ aliphatic, unsubstituted aryl, or unsubstituted alkylaryl;

R$_7$ is H, unsubstituted C$_1$-C$_{20}$ aliphatic, unsubstituted aryl, or unsubstituted alkylaryl, wherein R$_7$ is optionally substituted with halogen; or R$_6$ and R$_7$, taken together form a 4-, 5-, 6- or 7-membered heterocyclic ring optionally substituted with halogen;

W is absent or is a group selected from the group consisting of —SO$_2$NR$_6$-Q-CHR$_7$—, —O—, —C(O)O—, and —C(O)N(H)—;

h=0-70; k=0 or 1; d=0-12; m=0-12; and p=0-12; and

~~~ represents a point of attachment of the fluorochrome to the linker or to the imaging reporter.

Some exemplary chemically modified fluorophores that can be used in the synthesis of the bacterium targeting agents of the invention include, for example, those listed in Table 2.

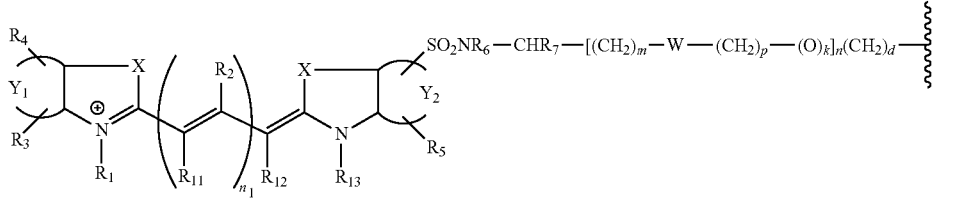

(C)

TABLE 2

| No. | Fluorophore |
|---|---|
| F1 | |
| F2 | |
| F3 | |
| F4 | |
| F5 | |
| F6 | |

TABLE 2-continued
| No. | Fluorophore |
|---|---|
| F7 | 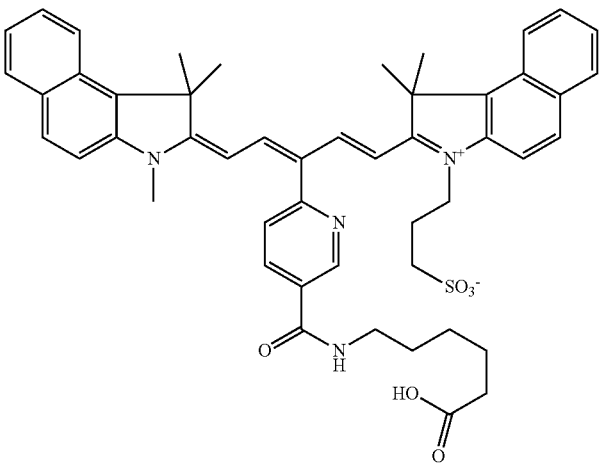 |
| F8 | 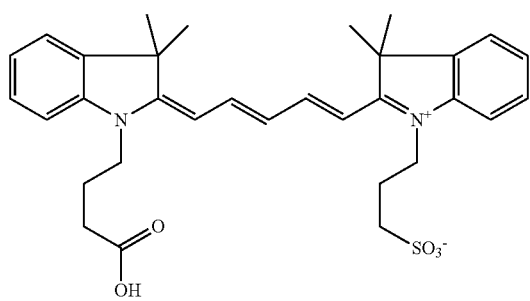 |
| F9 | 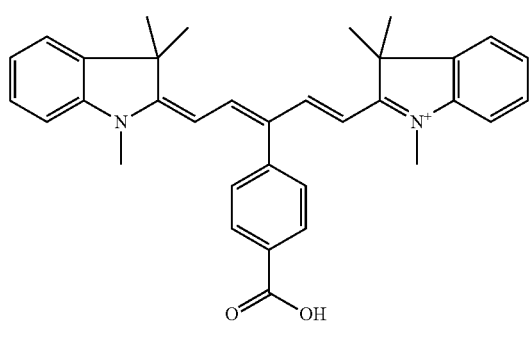 [SMILES: CN1/C(=C/C=C(/C=C/C2=[N+](C)c3ccccc3C2(C)C)c2ccc(C(=O)O)cc2)C(C)(C)c2ccccc21] |
| F10 | 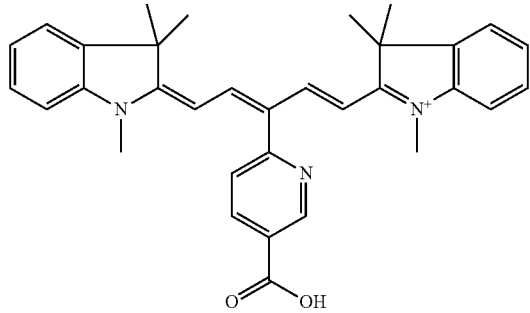 [SMILES: CN1/C(=C/C=C(/C=C/C2=[N+](C)c3ccccc3C2(C)C)c2ccc(C(=O)O)cn2)C(C)(C)c2ccccc21] |

TABLE 2-continued

| No. | Fluorophore |
|---|---|
| F11 | 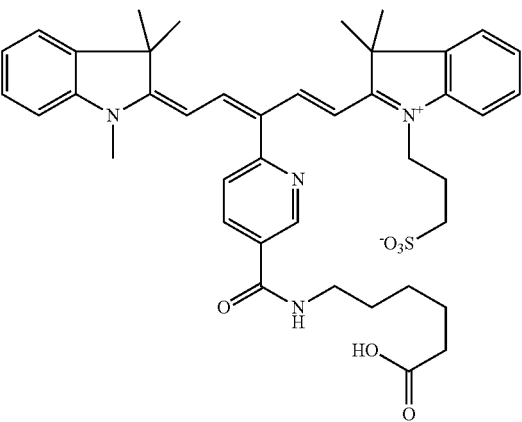 |
| F12 | 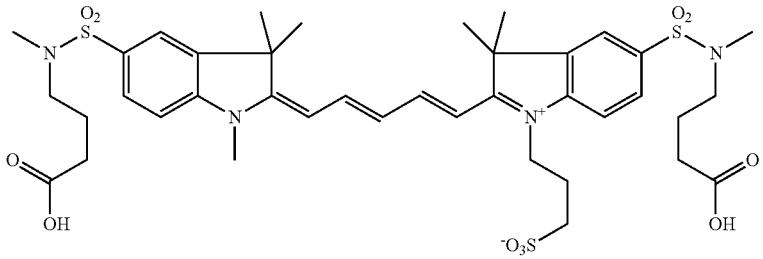 |
| F13 | 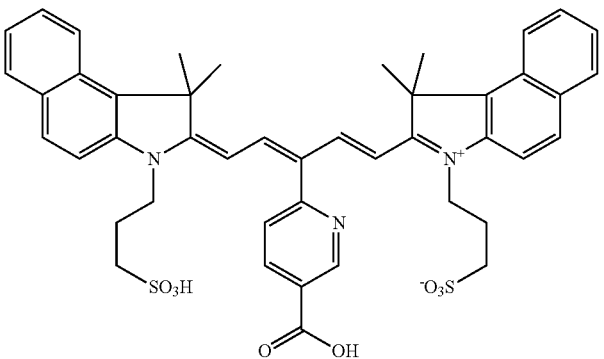 |
| F14 | 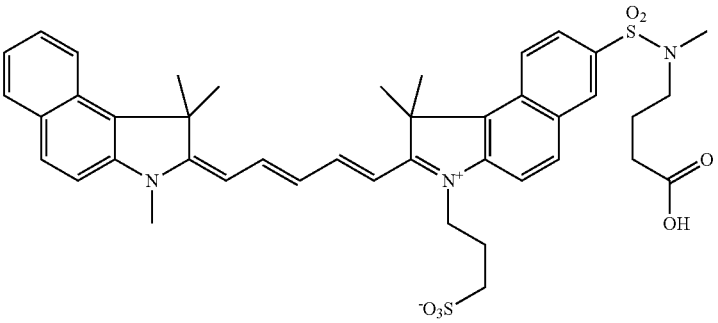 |

In certain embodiments, one or more fluorochrome molecules can be chemically linked to the bacterium targeting moiety to produce the fluorescent bacterium targeting agents.

In the case where the imaging reporter is a fluorochrome molecule, the extinction coefficient of the bacterium targeting agents can be calculated as the ratio of the absorbance of dye at its absorption maxima (for example at ~670 nm for VivoTag 680) in a 1 cm path length cell to the concentration of particles using the formula $\epsilon = A/cl$, where A is absorbance, c is molar concentration and l is path length in cm.

It is understood that the bacterium targeting agent can be linked to nanoparticles (for example, silicon containing nanoparticles) to produce fluorescent or luminescent nanoparticles. Aggregates of crystalline silicon (as multiple or single crystals of silicon), porous silicon, or amorphous silicon, or a combination of these forms, can form the nanoparticle. Preferred fluorescent silicon nanoparticles have a diameter between about 0.5 nm to about 25 nm, more preferably between about 2 nm and about 10 nm. The size of nanoparticles can be determined by laser light scattering or by atomic force microscopy or other suitable techniques.

Fluorescent silicon nanoparticles may have excitation and emission spectra 200 to 2000 nm, however, preferred fluorescent silicon nanoparticles have excitation and emission maximum between about 400 nm and about 1200 nm (and preferably 500 nm-900 nm, for example, 500 nm-600 nm, 600 nm-700 nm, 700 nm-800 nm, or 800 nm-900 nm). Preferred fluorescent silicon nanoparticles also have extinction coefficients of at least 50,000 $M^{-1}cm^{-1}$ in aqueous medium. Although fluorescent silicon nanoparticles that have excitation and emission maximum between 400 nm and 1200 nm are preferred, it will be appreciated that the use of fluorescent silicon nanoparticles with excitation and emission wavelengths in other spectrums can also be employed in the compositions and methods of the present invention. For example, in certain embodiments, the particles may have excitation approximately about 300-350 nm, and emission approximately about 400-450 nm.

Fluorescent silicon nanoparticles may also have the following properties: (1) high quantum yield (i.e., quantum yield greater than 5% in aqueous medium), (2) narrow emission spectrum (i.e., less than 75 nm; more preferably less than 50 nm), (3) spectrally separated absorption and emission spectra (i.e., separated by more than 20 nm; more preferably by more than 50 nm), (3) have high chemical stability and photostability (i.e., retain luminescent properties after exposure to light), (4) are biocompatible (see below) or can be made more biocompatible; (5) are non toxic or minimally toxic to cells or subjects at doses used for imaging protocols, (as measured for example, by $LD_{50}$ or irritation studies, or other similar methods known in the art) and/or (6) have commercial viability and scalable production for large quantities (i.e., gram and kilogram quantities) required for in vivo and human use.

Other exemplary fluorophores include metal oxide nanoparticles that are fluorescent and can be used in a variety of in vitro and vivo applications. In one embodiment, the bacterium targeting moieties are conjugated to fluorescent metal oxide nanoparticles with one or more of the following features: (1) a polymer coating suitable for attaching a plurality of fluorochromes thereby achieving large extinction coefficients (in excess of 1,000,000 $M^{-1}cm^{-1}$), (2) a non-crosslinked polymer coating suitable for attaching from about 10 to about 300 fluorochromes per particle, (3) a polymer coating suitable for attaching a plurality of fluorochromes in a manner that does not significantly compromise the quantum yield of the fluorochromes (e.g., the nanoparticles retain at least 50% of the fluorescent signal that is created by substantially the same number of free fluorochromes when tested under the same conditions), and (4) a polymer coating that is amenable to efficient chemical linking of biomolecules with retention of their biological properties to yield molecular imaging agents. The fluorescent metal oxide nanoparticles are highly stable molecular imaging agents in vitro, both before and after chemical linking of fluorochromes and bacterium targeting agents, but yet are labile and/or degradable in vivo.

The bacterium targeting moiety can be linked to fluorescent quantum dots such as amine T2MP EviTags (Evident Technologies) or Qdot Nanocrystals (Invitrogen). In general, fluorescent quantum dots are nanocrystals containing several atoms of a semiconductor material (including but not limited to those containing cadmium and selenium, sulfide, or tellurium; zinc sulfide, indium-antimony, lead selenide, gallium arsenide, and silica or ormosil, which have been coated with zinc sulfide to improve the properties of these fluorescent agents.

Furthermore, the bacterium targeting moiety can be conjugated to molecules capable of eliciting photodynamic therapy. These include, but are not limited to, Photofrin, Lutrin, Antrin, aminolevulinic acid, hypericin, benzoporphyrin derivative, and select porphyrins.

(b) Non-Fluorescent Reporters

The term "non-fluorescent reporter" as used herein, refers to a chemical moiety that is not fluorescent but which can be used to provide the contrast or signal in imaging and is detectable by a non-fluorescent imaging technique. In certain embodiments, other non-fluorescent reporters can be chemically linked with the imaging agents, or can be administered to a subject simultaneously or sequentially with the imaging agents of the invention. Such reporters can include photoluminescent nanoparticles, radioisotopes, superparamagnetic agents, X-ray contrast agents, and ultrasound agents. A reporter may also comprise therapeutic reporters such as porphyrins, Photofrin®, Lutrin®, Antrin®, aminolevulinic acid, hypericin, benzoporphryrin derivatives used in photodynamic therapy, and radionuclides used for radiotherapy.

(i) Radioactive Reporters

The agents can include one or more radioactive labels. Radioisotopic forms of metals such as copper, gallium, indium, technetium, yttrium, and lutetium can be chemically linked to the metallic imaging agents and can be used for nuclear imaging or therapeutic applications. Exemplary radioactive labels include, without limitation, $^{99m}Tc$, $^{111}In$, $^{64}Cu$, $^{67}Ga$, $^{186}Re$, $^{188}Re$, $^{153}Sm$, $^{177}Lu$, and $^{67}Cu$.

Other exemplary labels include, for example, $^{123}I$, $^{124}I$, $^{125}I$, $^{11}C$, $^{13}N$, $^{15}O$, and $^{18}F$. Other exemplary labels can be therapeutic radiopharmaceuticals including for example, $^{186}Re$, $^{188}Re$, $^{153}Sm$, $^{166}Ho$, $^{177}Lu$, $^{149}Pm$, $^{90}Y$, $^{212}Bi$, $^{103}Pd$, $^{109}Pd$, $^{159}Gd$, $^{140}La$, $^{198}Au$, $^{199}Au$, $^{169}Yb$, $^{175}Yb$, $^{165}Dy$, $^{166}Dy$, $^{67}Cu$, $^{105}Rh$, $^{111}Ag$, and $^{192}Ir$.

Chelators or bonding moieties for diagnostic and therapeutic radiopharmaceuticals are also contemplated and can be chemically associated with the imaging agents. Exemplary chelators can be selected to form stable complexes with radioisotopes that have imageable gamma ray or positron emissions, such as $^{99m}Tc$, $^{111}In$, $^{64}Cu$, and $^{67}Ga$. Exemplary chelators include diaminedithiols, monoamine-monoamidedithiols, triamide-monothiols, monoamine-diamide-monothiols, diaminedioximes, and hydrazines. Chelators generally are tetradentate with donor atoms selected from nitrogen, oxygen and sulfur, and may include for example, cyclic and acyclic polyaminocarboxylates such as diethylenetriaminepentaacetic acid (DTPA), 1,4,7,10-tetraazacyclododecane-1,4,7,10-tetraacetic acid (DOTA), (DO3A), 2-benzyl-DOTA, alpha-(2-phenethyl)1,4,7,10-tetraazacyclododecane-1-acetic-4,7,10-tris(methylacetic) acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine.

(ii) Magnetic Reporters

Other exemplary reporters can include a chelating agent for magnetic resonance agents. Such chelators can include for example, polyamine-polycarboxylate chelators or iminoacetic acid chelators that can be chemically linked to the agents.

Chelators for magnetic resonance imaging agents can be selected to form stable complexes with paramagnetic metal ions, such as Gd(III), Dy(III), Fe(III), and Mn(II), are selected from cyclic and acyclic polyaminocarboxylates such as DTPA, DOTA, DO3A, 2-benzyl-DOTA, alpha-(2-phenethyl)

1,4,7,10-tetraazacyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl]-4'-(3-amino-4-methoxyphenyl)-2,2':6',2"-terpyridine.

In one embodiment, the bacterium targeting agents are conjugated to superparamagnetic metal oxide nanoparticles that are either (a) non-fluorescent or (b)] are fluorescent and can be used in a variety of in vitro and vivo applications. Fluorescent metal oxide nanoparticles that also have magnetic properties can be used for MRI, thus providing a multi-modality imaging agent.

In certain embodiments, the imaging agents can include a fluorescent and/or non-fluorescent superparamagenetic metal oxide nanoparticle with one or more of the following features: (1) a polymer coating suitable for attaching a plurality of agents (2) a non-crosslinked polymer coating suitable for attaching from about 10 to about 300 agents per particle, and (3) a polymer coating that is amenable to efficient chemical linking of the agents with retention of their biological properties to yield molecular imaging agents. The agent modified metal oxide nanoparticle can be a highly stable molecular imaging agent in vitro, both before and after chemical linking of the agents, but yet are labile and/or degradable in vivo.

The bacterium targeting agent conjugated metal oxide nanoparticles can be formulated into a pharmaceutical composition suitable for administration to a subject, for example, an animal and/or a human subject.

(iii) Ultrasound Reporters

For ultrasound imaging, the imaging reporter can include gas-filled bubbles such as Levovist, Albunex, or Echovist, or particles or metal chelates where the metal ions have atomic numbers 21-29, 42, 44 or 57-83. Examples of such compounds are described in Tyler et al., *Ultrasonic Imaging*, 3, pp. 323-29 (1981) and D. P. Swanson, "Enhancement Agents for Ultrasound: Fundamentals," *Pharmaceuticals in Medical Imaging*, pp. 682-87 (1990).

(iv) X-Ray Reporters

Exemplary reporters can comprise iodinated organic molecules or chelates of heavy metal ions of atomic numbers 57 to 83. Examples of such compounds are described in M. Sovak, ed., "Radiocontrast Agents," Springer-Verlag, pp. 23-125 (1984) and U.S. Pat. No. 4,647,447.

C. Linkers

Linker or spacer moieties (L) can be used to chemically link one or more chemical modifiers (M) to the fluorophore and/or to link the bacterium targeting moiety to Q or, if Q is absent, directly to the fluorophores of the agents of the present invention. Useful linker moieties include both natural and non-natural amino acids and nucleic acids, peptides, such as glycine, β-alanine, γ-aminobutyric acid or aminocaproic acid, as well as synthetic linker molecules such as aminoethyl maleimide or aminomethyl benzoic acid, or a polymer such as homobifunctional or heterobifunctional polyethylene glycol (PEG). When the linker is a peptide, the peptide optionally may include proteolytic cleavage site that can be cleaved with a variety of agents, for example, an enzyme.

It is understood that there is no particular structural, size or content limitation for a given linker. Linkers can include, for example, a variety of functional groups such as maleimide, dithiopyridyl, thiol, azide, alkene, or alkyne that permit the assembly of molecules of diverse architecture.

Linkers can be homofunctional linkers or heterofunctional linkers. For example, amine ($NH_2$)-functionalized moieties can be reacted with bifunctional cross-linkers designed to react with amino groups. Particularly useful conjugation reagents that can facilitate formation of a linker or facilitate covalent linkage between, for example, a fluorophore, and an enzymatically cleavable oligopeptide can include a N-hydroxysuccinimide (NHS) ester and/or a maleimide. The NHS ester can react with the amine group of, for example, a peptide or fluorophore. The maleimide can react with the sulfhydryl group of another molecule. Other particularly useful linker moieties are bifunctional crosslinkers such as N-succinimidyl 3-(2-pyridyldithio)propionate (SPDP), long chain-SPDP, maleimidobenzoic acid-N-hydroxysuccinimide ester (MBS), succinimidyl trans-4-(maleimidylmethyl)cyclohexane-1-carboxylate (SMCC), succinimidyl iodoacetate (SIA).

In certain embodiments a linker, if present, may be a derivative of a diamine. A diamine moiety or derivative can provide a linker arm of varying lengths and chemistries for chemically linking molecules by derivatizing, optionally, with carboxylic acids. Non-limiting examples of diamines include ethylenediamine (EDA), propylenediamine, spermidine, spermine, hexanediamine, and diamine-amino acids, such as homolysine, lysine, ornithine, diaminobutyric acid and diaminopropionic acid. In other embodiments, moieties of an imaging agent can be chemically linked to a dicarboxylic acid, for example, succinic acid, glutaric acid, suberic acid, or adipic acid. In one embodiment, the linker is aminoethylmaleimide.

In certain embodiments, a linker can be branched, for example glutamic acid or 5-(aminomethyl) isophthalic acid, or a dendrimer, such as a lysine or glutamic acid dendrimer, with multiple M groups linked to a single site on the fluorophore.

In certain embodiments, L is a a functionalized, substituted or unsubstituted $C_1$-$C_{18}$ alkyl, alkenyl, alkynyl, alkoxy, or thioalkyl group. In other embodiments, L is functionalized, substituted or unsubstituted aromatic or heteroaromatic ring. In other embodiments, L is absent.

In certain embodiments, a linker can be formed from an azide moiety that can react with substituted alkynes in an azide-acetylene Huisgen [3+2] cycloaddition. In certain embodiments the azide or alkyne linker can link a polyethyleneglycol (PEG) moiety to, for example, an enzymatically cleavable oligopeptide. Other contemplated linkers include propargylglycine, pentanoyl, pentynoic acid, propargylic acid, and/or propargylamine moieties.

In certain embodiments, the imaging reporters are directly chemically linked to the bacterium targeting moiety using reactive NHS esters groups on the IR which react with the amine group of the amino-functionalized bacterium targeting moiety. In certain other embodiments, carboxylic acid groups on the IR can be activated in situ by activating agents known in the art, such as 2-(1H-benzotriazole-1-yl)-1,1,3,3,-tetramethyluronium hexafluorophosphate (HBTU), 1-ethyl-3-(3'-dimethylaminopropyl)-carbodiimide hydrochloride (EDC), N,N'-dicyclohexylcarbodiimide (DCC), N,N'-disuccinimidyl carbonate (DSC). In other embodiments, IRs containing a sulfhydryl or thiol group, can be chemically linked to the bacterium targeting moiety via a bifunctional cross-linker that has a second moiety that can react with a sulfhydryl (thiol) group. Such crosslinking agents include, for example and as described above, SPDP, long chain-SPDP, SIA, MBS, SMCC, and others that are well known in the art.

Useful linker moieties include both natural and non-natural amino acids, oligopeptides, for example, linear or cyclic oligopeptides, and nucleic acids. The linker can be a peptide or peptide moiety. The linker can optionally include a proteolytic or non-proteolytic cleavage site, such as an ester linkage, that can be cleaved due to pH changes at the site of interest.

The term "amino acid" as used herein is understood to mean an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Natural amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Other amino acids include, but not limited to, arginosuccinic acid, citrulline, cysteine sulfinic acid, 3,4-dihydroxyphenylalanine, homocysteine, homoserine, ornithine, carnitine, selenocysteine, selenomethionine, 3-monoiodotyrosine, 3,5-diiodotryosine, 3,5,5'-triiodothyronine, and 3,3',5,5'-tetraiodothyronine.

Modified or unusual amino acids which can be used to practice the invention include, but are not limited to, D-amino acids, hydroxylysine, dehydroalanine, pyrrolysine, 2-aminoisobutyric acid, gamma aminobutyric acid, 5-hydroxytryptophan, S-adenosyl methionine, S-adenosyl homocysteine, 4-hydroxyproline, an N-Cbz-protected amino acid, 2,4-diaminobutyric acid, homoarginine, norleucine, N-methylaminobutyric acid, naphthylalanine, phenylglycine, .beta.-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

As used herein, a "pseudopeptide" or "peptidomimetic" is a compound which mimics the structure of an amino acid residue or a peptide, for example, by using linking groups other than via amide linkages (pseudopeptide bonds) and/or by using non-amino acid substituents and/or a modified amino acid residue. A "pseudopeptide residue" means that portion of a pseudopeptide or peptidomimetic that is present in a peptide. The term "pseudopeptide bonds" includes peptide bond isosteres which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation. The following conventional three-letter amino acid abbreviations are used herein: Ala=alanine; Aca=aminocaproic acid, Ahx=6-aminohexanoic acid, Arg=arginine; Asn=asparagines; Asp=aspartic acid; Cha=cyclohexylalanine; Cit=citrulline; Cys=cysteine; Dap=diaminopropionic acid; Gln=glutamine; Glu=glutamic acid; Gly=glycine; H is =histidine; Ile=isoleucine; Leu=leucine; Lys=lysine; Met=methionine; NaI=naphthylalanine; Nle=norleucine; Orn=ornithine; Phe=phenylalanine; Phg=phenylglycine; Pro=praline; Sar=sarcosine; Ser=serine; Thi=Thienylalanine; Thr=threonine; Trp=tryptophan; Tyr=tyrosine; and Val=valine. Use of the prefix D- indicates the D-isomer of that amino acid; for example D-lysine is represented as D-Lys.

The peptides can be synthesized using either solution phase chemistry or solid phase chemistry or a combination of both (Albericio, Curr. Opinion. Cell Biol., 8, 211-221 (2004), M. Bodansky, Peptide Chemistry: A Practical Textbook, Springer-Verlag; N. L. Benoiton, Chemistry of Peptide Synthesis, 2005, CRC Press).

Selective or orthogonal amine protecting groups may be required to prepare the agents of the invention. As used herein, the term "amine protecting group" means any group known in the art of organic synthesis for the protection of amine groups. Such amine protecting groups include those listed in Greene, "Protective Groups in Organic Synthesis" John Wiley & Sons, New York (1981) and "The Peptides: Analysis, Synthesis, Biology, Vol. 3, Academic Press, New York (1981). Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz or Z) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. Also included in the term "amine protecting group" are acyl groups such as azidobenzoyl, p-benzoylbenzoyl, o-benzylbenzoyl, p-acetylbenzoyl, dansyl, glycyl-p-benzoylbenzoyl, phenylbenzoyl, m-benzoylbenzoyl, and benzoylbenzoyl.

In certain embodiments the enzymatically cleavable oligopeptide can include oligo-L-arginine, oligo-L-lysine, oligo-L-aspartic acid or oligo-L-glutamic acid.

The enzymatically cleavable oligopeptide is cleavable by at least one enzyme chosen from hydrolases, elastases, cathepsins, matrix metalloproteases, peptidases, exopeptidases, endopeptidases, carboxypeptidases, glycosidases, lipases, nucleases, lyases, amylases, phospholipases, phosphatases, phosphodiesterases, sulfatases, serine proteases, subtilisin, chymotrypsin, trypsin, threonine proteases, cysteine proteases, calpains, papains, caspases, aspartic acid proteases, pepsins, chymosins, glutamic acid proteases, renin, reductases, and parasitic, viral and bacterial enzymes.

D. Chemical Modifiers

Depending upon the intended use, the bacterium targeting agents can comprise one or more chemical modifiers (M), which can alter the physical, chemical or biological properties of the bacterium targeting agent. In particular, a plurality of Ms can be chemically linked to the fluorophore moiety of the agent. The Ms can be the same or can be different for each occurrence. For example, the Ms may render the bacterium targeting agents more useful for biological imaging, that is, for example, more water soluble, or more dispersible in media for administration, with increased binding specificity, or less immunogenic, or less toxic, or with reduced non-specific binding, altered biodistribution and pharmacokinetic compared to an unsubstituted or lesser substituted fluorophore moiety.

For example, incorporation of methoxypolyethylene glycol (mPEG) or polypeptides or a plurality of anionic Ms may function to modify the pharmacodynamics and blood clearance rates of the bacterium targeting agents in vivo. Other Ms can be chosen to accelerate the clearance of the bacterium targeting agents from background tissue, such as muscle or liver, and/or from the blood, thereby reducing the background interference and improving image quality. Additionally, the Ms can be used to favor a particular route of excretion, e.g., via the kidneys rather than via the liver. The Ms can also aid in formulating probes in pharmaceutical compositions or may be used to alter or preserve the signal reporting properties of the bacterium targeting agents. In particular, chemical linking of polyethylene glycol (PEG) or a derivative thereof to bacterium targeting agents can result in longer blood residence time (longer circulation) and decreasing immunogenicity.

Exemplary modifiers include polyethylene glycol (PEG) and derivatives thereof (for example, alkoxy polyethylene glycol (for example, methoxypolyethylene glycol, ethoxypolyethylene glycol and the like), branched polypropylene glycol, polypropylene glycol, a graft copolymer of polylysine and methoxypolyethyleneglycol, amino acids, peptides, lipids, fatty acids, palmitate, phospholipids, phospholipid-PEG conjugates, carbohydrates (such as dextran, amino-dextran, carboxymethyl-dextran), iron oxide nanoparticles, sulfonates, polysulfonates, cysteic acid, naphthylalanine, phenylalanine, and 3,3-diphenylpropylamine taurine, phosphonates, phosphates, carboxylates and polycarboxylates.

In certain embodiments, the chemical modifier M is an anionic moiety selected from the group consisting of carboxylate, phosphonate, phosphate, iminodiacetate, cysteic acid, or taurine.

In certain embodiments, the chemical modifier M is a sulfonate or polysulfonate.

In certain embodiments, the chemical modifier M is a hydrogen, alcohol, sulfonamide, sulfoxide, sulfone, ketone, an amino acid such as glutamic acid or taurine, a polyamino acid such as polycysteic acid, oligo- or polyethylene glycol, an amine, a quaternary ammonium ion, or a carbohydrate such as glucosamine, galactosamine or mannosamine.

In certain embodiments, the chemical modifier M is a metal chelator, such as ethylenediamine tetraacetic acid (EDTA), diethylenetriamine pentaacetic acid (DTPA), or tetraazacyclododecane tetraacetic acid (DOTA). In another aspect of the invention, one or more metal chelating M groups are coordinated to a metal ion.

In certain embodiments, as discussed above, the biological modifier may be a PEG moiety that has a molecular weight, for example, from about 0.1 kDa to about 50 kDa, about 5 kDa to about 35 kDa, or about 10 kDa to about 30 kDa. Alternatively, the PEG may be dPEG, functionalized at a discrete molecular weight, for example, of about 1100 daltons.

In certain embodiments, the PEG is methoxyPEG$_{(5000)}$-succinimidylpropionate (mPEG-SPA), methoxyPEG$_{(50000)}$-succinimidylsuccinate (mPEG-SS). Such PEGS are commercially available from Nektar Therapeutics or SunBiowest or LaysanBio or NOF.

The PEG moiety can be conjugated to reactive amines on the bacterium targeting agent via a carboxyl functionality. Alternatively, the PEG modifier can be conjugated to the bacterium targeting agent by using a thiol reactive cross linker and then reacting with a thiol group on the PEG.

In one embodiment, the PEG may be branched, or Y-shaped, as available from JenKem USA or NOF, or comb-shaped, or synthesized by coupling two or more PEGs to a small molecule such as glutamic acid.

In other embodiments, the biological modifier can be polyvinylpyrrolidone (PVP)-type polymers. The biological modifier can be a functionalized polyvinylpyrrolidone, for example, carboxy or amine functionalized on one (or both) ends of the polymer (as available from Polymersource) or within the polymer chain.

Alternatively, the biological modifier can include Poly N-(2-hydroxypropyl)methacrylamide (HPMA), or functionalized HPMA (amine, carboxy, etc.), Poly(N-isopropyl acrylamide) or functionalized poly(N-isopropylacrylamide).

Biological modifiers can include straight or branched chain acyl groups, such as pentynoyl; acidic groups, such as succinyl; lower alkyl groups, such as methyl, ethyl, propyl, etc.; carboxyalkyl groups, such as carboxyethyl; haloalkyl groups, such as trifluoromethyl; and the like.

In general, the chemical linking of Ms does not adversely affect the affinity and/or binding properties of the bacterium targeting agents.

E. First Group of Exemplary Bacterial Targeting Agents

The bacterial targeting moieties, imaging reporters, linkers, and optionally chemical modifying moieties described above can be combined in different permutations to provide a variety of bacterial targeting agents. Exemplary bacterial targeting agents are described below.

One aspect of the invention provides a bacterial targeting agent that comprises at least one bacterium targeting moiety chemically linked to a fluorophore, wherein a plurality of chemical modifying moieties (M) is chemically linked to fluorophore. Optionally, one or more linker (L) moieties can be used to chemically link the bacterium targeting moiety to the fluorophore or the M to the fluorophore.

In certain embodiments, the bacterium targeting agent will have an affinity for negatively charged cell surfaces; such as for bacterial and apoptotic cell surfaces; including bacterial cell membranes. In other embodiments, the affinity for bacterial and apoptotic cell surfaces is greater than healthy mammalian cell surfaces. A “bacterium targeting moiety”, as defined herein, is a molecule that specifically binds with negatively charged bacterial cell surfaces. The binding between a bacterium targeting moiety and a negatively charged cell surface may be covalent or non-covalent (for example, electrostatic interactions, hydrophobic interactions, van der Waals interactions, hydrogen bonding, dipole interactions, etc.). The binding between a bacterium targeting moiety and a negatively charged cell surface is non-covalent.

The “fluorophore” (F) may be any suitable chemical or substance which is used to provide fluorescent signal or contrast in imaging and that is detectable by imaging techniques. In certain embodiments, F comprises, for example, a cyanine dye, carbocyanine dye, indocyanine dye, or a polymethine fluorescent dye. In certain embodiments, F comprises a symmetrical cyanine dye. In other embodiments, F comprises and unsymmetrical cyanine dye. In other embodiments, F may also be modified with a plurality of chemical modifying groups allowing optimization of the in vitro and in vivo properties of the agent and ultimately the performance of the agent as a fluorescence imaging agent.

The bacterium targeting agent can have an affinity for bacterial cell surfaces; for example, Gram-positive and Gram-negative bacteria. In one embodiment, the bacterium targeting agent also has an affinity for negatively-charged apoptotic cells. In certain embodiments, the bacterium targeting agent binds to negatively-charged cells that are upregulated during infection and apoptosis.

Another aspect of the invention provides bacterium targeting agent comprising:

(i) a bacterium targeting moiety comprising a positively charged moiety optionally substituted with an aliphatic, aromatic or heteroaromatic moiety; and (ii) an imaging reporter chemically linked, optionally through a linker (L) moiety to the bacterium targeting moiety; and a fluorescent reporter chemically linked, optionally through a linker (L) moiety to the bacterium targeting moiety wherein the fluorescent moiety bears a plurality of chemical modifying groups.

The term “chemically linked” is understood to mean connected by an attractive force between atoms strong enough to allow the combined aggregate to function as a unit. This includes, but is not limited to, chemical bonds such as covalent bonds, non-covalent bonds such as ionic bonds, metallic bonds, and bridge bonds, hydrophobic interactions, hydrogen bonds, and van der Waals interactions.

Another aspect of the invention provides a bacterium targeting agent comprising:

(i) a bacterium targeting moiety comprising a positively charged 1,4-diazabicyclo[2.2.2]octane (DABCO) moiety optionally substituted with an aliphatic, aromatic or heteroaromatic moiety; and (ii) an imaging reporter chemically linked, optionally through a linker (L) moiety to the bacterium targeting moiety; and a fluorescent reporter chemically linked, optionally through a linker (L) moiety to the bacterium targeting moiety wherein the fluorescent moiety bears a plurality of chemical modifying groups.

F. Second Group of Exemplary Bacterium Targeting Agents

Another aspect of the invention provides a bacterium target agent that is a compound of formula (I):

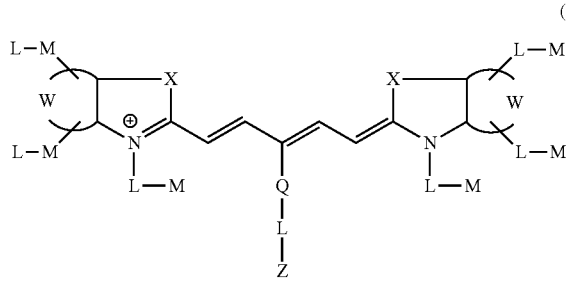

or a salt thereof, wherein:
Z is a bacterium targeting moiety comprising:

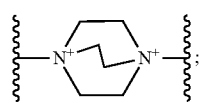

(b) an aliphatic, aromatic or heteroaromatic moiety, each of which is optionally substituted; and
(c) one or more anions as needed to provide a charge-neutral compound;
L is, independently for each occurrence, a bond or a linker moiety;
Q is selected from a group consisting of substituted or unsubstituted aryl, substituted or unsubstituted heteroaryl, $C_1$-$C_{18}$ alkyl, alkenyl, alkynyl, alkoxy, or thioalkyl group, or is absent;
W represents a benzo-condensed, a naphtho-condensed or a pyrido-condensed ring;

X is, independently for each occurrence, selected from the group consisting of $C(CH_2Y_1)(CH_2Y_2)$, O, S, and Se;
$Y_1$ and $Y_2$ are independently selected from the group consisting of H and a $C_1$-$C_{20}$ aliphatic group optionally substituted with L-M; and
M, independently for each occurrence, is hydrogen or a chemical modifying moiety.

In certain embodiments, Z is

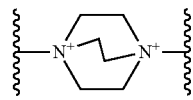

bonded to an aliphatic, aromatic or heteroaromatic moiety, each of which is optionally substituted; and one or more anions as needed to provide a charge-neutral compound. The aliphatic, aromatic or heteroaromatic moiety is bonded to one of the nitrogen atoms in

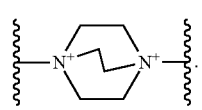

In certain embodiments, L is a bond and M is hydrogen.

Another aspect of the invention provides a bacterium targeting agent that is a compound of formula (II):

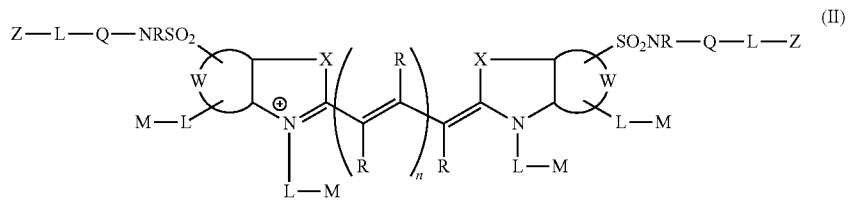

or a salt thereof, wherein:
Z represents independently for each occurrence a bacterium targeting moiety comprising:

(b) an aliphatic, aromatic or heteroaromatic moiety, each of which is optionally substituted; and
(c) one or more anions as needed to provide a charge-neutral compound;
L is, independently for each occurrence, a bond or a linker moiety;
Q is selected from a group consisting of substituted or unsubstituted aryl, substituted or unsubstituted heteroaryl, $C_1$-$C_{18}$ alkyl, alkenyl, alkynyl, alkoxy, or thioalkyl group, or is absent;
R represents independently for each occurrence hydrogen, substituted or unsubstituted aryl, substituted or unsubstituted heteroaryl, $C_1$-$C_{18}$ alkyl, alkenyl, alkynyl, alkoxy, or thioalkyl group, each of which are optionally substituted with L-M;

n is 1, 2, or 3;

W represents a benzo-condensed, a naphtho-condensed, or a pyrido-condensed ring;

X is, independently for each occurrence, selected from the group consisting of $C(CH_2Y_1)(CH_2Y_2)$, O, S, and Se;

$Y_1$ and $Y_2$ are independently hydrogen or alkyl; and

M, independently for each occurrence, is hydrogen or a chemical modifying moiety.

In certain embodiments, the chemical fragment "$SO_2NR$-Q-L-Z" is —S(O)$_2$N(alkyl)-($C_1$-$C_6$ alkylene)-C(O)N(H)—alkylene-C(O)N(H)-arylene-alkylene-(substituted heterocyclyl containing two quaternary ring nitrogen atoms). In certain embodiments, the compound comprises one or more anions (such as an alkyl-$CO_2^-$ anion) as needed to provide a charge-neutral compound. In certain embodiments, R is hydrogen or methyl. In certain embodiments, X is $C(CH_3)_2$. In certain embodiments, Z is

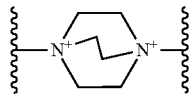

bonded to an aliphatic, aromatic or heteroaromatic moiety, each of which is optionally substituted; and one or more anions as needed to provide a charge-neutral compound. The aliphatic, aromatic or heteroaromatic moiety is bonded to one of the nitrogen atoms in

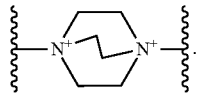

In certain embodiments, L is a bond and M is hydrogen.

Another aspect of the invention provide a bacterium targeting agent that is a compound of formula (III):

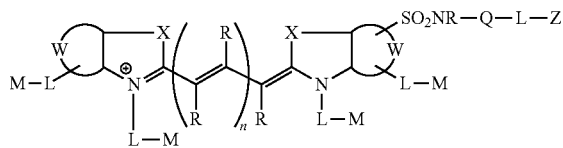

(III)

or a salt thereof, wherein:

Z is a bacterium targeting moiety comprising:

(a)

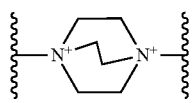

(b) an aliphatic, aromatic or heteroaromatic moiety, each of which is optionally substituted; and (c) one or more anions as needed to provide a charge-neutral compound;

L is, independently for each occurrence, a bond or a linker moiety;

Q is selected from a group consisting of substituted or unsubstituted aryl, substituted or unsubstituted heteroaryl, $C_1$-$C_{18}$ alkyl, alkenyl, alkynyl, alkoxy, or thioalkyl group, or is absent;

R represents independently for each occurrence hydrogen, substituted or unsubstituted aryl, substituted or unsubstituted heteroaryl, $C_1$-$C_{18}$ alkyl, alkenyl, alkynyl, alkoxy, or thioalkyl group, each of which are optionally substituted with L-M;

n is 1, 2, or 3;

W represents a benzo-condensed, a naphtho-condensed or a pyrido-condensed ring;

X is, independently for each occurrence, selected from the group consisting of $C(CH_2Y_1)(CH_2Y_2)$, O, S, and Se;

$Y_1$ and $Y_2$ are independently hydrogen or alkyl; and

M, independently for each occurrence, is hydrogen or a chemical modifying moiety.

In certain embodiments, the chemical fragment "$SO_2NR$-Q-L-Z" is —S(O)$_2$N(alkyl)-($C_1$-$C_6$ alkylene)-C(O)N(H)—alkylene-C(O)N(H)-arylene-alkylene-(substituted heterocyclyl containing two quaternary ring nitrogen atoms). In certain embodiments, the compound comprises one or more anions (such as an alkyl-$CO_2^-$ anion) as needed to provide a charge-neutral compound. In certain embodiments, Z is

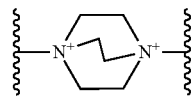

bonded to an aliphatic, aromatic or heteroaromatic moiety, each of which is optionally substituted; and one or more anions as needed to provide a charge-neutral compound. The aliphatic, aromatic or heteroaromatic moiety is bonded to one of the nitrogen atoms in

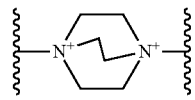 [SMILES: *[N+]12CC[N+](*)(CC1)CC2]

In certain embodiments, L is a bond and M is hydrogen.

In certain embodiments, R is hydrogen or methyl. In certain embodiments, X is $C(CH_3)_2$.

In certain embodiments, the agent is fluorescent in the far-red or near-infrared wavelengths.

Another aspect of the invention provides a bacterium targeting agent that is a compound of formula (IV):

$$F\text{-}(L)_n\text{-}(Z)_m \quad (IV)$$

or a salt thereof, wherein:

n=1-8 m=1, 2, 3, or 4

F is a far red or near infrared fluorochrome;

L is an optional linker; and

Z represents independently for each occurrence a bacterium targeting moiety comprising:

(a)

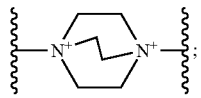

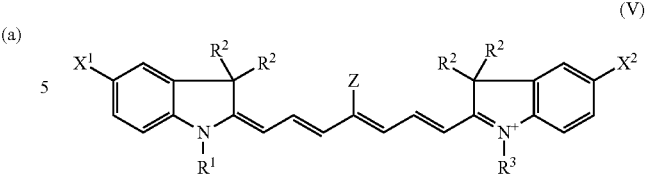

(V)

(b) an aliphatic, aromatic, heteroaromatic, or PEG moiety, each of which is optionally substituted; and (c) one or more anions as needed to provide a charge-neutral compound.

In certain embodiments, the chemical modifying moiety (M) is selected from the group consisting of a hydrogen, alcohol, sulfonate, polysulfonate, cysteic acid, sulfonamide, sulfoxide, sulfone, carboxylate, ketone, phosphonate, phosor a salt thereof, wherein:

$X^1$ and $X^2$ each represent independently hydrogen or one of the following provided that $X^1$ and $X^2$ are not both hydrogen:
(a) —S(O)$_2$N(R$^4$)—(C$_1$-C$_6$ alkylene)-C(O)N(R$^5$)—Y-(substituted heterocyclyl containing one quaternary ring nitrogen atom)-A;
(b) —S(O)$_2$N(R$^4$)—(C$_1$-C$_6$ alkylene)-C(O)N(R$^5$)—Y-(substituted heterocyclyl containing two quaternary ring nitrogen atoms)-(A)$_2$; or

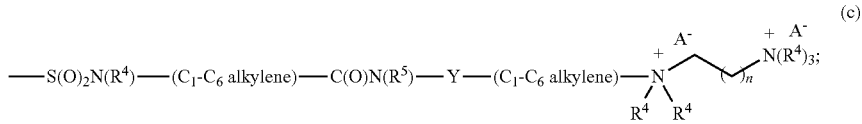

(c)

phate; iminodiacetate, ethylenediamine tetraacetic acid, diethylenetriamine pentaacetic acid, tetraazacyclododecane tetraacetic acid, an amino acid or polyamino acid, oligo- or polyethylene glycol, amine, quaternary ammonium ion, sugars, glucosamine, galactosamine, mannosamine, polyethylene glycol (PEG) and derivatives thereof, for example, alkoxy polyethylene glycol (for example, methoxypolyethylene glycol, ethoxypolyethylene glycol and the like), branched polypropylene glycol, polypropylene glycol, a graft copolymer of poly-lysine and methoxypolyethyleneglycol, peptides, lipids, fatty acids, palmitate, phospholipids, phospholipid-PEG conjugates, carbohydrates (such as dextran, amino-dextran, carboxymethyl-dextran), iron oxide nanoparticles, naphthylalanine, phenylalanine, 3,3-diphenylpropylamine, taurine, phosphonates, phosphates, carboxylates and polycarboxylates.

In other embodiments, the chemical modifier(s) M reduce the nonspecific cell membrane permeability of the agent. In other embodiments, the chemical modifier(s) M reduce the nonspecific tissue accumulation of the agent when administered to a live animal.

In certain embodiments, the bond or linker moiety (L) comprises a diradical of a moiety selected from the group consisting of glycine, alanine, β-alanine, —NH—(CH$_2$)$_n$—C(=O)— where n=1-8,4-aminomethylbenzoic acid, cysteic acid, glutamic acid, amino-polyethylene glycol-carboxylic acid, amino-polyethylene glycol amine, ethylenediamine, propylenediamine, spermidine, spermine, hexanediamine, and diamine-amino acids, such as homolysine, lysine, ornithine, diaminobutyric acid and diaminopropionic acid, succinic acid, glutaric acid, suberic acid, adipic acid, amide, triazole, urea, or thiourea.

G. Third Group of Exemplary Bacterial Targeting Agents

One aspect of the invention provides a compound represented by Formula V:

n is 1, 2, 3, or 4;

A is a monvalent anion or absent;

Y is one of the following:
(a) ψ-alkylene-C(O)N(R$^5$)-arylene-alkylene-; or
(b) ψ-heteroalkylene-C(O)N(R$^5$)-alkylene-C(O)N(R$^5$)-arylene-alkylene-;

ψ is a bond to the amide nitrogen atom;

Z is hydrogen or —S-alkyl;

$R^1$ and $R^3$ each represent independently alkyl or alkylene-SO$_3^-$M$^+$;

$R^2$ and $R^4$ each represent independently for each occurrence methyl, ethyl, or propyl;

$R^5$ represents independently for each occurrence hydrogen, methyl, ethyl, or propyl; and M is a monovalent cation or absent.

In certain embodiments, $X^1$ is hydrogen. In certain embodiments, $X^2$ is —S(O)$_2$N(R$^4$)—(C$_1$-C$_6$ alkylene)-C(O)N(R$^5$)—Y-(substituted heterocyclyl containing two quaternary ring nitrogen atoms)-(A)$_2$. In certain embodiments, $X^1$ and $X^2$ are —S(O)$_2$N(R$^4$)—(C$_1$-C$_6$ alkylene)-C(O)N(R$^5$)—Y-(substituted heterocyclyl containing two quaternary ring nitrogen atoms)-(A)$_2$.

In certain embodiments, the substituted heterocyclyl containing two quaternary ring nitrogen atoms is a 5-6 membered saturated heterocyclic ring containing two quaternary ring nitrogen atoms, wherein said ring is substituted with 1, 2, or 3 substituents independently selected from the group consisting of alkyl, alkylene-C(O)NH$_2$, and alkylene-C(O)N(H)-alkyl. In certain embodiments, the substituted heterocyclyl containing one quaternary ring nitrogen atom is a 5-6 membered aromatic heterocyclic ring containing one quaternary ring nitrogen atom, wherein said ring is substituted with 1, 2, or 3 substituents independently selected from the group consisting of alkyl, alkylene-C(O)NH$_2$, and alkylene-C(O)N(H)-alkyl. In certain embodiments, the substituted heterocyclyl containing two quaternary ring nitrogen atoms is one of the following:

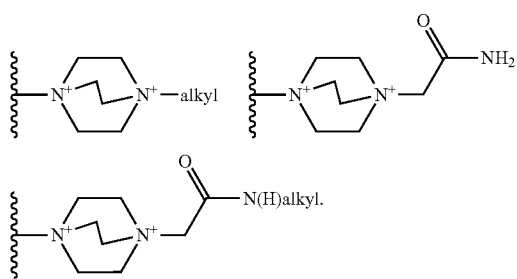

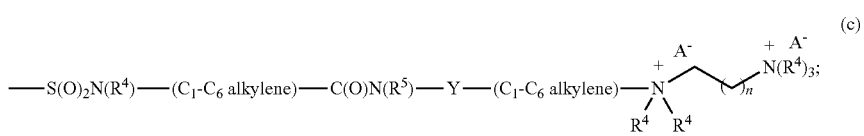

In certain embodiments, Y is one of the following: (a) ψ-CH$_2$—C(O)N(H)-phenyl-(C$_1$-C$_4$)alkylene-; or (b) ψ-(CH$_2$CH$_2$—O)$_{2-4}$-CH$_2$CH$_2$—C(O)N(H)—(C$_1$-C$_2$)alkylene-C(O)N(H)-phenyl-(C$_1$-C$_4$)alkylene. In certain embodiments, Y is one of the following:

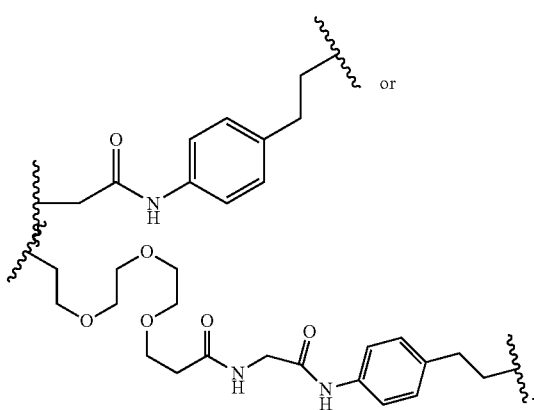

In certain embodiments, R$^1$ is alkylene-SO$_3^-$M$^+$. In certain embodiments, R$^3$ is alkyl. In certain embodiments, R$^1$ and R$^3$ are alkylene-SO$_3^-$M$^+$. In certain embodiments, R$^1$ and R$^3$ are —(CH$_2$)$_3$—SO$_3^-$M$^+$. In certain embodiments, R$^2$ is methyl. In certain embodiments, R$^4$ is methyl.

In certain embodiments, Z is hydrogen. In certain embodiments, M is absent.

In certain embodiments, A is alkyl-CO$_2$—. In certain other embodiments, A is halogen, haloalkyl-CO$_2^-$, alkyl-SO$_3^-$, or aryl-SO$_3^-$.

Another aspect of the invention provides a compound represented by Formula V-I:
or

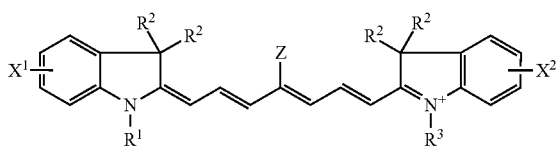

a salt thereof, wherein:

X$^1$ and X$^2$ each represent independently hydrogen or one of the following provided that X$^1$ and X$^2$ are not both hydrogen:

(a) —S(O)$_2$N(R$^4$)—(C$_1$-C$_6$ alkylene)-C(O)N(R$^5$)—Y-(substituted heterocyclyl containing one quaternary ring nitrogen atom)-A;

(b) —S(O)$_2$N(R$^4$)—(C$_1$-C$_6$ alkylene)-C(O)N(R$^5$)—Y-(substituted heterocyclyl containing two quaternary ring nitrogen atoms)-(A)$_2$; or n is 1, 2, 3, or 4;

A is a monvalent anion or absent;

Y is one of the following:

(a) ψ-alkylene-C(O)N(R$^5$)-arylene-alkylene-; or (b) ψ-heteroalkylene-C(O)N(R$^5$)-alkylene-C(O)N(R$^5$)-arylene-alkylene-;

ψ is a bond to the amide nitrogen atom;

Z is hydrogen or —S-alkyl;

R$^1$ and R$^3$ each represent independently alkyl or alkylene-SO$_3^-$M$^+$;

R$^2$ and R$^4$ each represent independently for each occurrence methyl, ethyl, or propyl;

R$^5$ represents independently for each occurrence hydrogen, methyl, ethyl, or propyl; and M is a monovalent cation or absent.

Another aspect of the invention provides a compound represented by Formula VI:

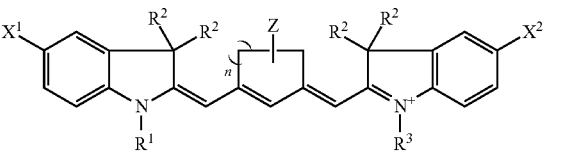

or a salt thereof, wherein:

X$^1$ and X$^2$ each represent independently hydrogen or one of the following provided that X$^1$ and X$^2$ are not both hydrogen:

(a) —S(O)$_2$N(R$^4$)—(C$_1$-C$_6$ alkylene)-C(O)N(R$^5$)—Y-(substituted heterocyclyl containing one quaternary ring nitrogen atom)-A;

(b) —S(O)$_2$N(R$^4$)—(C$_1$-C$_6$ alkylene)-C(O)N(R$^5$)—Y-(substituted heterocyclyl containing two quaternary ring nitrogen atoms)-(A)$_2$; or

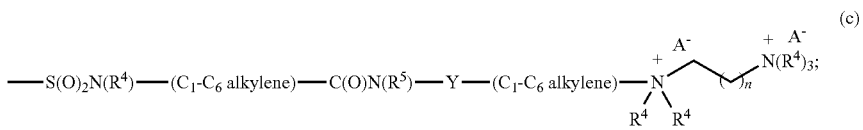

n represents independently for each occurrence 1, 2, 3, or 4;
A is a monvalent anion or absent;
Y is one of the following:
(a) ψ-alkylene-C(O)N($R^5$)-arylene-alkylene-; or
(b) ψ-heteroalkylene-C(O)N($R^5$)-alkylene-C(O)N($R^5$)-arylene-alkylene-;
ψ is a bond to the amide nitrogen atom;
Z is hydrogen or alkyl;
$R^1$ and $R^3$ each represent independently alkyl or alkylene-$SO_3^-M^+$;
$R^2$ and $R^4$ each represent independently for each occurrence methyl, ethyl, or propyl;
$R^5$ represents independently for each occurrence hydrogen, methyl, ethyl, or propyl; and
M is a monovalent cation or absent.

In certain embodiments, $X^1$ is —S(O)$_2$N($R^4$)—($C_1$-$C_6$ alkylene)-C(O)N($R^5$)—Y-(substituted heterocyclyl containing two quaternary ring nitrogen atoms)-(A)$_2$.

In certain embodiments, the substituted heterocyclyl containing two quaternary ring nitrogen atoms is a 5-6 membered saturated heterocyclic ring containing two quaternary ring nitrogen atoms, wherein said ring is substituted with 1, 2, or 3 substituents independently selected from the group consisting of alkyl, alkylene-C(O)NH$_2$, and alkylene-C(O)N(H)-alkyl. In certain embodiments, substituted heterocyclyl containing one quaternary ring nitrogen atom is a 5-6 membered aromatic heterocyclic ring containing one quaternary ring nitrogen atom, wherein said ring is substituted with 1, 2, or 3 substituents independently selected from the group consisting of alkyl, alkylene-C(O)NH$_2$, and alkylene-C(O)N(H)-alkyl. In certain embodiments, the substituted heterocyclyl containing two quaternary ring nitrogen atoms is one of the following:

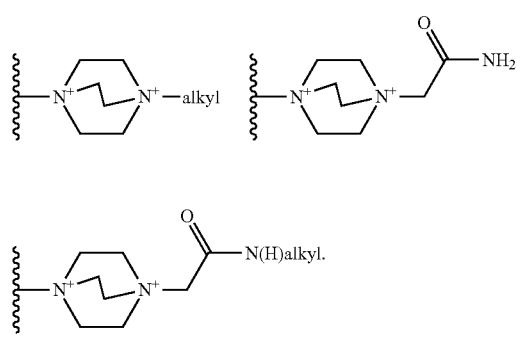

In certain embodiments, $X^2$ is hydrogen

In certain embodiments, Y is one of the following: (a) ψ-CH$_2$—C(O)N(H)-phenyl-($C_1$-$C_4$)alkylene-; or (b) ψ-(CH$_2$CH$_2$—O)$_{2-4}$-CH$_2$CH$_2$—C(O)N(H)—($C_1$-$C_2$)alkylene-C(O)N(H)-phenyl-($C_1$-$C_4$)alkylene. In certain embodiments, Y is one of the following:

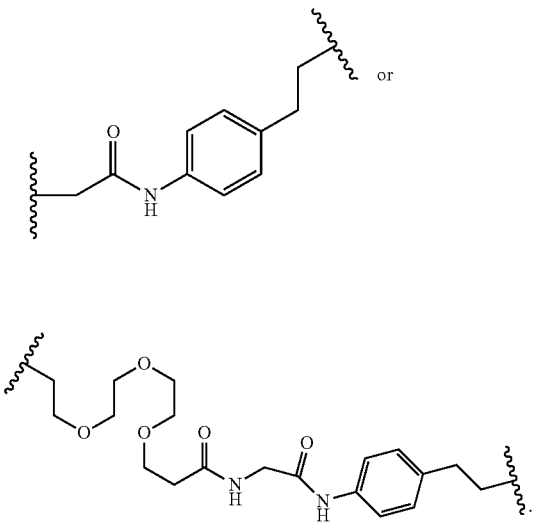

In certain embodiments, $R^1$ is alkyl. In certain embodiments, $R^3$ is alkylene-$SO_3^-M^+$. In certain embodiments, $R^3$ is —(CH$_2$)$_3$—$SO_3^-M^+$. In certain embodiments, $R^2$ is methyl. In certain embodiments, $R^4$ is methyl. In certain embodiments, Z is hydrogen. In certain embodiments, M is absent.

In certain embodiments, A is alkyl-$CO_2^-$. In certain other embodiments, A is halogen, haloalkyl-$CO_2^-$, alkyl-$SO_3^-$, or aryl-$SO_3^-$.

In certain embodiments, the compound is the following or a salt thereof:

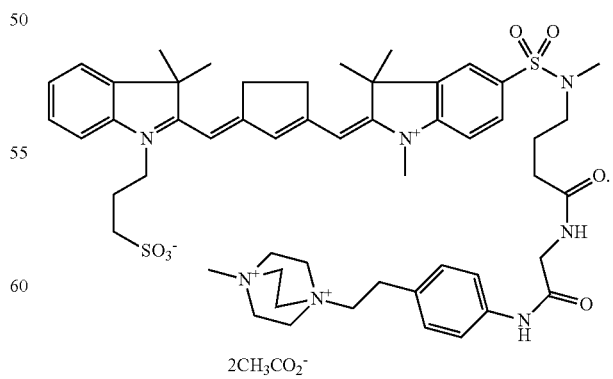

2CH$_3$CO$_2^-$

Another aspect of the invention provides a compound represented by Formula VI-I:

(VI-I)

[Structure of Formula VI-I]

or a salt thereof, wherein:

$X^1$ and $X^2$ each represent independently hydrogen or one of the following provided that $X^1$ and $X^2$ are not both hydrogen:
(a) —S(O)$_2$N(R$^4$)—(C$_1$-C$_6$ alkylene)-C(O)N(R$^5$)—Y-(substituted heterocyclyl containing one quaternary ring nitrogen atom)-A;
(b) —S(O)$_2$N(R$^4$)—(C$_1$-C$_6$ alkylene)-C(O)N(R$^5$)—Y-(substituted heterocyclyl containing two quaternary ring nitrogen atoms)-(A)$_2$; or —S(O)$_2$N(R$^4$)—(C$_1$-C$_6$ alkylene)—C(O)N(R$^5$)—Y—(C$_1$-C$_6$ alkylene)—N$^+$(R$^4$)(R$^4$)—()$_n$—N(R$^4$)$_3$$^+$ ; A$^-$ A$^-$ (c)

n represents independently for each occurrence 1, 2, 3, or 4;
A is a monvalent anion or absent;

Y is one of the following:
(a) ψ-alkylene-C(O)N(R$^5$)-arylene-alkylene-; or
(b) ψ-heteroalkylene-C(O)N(R$^5$)-alkylene-C(O)N(R$^5$)-arylene-alkylene-;
ψ is a bond to the amide nitrogen atom;
Z is hydrogen or alkyl;
R$^1$ and R$^3$ each represent independently alkyl or alkylene-SO$_3$$^-$M$^+$;
R$^2$ and R$^4$ each represent independently for each occurrence methyl, ethyl, or propyl;
R$^5$ represents independently for each occurrence hydrogen, methyl, ethyl, or propyl; and
M is a monovalent cation or absent.

Another aspect of the invention provides a compound represented by Formula VII:

(VII)

[Structure of Formula VII]

or a salt thereof, wherein:

X is one of the following:

(a) —(C$_1$-C$_6$ alkylene)-C(O)N(R$^5$)—Y-(substituted heterocyclyl containing one quaternary ring nitrogen atom)-A;

(b) —(C$_1$-C$_6$ alkylene)-C(O)N(R$^5$)—Y-(substituted heterocyclyl containing two quaternary ring nitrogen atoms)-(A)$_2$; or —(C$_1$-C$_6$ alkylene)—C(O)N(R$^5$)—Y—(C$_1$-C$_6$ alkylene)—N$^+$(R$^4$)(R$^4$)—()$_n$—N(R$^4$)$_3$$^+$ ; A$^-$ A$^-$ (c)

n is 1, 2, 3, or 4;
A is a monvalent anion or absent;
Y is one of the following:
(a) ψ-alkylene-C(O)N(R$^5$)-arylene-alkylene-; or
(b) ψ-heteroalkylene-C(O)N(R$^5$)-alkylene-C(O)N(R$^5$)-arylene-alkylene-;
ψ is a bond to the amide nitrogen atom;
Z is arylene;
R$^1$ and R$^3$ each represent independently alkyl or alkylene-SO$_3$$^-$M$^+$;
R$^2$ and R$^4$ each represent independently for each occurrence methyl, ethyl, or propyl;
R$^5$ represents independently for each occurrence hydrogen, methyl, ethyl, or propyl; and
M is a monovalent cation or absent.

In certain embodiments, X is —(C$_1$-C$_6$ alkylene)-C(O)N(R$^5$)—Y-(substituted heterocyclyl containing two quaternary ring nitrogen atoms)-(A)$_2$.

In certain embodiments, the substituted heterocyclyl containing two quaternary ring nitrogen atoms is one of the following:

[Two piperazinium structures shown: one with N$^+$—alkyl, and one with N$^+$—CH$_2$C(O)NH$_2$]

41

-continued

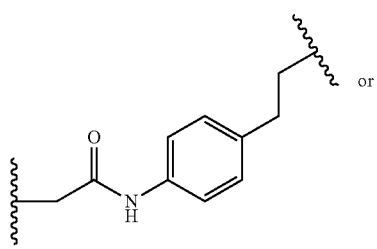

In certain embodiments, Y is ψ-CH$_2$—C(O)N(H)-phenyl-(C$_1$-C$_4$)alkylene-.

In certain embodiments, Y is one of the following:

In certain embodiments, Z is

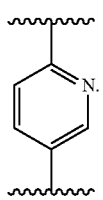

In certain embodiments, R$^1$ is alkyl. In certain embodiments, R$^3$ is alkylene-SO$_3^-$M$^+$. In certain embodiments, R$^3$ is —(CH$_2$)$_3$—SO$_3^-$M$^+$. In certain embodiments, R$^2$ is methyl. In certain embodiments, R$^4$ is methyl. In certain embodiments, M is absent.

42

In certain embodiments, A is alkyl-CO$_2^-$. In certain other embodiments, A is halogen, haloalkyl-CO$_2^-$, alkyl-SO$_3^-$, or aryl-SO$_3^-$.

In certain embodiments, the compound is one of the following or a salt thereof:

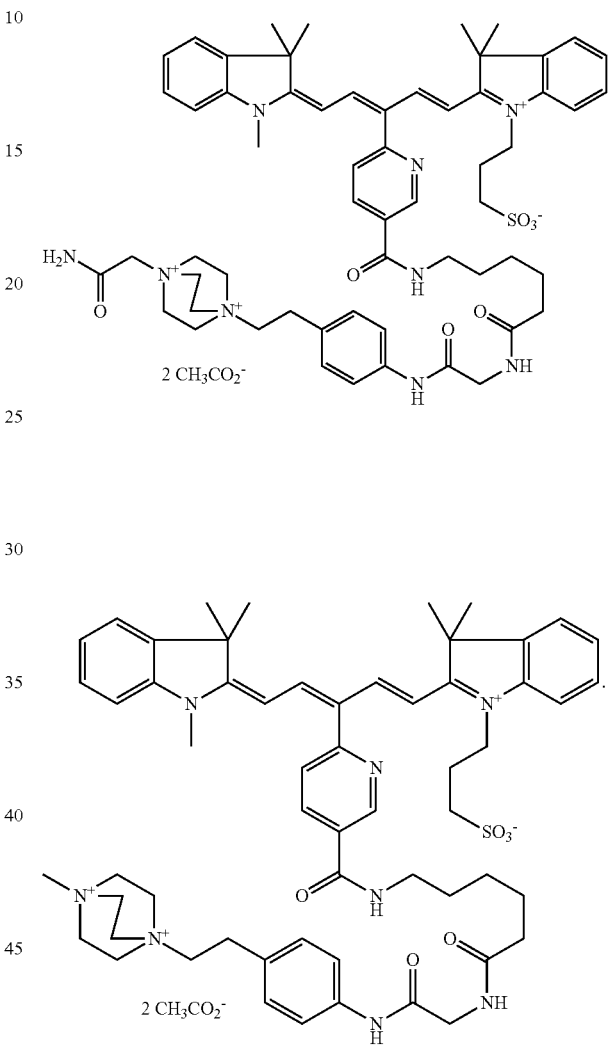

H. Exemplary Specific Bacterial Targeting Agents

Useful bacterium targeting agents can be created using one or more of the bacterium targeting moieties, imaging reporters, biological modifiers, and linkers described hereinabove using standard chemistries known in the art. Depending upon the particular application, the bacterium targeting agents can be designed to be water soluble or water dispersible (i.e., sufficiently soluble or suspendable in aqueous or physiological media solutions). The bacterium targeting agents preferably do not have any undesired phototoxic properties and/or display low serum protein binding affinity. Exemplary specified bacterium targeting agents are listed in Table 4. In certain embodiments, the bacterium targeting agent is a bacterium targeting agent listed in Table 4 or a salt thereof

TABLE 4

| Compound No. | Chemical Structure | Chemical Name |
|---|---|---|
| A1 | 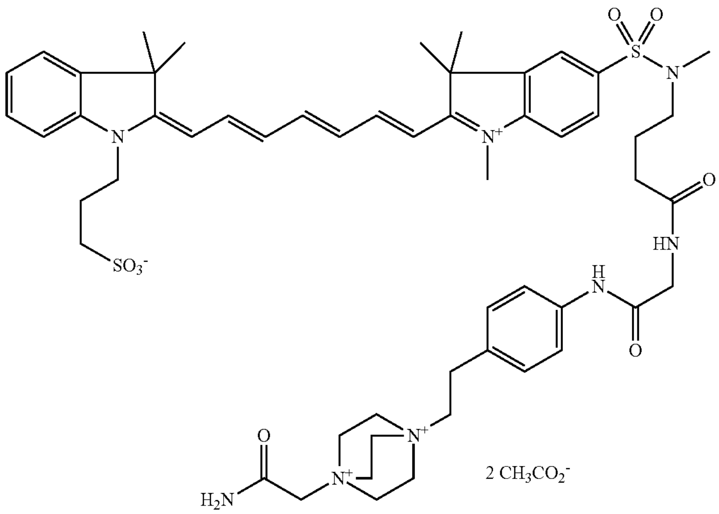 | 3-((E)-2-((2E,4E,6E)-7-(5-(N-(4-((2-((4-(2-(4-(2-amino-2-oxoethyl)-1,4-diazabicyclo[2.2.2]octan-1,4-diium-1-yl)ethyl)phenyl)amino)-2-oxoethyl)amino)-4-oxobutyl)-N-methylsulfamoyl)-1,3,3-trimethyl-3H-indol-1-ium-2-yl)hepta-2,4,6-trien-1-ylidene)-3,3-dimethylindolin-1-yl)propane-1-sulfonate di-acetate |
| A2 | 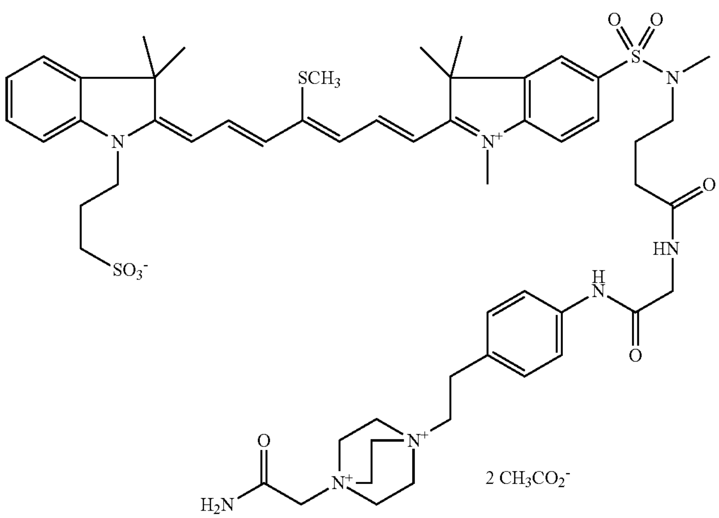 | 3-((E)-2-((2E,4Z,6E)-7-(5-(N-(4-((2-((4-(2-(4-(2-amino-2-oxoethyl)-1,4-diazabicyclo[2.2.2]octan-1,4-diium-1-yl)ethyl)phenyl)amino)-2-oxoethyl)amino)-4-oxobutyl)-N-methylsulfamoyl)-1,3,3-trimethyl-3H-indol-1-ium-2-yl)-4-(methylthio)hepta-2,4,6-trien-1-ylidene)-3,3-dimethylindolin-1-yl)propane-1-sulfonate di-acetate |
| A3 | 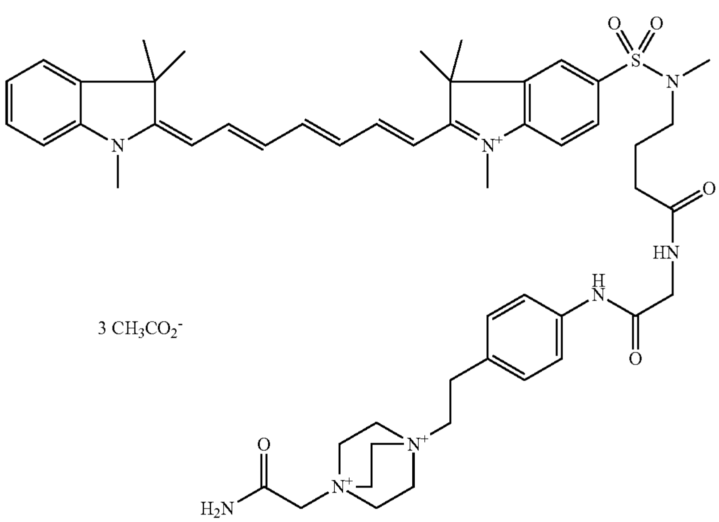 [SMILES: CN1/C(=C/C=C/C=C/C=C/C2=[N+](C)c3ccc(S(=O)(=O)N(C)CCCC(=O)NCC(=O)Nc4ccc(CC[N+]56CC[N+](CC(N)=O)(CC5)CC6)cc4)cc3C2(C)C)C(C)(C)c2ccccc21 ; "3 CH3CO2-"] | 1-(2-amino-2-oxoethyl)-4-(4-(2-(4-(N,1,3,3-tetramethyl-2-((1E,3E,5E,7E)-7-(1,3,3-trimethylindolin-2-ylidene)hepta-1,3,5-trien-1-yl)-3H-indol-1-ium-5-sulfonamido)butanamido)acetamido)phenethyl)-1,4-diazabicyclo[2.2.2]octane-1,4-diium tri-acetate |

TABLE 4-continued

| Compound No. | Chemical Structure | Chemical Name |
|---|---|---|
| A4 | 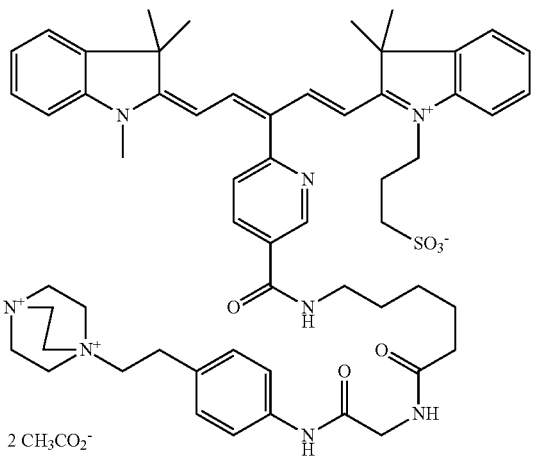 | 3-(2-((1E,3Z,5E)-3-(5-((6-((2-((4-(2-(4-(2-amino-2-oxoethyl)-1,4-diazabicyclo[2.2.2]octan-1,4-diium-1-yl)ethyl)phenyl)amino)-2-oxoethyl)amino)-6-oxohexyl)carbamoyl)pyridin-2-yl)-5-(1,3,3-trimethylindolin-2-ylidene)penta-1,3-dien-1-yl)-3,3-dimethyl-3H-indol-1-ium-1-yl)propane-1-sulfonate di-acetate |
| A5 | 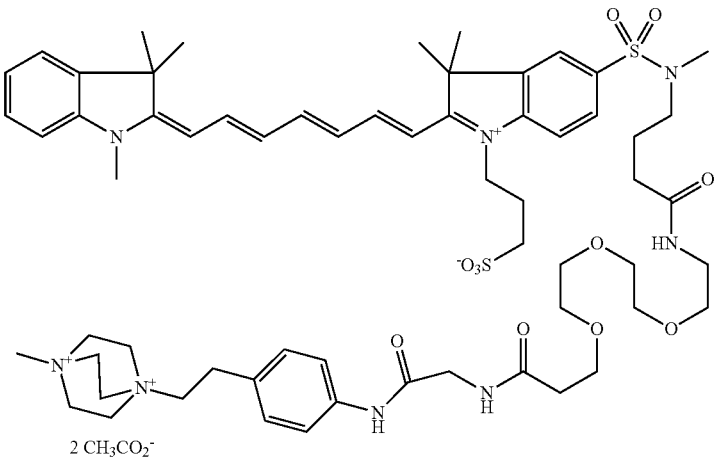 | 3-(3,3-dimethyl-5-(N-methyl-N-(4-((2-((4-(2-(4-methyl-1,4-diazabicyclo[2.2.2]octan-1,4-diium-1-yl)ethyl)phenyl)amino)-2-oxoethyl)amino)-4-oxobutyl)sulfamoyl)-2-((1E,3E,5E,7E)-7-(1,3,3-trimethylindolin-2-ylidene)hepta-1,3,5-trien-1-yl)-3H-indol-1-ium-1-yl)propane-1-sulfonate di-acetate |
| A6 | 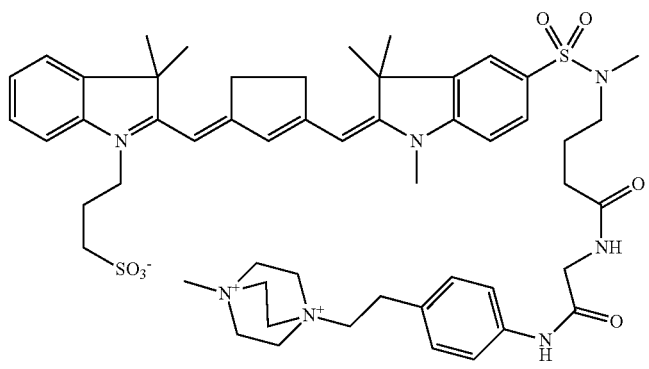 | 3-(3,3-dimethyl-2-((E)-(3-((E)-(1,3,3-trimethyl-5-(N-methyl-N-(4-((2-((4-(2-(4-methyl-1,4-diazabicyclo[2.2.2]octan-1,4-diium-1-yl)ethyl)phenyl)amino)-2-oxoethyl)amino)-4-oxobutyl)sulfamoyl)indolin-2-ylidene)methyl)cyclopent-2-en-1-ylidene)methyl)-3H-indol-1-ium-1-yl)propane-1-sulfonate di-acetate |

TABLE 4-continued

| Compound No. | Chemical Structure | Chemical Name |
|---|---|---|
| A7 | 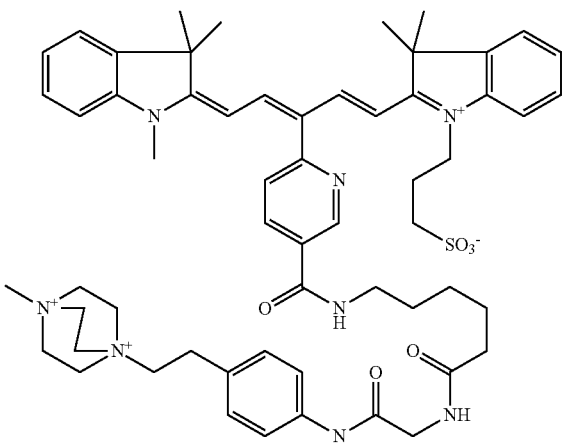 | 3-(3,3-dimethyl-2-((1E,3Z,5E)-3-(5-((6-((2-((4-(2-(4-methyl-1,4-diazabicyclo[2.2.2]octan-1,4-diium-1-yl)ethyl)phenyl)amino)-2-oxoethyl)amino)-6-oxohexyl)carbamoyl)pyridin-2-yl)-5-(1,3,3-trimethylindolin-2-ylidene)penta-1,3-dien-1-yl)-3H-indol-1-ium-1-yl)propane-1-sulfonate di-acetate |
| A8 | 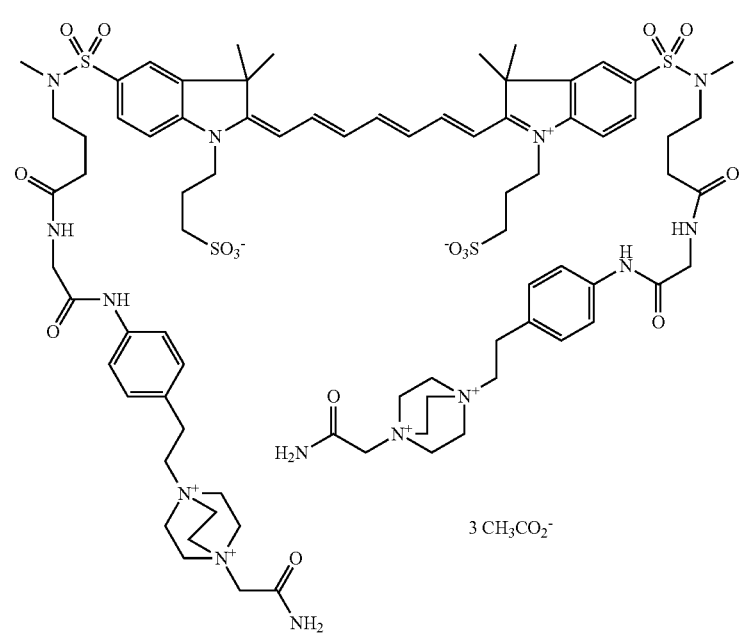 | 3-(5-(N-(4-((2-((4-(2-(4-(2-amino-2-oxoethyl)-1,4-diazabicyclo[2.2.2]octan-1,4-diium-1-yl)ethyl)phenyl)amino)-2-oxoethyl)amino)-4-oxobutyl)-N-methylsulfamoyl)-2-((1E,3E,5E,7E)-7-(5-(N-(4-((2-((4-(2-(4-(2-amino-2-oxoethyl)-1,4-diazabicyclo[2.2.2]octan-1,4-diium-1-yl)ethyl)phenyl)amino)-2-oxoethyl)amino)-4-oxobutyl)-N-methylsulfamoyl)-3,3-dimethyl-1-(3-sulfonatopropyl)indolin-2-ylidene)hepta-1,3,5-trien-1-yl)-3,3-dimethyl-3H-indol-1-ium-1-yl)propane-1-sulfonate tri-acetate |

TABLE 4-continued

| Compound No. | Chemical Structure | Chemical Name |
|---|---|---|
| A9 | 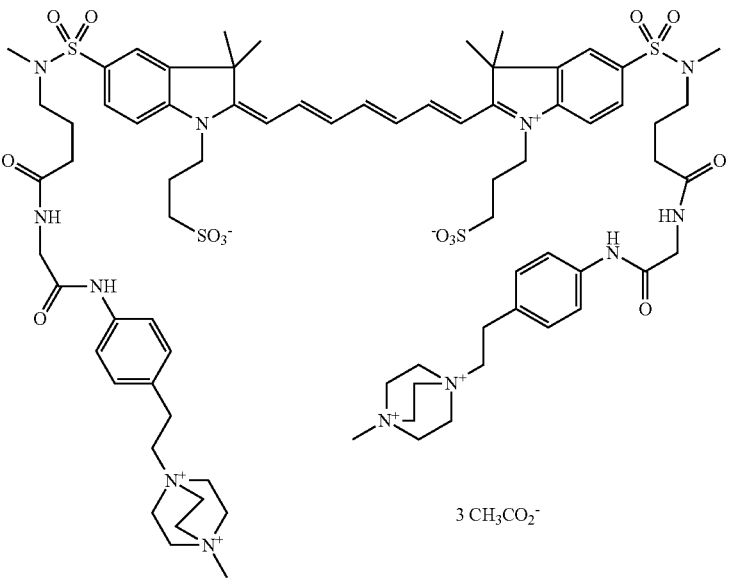 | 3-((E)-2-((2E,4E,6E)-7-(3,3-dimethyl-5-(N-methyl-N-(4-((2-((4-(2-(4-methyl-1,4-diazabicyclo[2.2.2]octan-1,4-diium-1-yl)ethyl)phenyl)amino)-2-oxoethyl)amino)-4-oxobutyl)sulfamoyl)-1-(3-sulfonatopropyl)-3H-indol-1-ium-2-yl)hepta-2,4,6-trien-1-ylidene)-3,3-dimethyl-5-(N-methyl-N-(4-((2-((4-(2-(4-methyl-1,4-diazabicyclo[2.2.2]octan-1,4-diium-1-yl)ethyl)phenyl)amino)-2-oxoethyl)amino)-4-oxobutyl)sulfamoyl)indolin-1-yl)propane-1-sulfonate tri-acetate |
| A10 | 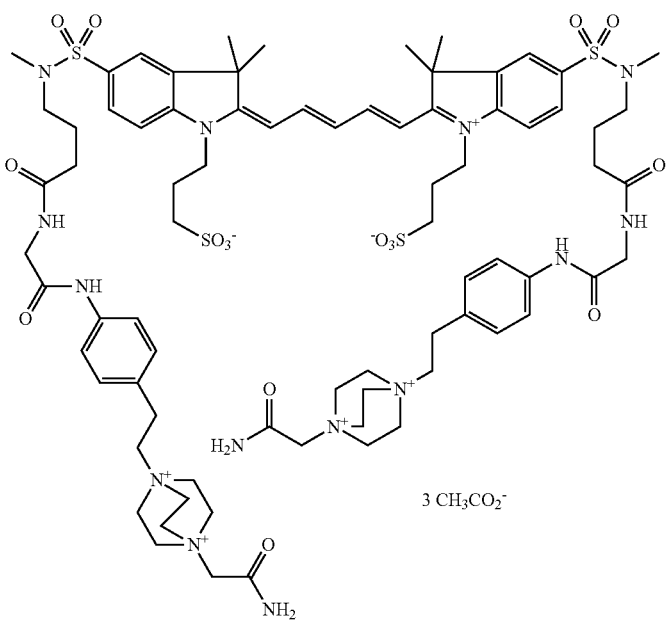 | 3-(5-(N-(4-((2-((4-(2-(4-(2-amino-2-oxoethyl)-1,4-diazabicyclo[2.2.2]octan-1,4-diium-1-yl)ethyl)phenyl)amino)-2-oxoethyl)amino)-4-oxobutyl)-N-methylsulfamoyl)-2-((1E,3E,5E)-5-(5-(N-(4-((2-((4-(2-(4-(2-amino-2-oxoethyl)-1,4-diazabicyclo[2.2.2]octan-1,4-diium-1-yl)ethyl)phenyl)amino)-2-oxoethyl)amino)-4-oxobutyl)-N-methylsulfamoyl)-3,3-dimethyl-1-(3-sulfonatopropyl)indolin-2-ylidene)penta-1,3-dien-1-yl)-3,3-dimethyl-3H-indol-1-ium-1-yl)propane-1-sulfonate tri-acetate |

TABLE 4-continued

| Compound No. | Chemical Structure | Chemical Name |
|---|---|---|
| A11 | 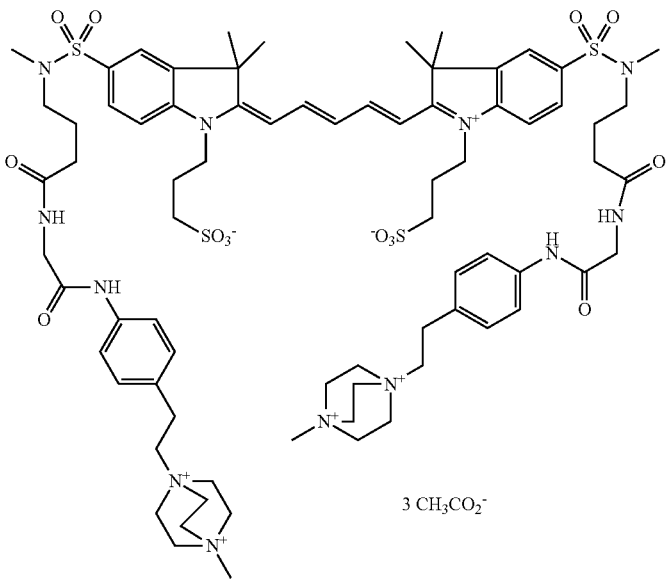 | 3-((E)-2-((2E,4E)-5-(3,3-dimethyl-5-(N-methyl-N-(4-((2-((4-(2-(4-methyl-1,4-diazabicyclo[2.2.2]octan-1,4-diium-1-yl)ethyl)phenyl)amino)-2-oxoethyl)amino)-4-oxobutyl)sulfamoyl)-1-(3-sulfonatopropyl)-3H-indol-1-ium-2-yl)penta-2,4-dien-1-ylidene)-3,3-dimethyl-5-(N-methyl-N-(4-((2-((4-(2-(4-methyl-1,4-diazabicyclo[2.2.2]octan-1,4-diium-1-yl)ethyl)phenyl)amino)-2-oxoethyl)amino)-4-oxobutyl)sulfamoyl)indolin-1-yl)propane-1-sulfonate tri-acetate |
| A12 | 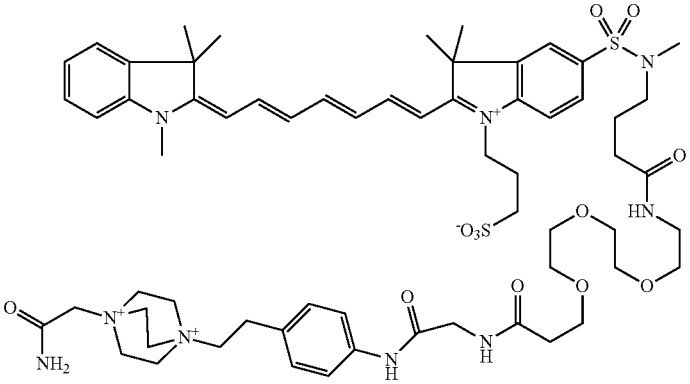 | 3-(5-(N-(1-((4-(2-(4-(2-amino-2-oxoethyl)-1,4-diazabicyclo[2.2.2]octan-1,4-diium-1-yl)ethyl)phenyl)amino)-1,4,17-trioxo-7,10,13-trioxa-3,16-diazaicosan-20-yl)-N-methylsulfamoyl)-3,3-dimethyl-2-((1E,3E,5E,7E)-7-(1,3,3-trimethylindolin-2-ylidene)hepta-1,3,5-trien-1-yl)-3H-indol-1-ium-1-yl)propane-1-sulfonate di-acetate |

The imaging agents disclosed herein can be formulated into a pharmaceutical composition suitable for administration to a subject, for example, an animal and/or a human. The pharmaceutical composition can include one or more imaging agents and one or more excipients, for example, a stabilizer in a physiologically relevant carrier.

For in vivo use, the compositions of the present invention can be provided in a formulation suitable for administration to a subject, for example, an animal or a human. Accordingly, the formulations include the agents together with a physiologically relevant carrier suitable for the desired form and/or dose of administration. The term, "physiologically relevant carrier" is understood to mean a carrier in which the agents are dispersed, dissolved, suspended, admixed and physiologically tolerable, i.e., can be administered to, in, or on the subject's body without undue discomfort, or irritation, or toxicity. The preferred carrier is a fluid, preferably a liquid, more preferably an aqueous solution; however, carriers for solid formulations, inhaled formulations, topical formulations, ophthalmic formulations, and transdermal formulations are also contemplated as within the scope of the invention.

It is contemplated that the agents can be administered orally or parenterally. For parenteral administration, the agents can be administered intravenously, intramuscularly, cutaneously, percutaneously, subcutaneously, rectally, nasally, vaginally, and ocularly. Thus, the composition may be in the form of, e.g., solid tablets, capsules, pills, powders including lyophilized powders, colloidal suspensions, microspheres, liposomes granulates, suspensions, emulsions, solutions, gels, including hydrogels, pastes, ointments, creams, plasters, irrigation solutions, drenches, osmotic delivery devices, suppositories, enemas, injectables, implants, sprays, or aerosols. The pharmaceutical compositions can be formulated according to conventional pharmaceutical practice (see, e.g., Remington: The Science and Practice of Pharmacy, 20th edition, 2000, ed. A. R. Germaro, Lippincott Williams & Wilkins, Philadelphia, and Encyclopedia of Pharmaceutical Technology, eds. J. Swarbrick and J. C. Boylan, 1988-1999, Marcel Dekker, New York).

It is understood that the formulation of the agents, the choice of mode of administration, the dosages of agents administered to the subject, and the timing between administration of the agents and imaging is within the level of skill in the art.

II. Applications

It is understood that bacterium targeting agents can be used in a variety of imaging and therapeutic applications.

A. General Imaging Methods

The present invention provides methods for in vitro and in vivo imaging using the imaging agents disclosed herein. For a review of optical imaging techniques, see, e.g., Alfano et al., *Ann. NY Acad. Sci.* 820:248-270 (1997); Weissleder, *Nature Biotechnology* 19, 316-317 (2001); Ntziachristos et al., *Eur. Radiol.* 13:195-208 (2003); Graves et al., *Curr. Mol. Med.* 4:419-430 (2004); Citrin et al., *Expert Rev. Anticancer Ther.* 4:857-864 (2004); Ntziachristos, Ann. Rev. Biomed. Eng. 8:1-33 (2006); Koo et al., *Cell Oncol.* 28:127-139 (2006); and Rao et al., *Curr. Opin. Biotechnol.* 18:17-25 (2007).

Optical imaging includes all methods from direct visualization without use of any device and use of devices such as various scopes, catheters and optical imaging equipment, for example computer based hardware for tomographic presentations. The imaging agents are useful with optical imaging modalities and measurement techniques including, but not limited to: endoscopy; fluorescence endoscopy; luminescence imaging; time resolved transmittance imaging; transmittance imaging; nonlinear microscopy; confocal imaging; acousto-optical imaging; photoacoustic imaging; reflectance spectroscopy; spectroscopy; coherence interferometry; interferometry; optical coherence tomography; diffuse optical tomography and fluorescence mediated molecular tomography (continuous wave, time domain frequency domain systems and early photon), and measurement of light scattering, absorption, polarization, luminescence, fluorescence lifetime, quantum yield, and quenching.

An imaging system useful in the practice of the invention typically includes three basic components: (1) an appropriate light source for inducing excitation of the imaging agent, (2) a system for separating or distinguishing emissions from light used for fluorophore excitation, and (3) a detection system. The detection system can be hand-held or incorporated into other useful imaging devices, such as intraoperative microscopes. Exemplary detection systems include an endoscope, catheter, tomographic system, hand-held imaging system, or an intraoperative microscope.

Preferably, the light source provides monochromatic (or substantially monochromatic) light. The light source can be a suitably filtered white light, i.e., bandpass light from a broadband source. For example, light from a 150-watt halogen lamp can be passed through a suitable bandpass filter commercially available from Omega Optical (Brattleboro, Vt.). Depending upon the system, the light source can be a laser. See, e.g., Boas et al., *Proc. Natl. Acad. Sci. USA* 91:4887-4891, 1994; Ntziachristos et al., *Proc. Natl. Acad. Sci. USA* 97:2767-2772, 2000; and Alexander, *J. Clin. Laser Med. Surg.* 9:416-418, 1991. Information on lasers for imaging can be found, for example, at Imaging Diagnostic Systems, Inc., Plantation, Fla. and various other sources. A high pass or bandpass filter can be used to separate optical emissions from excitation light. A suitable high pass or bandpass filter is commercially available from Omega Optical, Burlington, Vt.

In general, the light detection system can be viewed as including a light gathering/image forming component and a light/signal detection/image recording component. Although the light detection system can be a single integrated device that incorporates both components, the light gathering/image forming component and light detection/image recording component are discussed separately.

A particularly useful light gathering/image forming component is an endoscope. Endoscopic devices and techniques which have been used for in vivo optical imaging of numerous tissues and organs, including peritoneum (Gahlen et al., *J. Photochem. Photobiol. B* 52:131-135, 1999), ovarian cancer (Major et al., *Gynecol. Oncol.* 66:122-132, 1997), colon and rectum (Mycek et al., *Gastrointest. Endosc.* 48:390-394, 1998; and Stepp et al., *Endoscopy* 30:379-386, 1998), bile ducts (Izuishi et al., *Hepatogastroenterology* 46:804-807, 1999), stomach (Abe et al., *Endoscopy* 32:281-286, 2000), bladder (Kriegmair et al., *Urol. Int.* 63:27-31, 1999; and Riedl et al., *J. Endourol.* 13:755-759, 1999), lung (Hirsch et al., *Clin Cancer Res* 7:5-220, 2001), brain (Ward, *J. Laser Appl.* 10:224-228, 1998), esophagus, and head and neck regions can be employed in the practice of the present invention.

Other types of light gathering components are catheter-based devices, including fiber optics devices. Such devices are particularly suitable for intravascular imaging. See, e.g., Tearney et al., *Science* 276:2037-2039, 1997; and *Circulation* 94:3013, 1996.

Still other imaging technologies, including phased array technology (Boas et al., *Proc. Natl. Acad. Sci. USA* 91:4887-4891, 1994; Chance, *Ann. NY Acad. Sci.* 838:29-45, 1998), optical tomography (Cheng et al., *Optics Express* 3:118-123, 1998; and Siegel et al., *Optics Express* 4:287-298, 1999), intravital microscopy (Dellian et al., *Br. J. Cancer* 82:1513-1518, 2000; Monsky et al., *Cancer Res.* 59:4129-4135, 1999; and Fukumura et al., *Cell* 94:715-725, 1998), confocal imaging (Korlach et al., *Proc. Natl. Acad. Sci. USA* 96:8461-8466, 1999; Rajadhyaksha et al., J. Invest. Dermatol. 104:946-952, 1995; and Gonzalez et al., J. Med. 30:337-356, 1999) and fluorescence molecular tomography (FMT) (Nziachristos et al., *Nature Medicine* 8:757-760, 2002; U.S. Pat. No. 6,615,063, PCT WO 03/102558, and PCT WO 03/079015) can be used with the imaging agents of the invention. Similarly, the imaging agents can be used in a variety of imaging systems, for example, (1) the IVIS® Imaging Systems: 100 Series, 200 Series (Xenogen, Alameda, Calif.), (2) SPECTRUM and LUMINA (Xenogen, Alameda, Calif.), (3) the SoftScan® or the eXplore Optix™ (GE Healthcare, United Kingdom), (4) Maestro™ and Nuance™-2 Systems (CR1, Woburn, Mass.), (5) Image Station In-Vivo FX from Carestream Molecular Imaging, Rochester, N.Y. (formerly Kodak Molecular Imaging Systems), (6) OV100, IV100 (Olympus Corporation, Japan), (7) Cellvizio Mauna Kea Technologies, France), (8)] NanoSPECT/CT or HiSPECT (Bioscan, Washington, D.C.), (9) CTLM® or LILA™ (Imaging Diagnostic Systems, Plantation, Fla.), (10) DYNOT™ (NIRx Medical Technologies, Glen Head, N.Y.), and (11) NightOWL Imaging Systems by Berthold Technologies, Germany.

A variety of light detection/image recording components, e.g., charge coupled device (CCD) systems or photographic film, can be used in such systems. The choice of light detection/image recording depends on factors including the type of light gathering/image forming component being used. It is understood, however, that the selection of suitable components, assembling them into an optical imaging system, and operating the system is within ordinary skill in the art.

For agents that have magnetic properties, MRI imaging well known in the art can also be applied in the practice of the invention. For a review of MRI techniques see Westbrook, Handbook of MRI Technique, $2^{nd}$ Edition, 1999, Blackwell Science. It is possible that images obtained, for example, by optical imaging and by magnetic resonance imaging can be co-registered or fused with one another to provide additional information about the item being imaged. Furthermore, multi-modality imaging systems (i.e., combined optical and MR imaging systems) can be used to create combined optical MR images.

In addition, the compositions and methods of the present invention can be used for other imaging compositions and methods. For example, the agents of the present invention can be imaged by other imaging modalities, such as, X-ray, computed tomography (CT), MR imaging, ultrasound, positron emission tomography (PET), and single photon computerized tomography (SPECT).

In addition, the compositions and methods of the present invention can be used in combination with other imaging compositions and methods. For example, the agents of the present invention can be imaged by optical imaging protocols either alone or in combination with other traditional imaging modalities, such as, X-ray, computed tomography (CT), MR imaging, ultrasound, positron emission tomography (PET), and single photon computerized tomography (SPECT). For instance, the compositions and methods of the present invention can be used in combination with CT or MRI to obtain both anatomical and molecular information simultaneously, for example, by co-registration of with an image generated by another imaging modality. The compositions and methods of the present invention can also be used in combination with X-ray, CT, PET, ultrasound, SPECT and other optical and MR contrast agents or alternatively, the agents of the present invention may also include imaging agents, such as iodine, gadolinium atoms and radioactive isotopes, which can be detected using CT, PET, SPECT, and MR imaging modalities in combination with optical imaging. The imaging agents can be linked to or incorporated in the agents.

(i) In Vivo Imaging Methods

With respect to optical in vivo imaging, such a method comprises (a) administering to a subject one or more of the bacterium targeting agents described herein, (b) allowing sufficient time to permit the agent to distribute with the subject, and (c) detecting a signal emitted by the bacterium targeting agent. The signal emitted by the agent can be used to construct an image, for example, a tomographic image. The foregoing steps can be repeated at predetermined time intervals thereby to permit evaluation of the emitted signals of the bacterium targeting agents in the subject over time.

In another in vivo imaging method the method comprises (a) administering to a subject one or more of the bacterium targeting agents described herein that contains a fluorochrome; (b) allowing sufficient time to permit the bacterium targeting agent to distribute within the subject; (c) exposing the subject to light of a wavelength absorbable by the fluorochrome, and (d) detecting a signal emitted by the bacterium targeting agent. The foregoing steps can be repeated at predetermined time intervals thereby to permit evaluation of the emitted signals of the bacterium targeting agents in the subject over time. The illuminating and/or detecting steps (steps (c) and (d), respectively) can be performed using an endoscope, catheter, tomographic system, planar system, handheld imaging system, goggles, or an intraoperative microscope.

Before or during these steps, a detection system can be positioned around or in the vicinity of a subject (for example, an animal or a human) to detect signals emitted from the subject. The emitted signals can be processed to construct an image, for example, a tomographic image. In addition, the processed signals can be displayed as images either alone or as fused (combined) images.

In addition, it is possible to practice an in vivo imaging method that selectively detects and images one, two or more molecular imaging probes, including the bacterium targeting agents simultaneously. In such an approach, for example, in step (a) noted above, two or more imaging probes whose signal properties are distinguishable from one another are administered to the subject, either at the same time or sequentially, wherein at least one of the molecular imaging probes is a bacterium targeting agent. The use of multiple probes permits the recording of multiple biological processes, functions or targets.

The subject may be a vertebrate, for example, a mammal, for example, a human. The subject may also be a non-vertebrate (for example, *C. elegans, drosophila*, or another model research organism, etc.) used in laboratory research.

Information provided by such in vivo imaging approaches, for example, the presence, absence, or level of emitted signal can be used to detect and/or monitor a disease in the subject. Exemplary diseases include, without limitation, autoimmune disease, bone disease, cancer, cardiovascular disease, environmental disease, dermatological disease, immunologic disease, inherited disease, infectious disease, metabolic disease, neurodegenerative disease, ophthalmic disease, and respiratory disease. In addition, in vivo imaging can be used to assess the effect of a compound or therapy by using the imaging agents, wherein the subject is imaged prior to and after treatment with the compound or therapy, and the corresponding signal/images are compared.

The bacterium targeting agents also can be used in in vivo imaging method where cells labeled with the bacterium targeting agent are administered to the recipient. The cells can be labeled with the bacterium targeting agents either in vivo or ex vivo. In the ex vivo approach, cells can be derived directly from a subject or from another source (e.g., from another subject, cell culture, etc.). The bacterium targeting agents can be mixed with the cells to effectively label the cells and the resulting labeled cells administered to the subject into a subject in step (a). Steps (b)-(d) then are followed as described above. This method can be used for monitoring trafficking and localization of certain cell types, including T-cells, tumor cells, immune cells and stem cells, and other cell types. In particular, this method may be used to monitor cell-based therapies.

It is understood that the formulation of the bacterium targeting agents, the choice of mode of administration, the dosages of bacterium targeting agents administered to the subject, and the timing between administration of the bacterium targeting agents and imaging is within the level of skill in the art.

The foregoing methods can be used to determine a number of indicia, including tracking the localization of the bacterium targeting agent in the subject over time or assessing changes or alterations in the metabolism and/or excretion of the bacterium targeting agent in the subject over time. The methods can also be used to follow therapy for such diseases by imaging molecular events and biological pathways modulated by such therapy, including but not limited to determining efficacy, optimal timing, optimal dosing levels (including for individual patients or test subjects), and synergistic effects of combinations of therapy.

The methods and compositions of the invention can be used to help a physician or surgeon to identify and characterize areas of disease, such as infection and cell death, to distinguish diseased and/or infectious tissues from normal tissues, such as detecting specific regions of bacterial infection within an organ or other tissues that are difficult to detect using ordinary imaging techniques, and to further assess said tissues as candidates for particular treatment regimens, or gauge the prognosis such as likelihood of sepsis. Additionally, the methods and compositions can be used to image sites undergoing increased apoptosis—as evidenced by endogenous, non-infectious cells with elevated positively charged cell surfaces.

The methods and compositions of the invention can also be used in the detection, characterization and/or determination of the localization of a disease, including early disease, the severity of a disease or a disease-associated condition, the staging of a disease, and/or monitoring a disease. The presence, absence, or level of an emitted signal can be indicative of a disease state.

The methods and compositions of the invention can also be used to monitor and/or guide various therapeutic interventions, such as surgical procedures, and monitoring drug therapy, including cell based therapies. The methods described herein can also be used to assess therapeutic efficacy of various treatment regimens, including but not limited to those designed to reduce tumor acidosis and metastasis or various radiotherapeutics. The methods of the invention can also be used in prognosis of a disease or disease condition.

With respect to each of the foregoing, examples of such disease or disease conditions that can be detected or monitored (before, during or after therapy) include inflammation (for example, inflammation caused by arthritis, for example, rheumatoid arthritis), cancer (for example, colorectal, ovarian, lung, breast, prostate, cervical, testicular, skin, brain, gastrointestinal, pancreatic, liver, kidney, bladder, stomach, leukemia, mouth, esophageal, bone), cardiovascular disease (for example, atherosclerosis and inflammatory conditions of blood vessels, ischemia, stroke, thrombosis, disseminated intravascular coagulation), dermatologic disease (for example, Kaposi's Sarcoma, psoriasis, allergic dermatitis), ophthalmic disease (for example, macular degeneration, diabetic retinopathy), infectious disease (for example, bacterial, viral, fungal and parasitic infections, including Acquired Immunodeficiency Syndrome, Malaria, Chagas Disease, Schistosomiasis), immunologic disease (for example, an autoimmune disorder, lymphoma, multiple sclerosis, rheumatoid arthritis, diabetes mellitus, lupus erythematosis, myasthenia gravis, Graves disease), central nervous system disease (for example, a neurodegenerative disease, such as Parkinson's disease or Alzheimer's disease, Huntington's Disease, amyotrophic lateral sclerosis, prion disease), inherited diseases, metabolic diseases, environmental diseases (for example, lead, mercury and radioactive poisoning, skin cancer), bone-related disease (for example, osteoporosis, primary and metastatic bone tumors, osteoarthritis), neurodegenerative disease, and surgery-related complications (such as graft rejection, organ rejection, alterations in wound healing, fibrosis or other complications related to surgical implants).

The methods and compositions described herein can, therefore, be used, for example, to detect and/or quantify the presence and/or localization of elevated positively charged cell surfaces in a subject, including humans, for instance in infectious or apoptotic cells, and to detect and/or quantify the presence and/or localization of infection and cell death, including the presence of infectious or apoptotic areas within an organ. The methods and compositions described herein can also be used to detect and/or quantify bacteria and apoptosis associated with diseases, disorders and conditions, including but not limited to preneoplastic/neoplastic disease including areas at risk for acute occlusion (i.e., vulnerable plaques) in coronary and peripheral arteries, regions of expanding aneurysms, unstable plaque in carotid arteries, and ischemic areas. The methods and compositions of the invention can also be used in identification and evaluation of cell death, injury, apoptosis, necrosis, and hypoxia. The methods and compositions can also be used for drug delivery and to monitor drug delivery, especially when drugs or drug-like molecules are chemically attached to the fluorescent probes. Exemplary drug molecules include chemotherapeutic and cytostatic agents and photodynamic agents including but not limited to Photofrin, Lutrin, Antrin, aminolevulinic acid, hypericin, benzoporphyrin derivative, and porphyrins.

In addition, the methods and compositions described herein can be used to image bacterial infection in a subject. The method comprises administering to a subject (for example, a human or animal) an amount of one or more of the bacterium targeting agents described herein sufficient to facilitate bacterial imaging. After sufficient time to permit the agent to distribute within the animal or distribute within the area to be imaged, the presence and/or amount of the agent is determined. The presence and/or amount of the agent can then be used to create an image, for example, a tomographic image, representative of elevated positively charged cell surfaces within the tissues of the subject.

In addition, the methods and compositions described herein can be used to image bacterial infections in a subject such as tuberculosis, Lyme disease, brucellosis, whooping cough, pneumonia, tetanus, diphtheria, typhoid fever, meningitis, cellulitis, impetigo, botulism, psittacosis, urethritis, enteritis, colitis, anthrax, Legionnaire's Disease, syphilis, tularemia, bronchitis, ulcers, boils, leptospirosis, listeriosis, gonorrhea, shigellosis, salmonellosis, cholera, cystitis, septicemia, txinoses, endocarditis, necrotizing pneumonia, toxic shock syndrome, scarlet fever, rheumatic fever, necrotizing fascitis, and Rocky Mountain Spotted Fever.

(ii) In Vitro Imaging Methods

With respect to in vitro imaging, the imaging agents can be used in a variety of in vitro assays. For example, an exemplary in vitro imaging method comprises: (a) contacting a sample, for example, a biological sample, with one or more of the bacterium targeting agents described herein; (b) allowing the agent(s) to interact with a biological target in the sample; (c) optionally, removing unbound agent; and (d) detecting a signal emitted from the agent thereby to determine whether the agent has been activated by or bound to the biological target. When the bacterium targeting agent comprises a fluorochrome, step (d) further comprises illuminating the sample with light of a wavelength absorbable by the fluorochrome to produce the emitted signal.

After an agent has been designed, synthesized, and optionally formulated, it can be tested in vitro by one skilled in the art to assess its biological and performance characteristics. For instance, different types of cells grown in culture can be used to assess the biological and performance characteristics of the agent. Cellular uptake, binding or cellular localization of the agent can be assessed using techniques known in the art, including, for example, fluorescent microscopy, FACS analysis, immunohistochemistry, immunoprecipitation, in situ hybridization and Forster resonance energy transfer (FRET) or fluorescence resonance energy transfer. By way of example, the agents can be contacted with a sample for a period of time and then washed to remove any free agents. The sample can then be viewed using an appropriate detection device such as a fluorescent microscope equipped with appropriate filters matched to the optical properties of a fluorescent agent. Fluorescence microscopy of cells in culture or scintillation counting is also a convenient means for determining whether uptake and binding has occurred. Tissues, tissue sections and other types of samples such as cytospin samples can also be used in a similar manner to assess the biological and performance characteristics of the agents. Other detection methods including, but not limited to flow cytometry, immunoassays, hybridization assays, and microarray analysis can also be used.

B. Exemplary Imaging Methods

One aspect of the invention provides a method of in vivo imaging, the method comprising: (a) administering to a subject a compound described herein (such as a bacterium imaging agent); (b) allowing the agent to distribute within the subject; and (c) detecting a signal emitted by the bacterium imaging agent.

Another aspect of the invention provides a method of in vivo optical imaging, the method comprising: (a) administering to a subject a a compound described herein (such as a bacterium imaging agent), wherein the agent comprises a fluorochrome; (b) allowing the agent to distribute within the subject; (c) exposing the subject to light of a wavelength absorbable by the fluorochrome; and (d) detecting a signal emitted by the agent.

Another aspect of the invention provides a method of in vivo imaging, wherein the signal emitted by the agent is used to construct an image. In other embodiments, the image is a tomographic image. In certain embodiments, the invention is a method of in vivo optical imaging, wherein steps (a)-(c) are repeated at predetermined time intervals thereby to permit evaluation of the emitted signals of the bacterium targeting agent in the subject over time. In certain embodiments, the invention is a method of in vivo optical imaging, wherein steps (a)-(d) are repeated at predetermined time intervals thereby to permit evaluation of the emitted signals of the bacterium targeting agents in the subject over time. In certain embodiments, the invention is a method of in vivo imaging, wherein the subject is an animal or a human. In certain embodiments, the invention is a method of in vivo imaging, wherein in step (a) two or more imaging probes whose signal properties are distinguishable from one another are administered to a subject, wherein at least one of the imaging probes is a bacterium targeting agent. In certain embodiments, the invention is a method of in vivo optical imaging, wherein the illuminating and detecting steps are performed using an endoscope, catheter, tomographic system, hand-held optical imaging system, or an intraoperative microscope.

Another aspect of the invention provides a method of in vivo imaging, wherein the presence, absence, or level of emitted signal is indicative of a disease state. In certain embodiments, the invention is a method of in vivo imaging, wherein the method is used to detect and/or monitor a disease. In certain embodiments, the disease is selected from the group consisting of bone disease, cancer, cardiovascular disease, environmental disease, dermatological disease, immunologic disease, inherited disease, infectious disease, inflammatory disease, metabolic disease, ophthalmic disease, and respiratory disease.

Another aspect of the invention provides a method of in vivo imaging, wherein, in step (a), cells labeled a compound described herein (such as a bacterium targeting agent) are administered to the subject. In other embodiments, the signal emitted by the agent is used to monitor trafficking and localization of the cells.

Another aspect of the invention provides a method of imaging bacterium infection in a subject, the method comprising the steps of: (a) administering an agent to a subject; and (b) detecting the presence of the agent thereby to produce an image representative of bacterium infection. In certain embodiments, the invention is a method of treating a disease in a subject comprising administering to a subject, either systemically or locally, an agent, wherein the agent comprises a radiolabel that localizes in the disease area and delivers an effective dose of radiation.

Another aspect of the invention provides an in vitro imaging method, the method comprising: (a) contacting a sample with an agent; (b) allowing the agent to bind to a biological target; (c) optionally removing unbound agent; and (d) detecting signal emitted from the agent thereby to determine whether the agent has been activated by or bound to the biological target. In other embodiments, the sample is a biological sample.

In certain embodiments, the chemical modifying groups comprise a biologically active molecule, such as a drug or a radiotherapeutic moiety. In certain embodiments the biologically active molecule is linked to the agent through a linker that is cleavable through a biological or physical mechanism including but not limited to enzymatic, thermal, acid catalyzed or photochemical cleavage.

In certain preferred embodiments, Q can be selected from a group consisting of (i) a substituted or unsubstituted aryl, (ii) a functionalized, substituted or unsubstituted heteroaryl, (iii) a functionalized, substituted or unsubstituted $C_1$-$C_{18}$ alkyl, alkenyl, alkynyl, alkoxy, or thioalkyl group. In other embodiments, Q is absent.

In certain embodiments, the chemical modifying moiety, M enhances the binding selectivity of the bacterium targeting agent for negatively-charged bacterial and apoptotic cell surfaces over other negatively-charged endogenous cell surfaces.

In certain embodiments, the chemical modifying moiety, M reduces the nonspecific cell membrane permeability of the bacterium targeting agent. Furthermore, in other embodiments, the chemical modifying moiety, M reduces the nonspecific tissue accumulation of the bacterium targeting agent when administered to a live animal.

In one aspect of the invention, bacterium targeting agents are fluorescent in the far-red or near-infrared spectral range.

In certain embodiments, the bacterium targeting agent further comprises one or more chemical modifiers, independently, chemically linked to the DABCO, L, and/or F or any combination thereof.

C. Therapeutic Applications

Certain of the bacterium targeting agents described herein, for example, agents containing a radiolabel and drug molecule, can be used to ameliorate a symptom of, or treat, a particular disease or disorder. The method comprises (a) administering an amount of one or more the agents described herein sufficient to impart a therapeutic effect in the subject; and (b) permitting sufficient time for the agent to distribute within the subject or otherwise localize in a region of the subject to be treated and then, (c) depending on the therapeutic agent, optionally activating the agent to impart a therapeutic effect. For example, when the therapeutic agent is a radiolabel, no subsequent activation is required. However, when the therapeutic agent is a photoreactive agent, for example, a dye used in photodynamic therapy, the agent may be activated by exposing the agent to light having a wavelength that activates the agent. As a result, the agents can be used to treat a condition of interest, for example, a cancer, immune disorder, inflammatory disorder, vascular disorder and the like. Furthermore the agents can be used to inhibit infection in an organ, or other region of interest in the subject, or reduce bacterial and apoptotic cell proliferation within a subject.

The invention will now be illustrated by means of the following examples, which are given for the purpose of illustration only and without any intention to limit the scope of the present invention.

III. Pharmaceutical Compositions

Agents described herein may be formulated with one or more pharmaceutically acceptable carriers (additives) and/or diluents to provide a pharmaceutical composition. Exemplary pharmaceutical compositions comprise one or more agents and one or more pharmaceutically acceptable carriers. As described in detail below, the pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically-acceptable carriers include a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Pharmaceutical compositions of this invention suitable for parenteral administration comprise one or more agents of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

In certain embodiments, the invention provides a pharmaceutically acceptable composition suitable for administration to a subject comprising a bacterium imaging agent and a pharmaceutically acceptable excipient.

IV. Definitions

To facilitate an understanding of the present invention, a number of terms and phrases are defined below.

The terms "a," "an" and "the" as used herein mean "one or more" and include the plural unless the context is inappropriate.

As used herein, the term "effective amount" refers to the amount of a compound sufficient to effect beneficial or desired results. Unless stated otherwise, an effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the terms "patient" and "subject" refer to organisms to be subjected to, or treated by, the methods of the present invention. Such organisms preferably include, but are not limited to, mammals (e.g., murines, simians, equines, bovines, porcines, canines, felines, and the like), and most preferably includes humans.

Certain compounds described herein may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

The term "affinity" as used herein, refers to the ability of the bacterium targeting agent to bind to and/or be retained by a negatively charged cell.

As used herein, the term "functionality" is understood to mean a reactive functional group that can be further modified or derivatized with another molecule. In one aspect, the reactive functional group is an amine, carboxylic acid, carboxylic ester, halogen, hydrazine, hydroxylamine, nitrile, isonitrile, isocyanate, isothiocyanate, thiol, maleimide, azide, alkyne, tetrazolyl, phosphonate, alkene, nitro, and nitroso.

The term "alkyl" is art-recognized, and includes saturated aliphatic groups, including straight-chain alkyl groups, and branched-chain alkyl groups. Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. In certain embodiments, the alkyl is unsubstituted.

The term "alkylene" refers to a diradical of an alkyl group. Exemplary alkylene groups include —CH$_2$— and —CH$_2$CH$_2$.

The term "heteroalkyl" is art-recognized and refers to saturated aliphatic groups, including straight-chain alkyl groups, and branched-chain alkyl groups where one of the backbone carbon atoms has been replaced with a heteroatom, such as O, S, or N. Exemplary heteroalkyl groups include —CH$_2$—O—CH$_3$ and —CH$_2$CH$_2$—O—CH$_3$.

The term "heteroalkylene" refers to a diradical of an heteroalkyl group. Exemplary heteroalkylene groups include —CH$_2$—O—CH$_2$— and —CH$_2$CH$_2$—O—CH$_2$—.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The term "arylene" as used herein refers to a divalent radical of an aromatic group. Arylene may be optionally substituted as described for aryl, or as otherwise indicated. An exemplary arylene group is

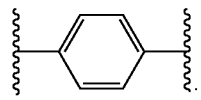

As used herein, the terms "heterocyclic" and "heterocyclyl" refer to an aromatic or nonaromatic ring containing one or more heteroatoms. The heteroatoms can be the same or different from each other. Examples of heteratoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic (or heterocyclyl) ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, aryl or heteroaryl moieties, —CF$_3$, —CN, or the like.

The terms "amine" and "amino" are art-recognized and refer to both unsubstituted and substituted amines, e.g., a moiety that may be represented by the general formulas:

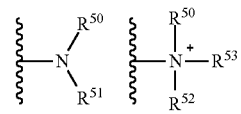

wherein $R^{50}$, $R^{51}$, $R^{52}$ and $R^{53}$ each independently represent a hydrogen, an alkyl, an alkenyl, —(CH$_2$)$_m$—$R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —(CH$_2$)$_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "substituted" refers to a group in which one or more hydrogen atoms are independently replaced with the same or different substituent(s). Exemplary substituents include, but are not limited to, halogen, alkyl, haloalkyl, oxo, alkoxyl, thiol, thioether, cyano, ester, ketone, amide, sulfonamide, carboxylate, carboxylic acid, aryl, aralkyl, alkenyl, alkynyl, alkylene-amide, etc.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

V. Examples

The compounds of the present invention can be synthesized from readily available starting materials following standard methods and procedures. The following non-limiting examples demonstrate the synthesis of exemplary fluorescent bacterium targeting agents. Representative materials and methods that may be used in preparing the materials of the invention are described further below. Unless otherwise stated, all chemicals and solvents (reagent grade) are used as commercially obtained without further purification. Synthesized compounds are characterized and purified by HPLC.

The synthesis of binding moieties are shown in the following scheme.

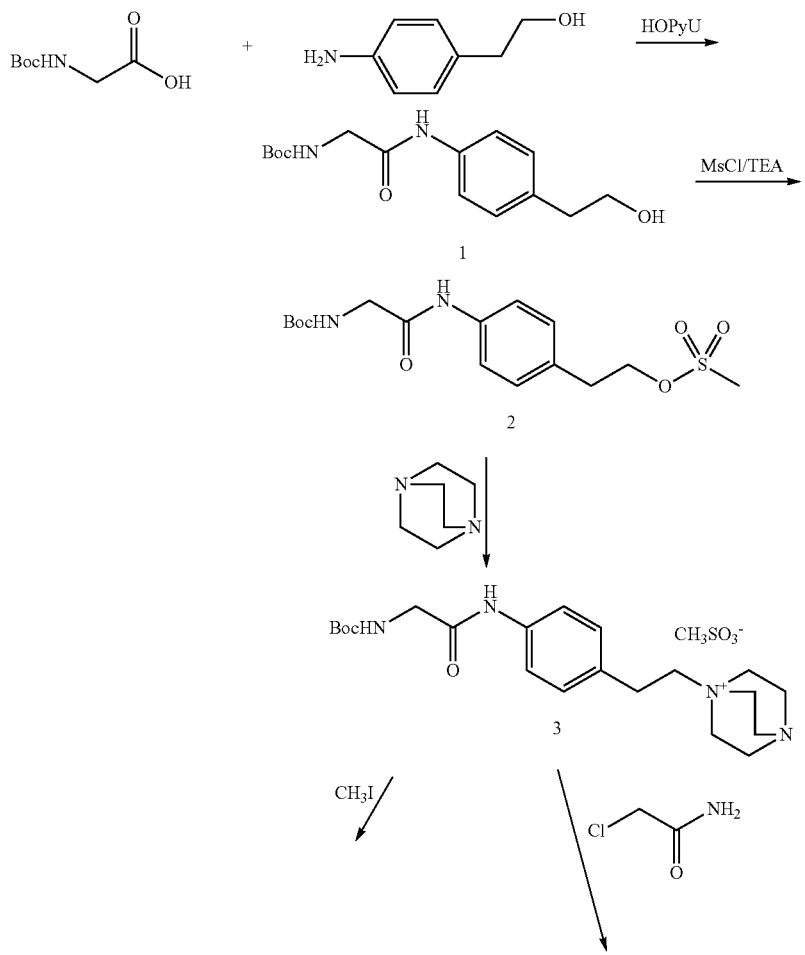

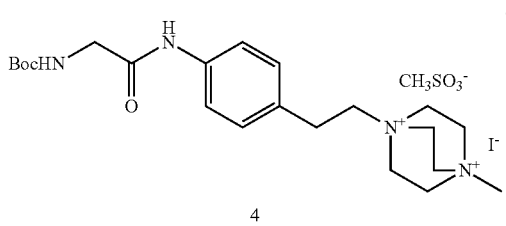

4

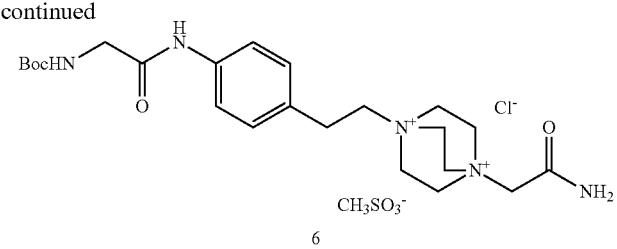

6

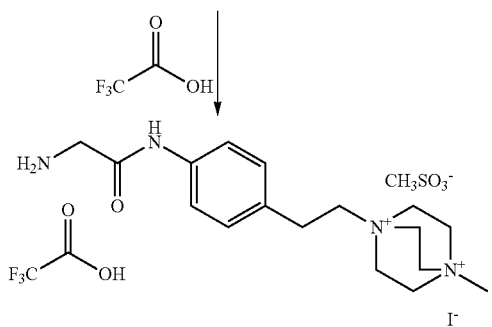

5

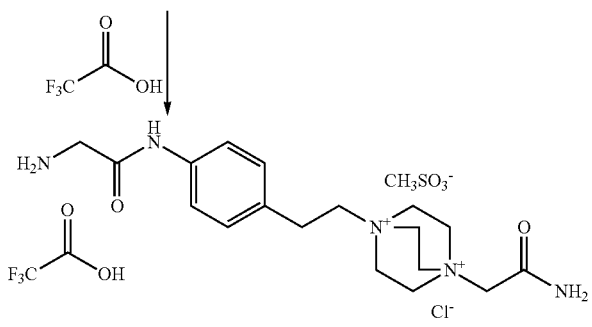

7

Intermediate 1

To the solution of Boc-glycine (770 mg, 4.4 mmol), 4-aminophenethyl alcohol (550 mg, 4.0 mmol), NEM (90 uL) in 20 mL of acetonitrile was added O-(2-oxo-[(2H)pyridyl)-N,N, N',N' tetramethyluronium tetrafluoborate (1.28 g, 4.4 mmol).

After 4 h, the solution was concentrated to ~0.5 mL and ethyl acetate (15 mL) was added, followed by 8 mL of 0.1 M aqueous $NaHCO_3$. The organic layer was washed with 5 mL of 0.1 M $naHCO_3$, and 2×5 mL of DI water. Evaporation to dryness afforded product 1 as an off-white solid.

Intermediate 2

To the slurry of 1 (120 mg, 0.4 mmol) in 3 mL dry MeCN, was added TEA (130 uL, 0.93 mmol) and the mixture was cooled in ice-bath. A solution of methanesulfonyl chloride (MsCl, 48 uL, 0.62 mmol) in 1.5 mL of dry MeCN (1.5 mL) was added slowly over 5 min and the mixture was warmed to ~20° C. after addition and aged for 1 h. MeCN was removed by speedvac and the residue was partitioned with 8 mL of ethyl acetate and 2 mL of 0.05 N aqueous HCl. The organic layer was washed with 2 mL of DI water, and 2×2 mL of saturated brine. After dried over anhydrous $Na_2SO_4$, the solution was evaporated to dryness to provide 2 as a solid.

Intermediate 3

To the solution of 2 (50 mg, 134 µmol) in 1 mL of MeCN was added DABCO (45 mg, 400 µmol) and the mixture was heated at ~60-70° C. for 6-8 h. The solution was concentrated to a thick oil by speedvac and dissolved in 1.5 mL of 1:9 MeCN/TEAA buffer (25 mM HOAc, 12.5 mM TEA). The crude was not completely soluble but could be loaded onto the resin as-is. After loaded to a short column of phenyl resin (~4 mL bed-volume), the resin was eluted with 10 mL of TEAA, collected as F-1, followed by 10 mL of 5:95 MeCN/TEAA (F-2), 10 mL of 10:90 MeCN/TEAA (F-3), 10 mL of 15:85 MeCN/TEAA (F-4), and 10 mL of 20/80 MeCN/TEAA (F-5). The fractions were analyzed by HPLC and F-2 and F-3 were combined and concentrated to dryness.

Intermediate 4

The intermediate 3 (53 mg, 118 µmol) was dissolved in 1 mL of DMF and methyl iodide (25 uL, 400 µmol) was added. The solution was aged at 20° C. for 40 min. The solution was concentrated to dryness. The solid was dissolved in 3 mL of DMF and split in to two parts (2 & 1 mL in glass test-tubes). Evaporation to dryness provided 4 as a gummy solid (70 mg and 29 mg respectively).

Intermediate 5

To a test-tube containing 70 mg of 4 (70 w %, 83 µmol) is added TFA (400 uL) and the mixture was mixed and aged at 20° C. for 20 min. The gummy solid turned into a slurry during the reaction. The mixture was diluted with 1 mL of MeCN and dried by speedvac, without heating, for ~20 min. The product was washed with 3×2 mL of MTBE by sonication/centrifugation and dried without heat for 10 min. The solid was dissolved in 1.9 mL of 0.1 N aqueous $NaHCO_3$ containing 100 µL of DMSO, and used to reaction with the fluorophore active ester immediately.

Intermediate 6

The intermediate 3 (50 mg, 110 µmol) was dissolved in 1 mL of DMF and 2-chloroacetamide (22 mg, 236 µmol) was added. The solution was heated at 70° C. for 16 h. The solution was diluted with 3 mL of acetonitrile and the product precipitated. The solid was washed with 3×2 mL acetonitrile and dried under vacuum.

Intermediate 7

To a test-tube containing 70 mg of 6 (20 mg) was added TFA (400 uL) and the mixture was mixed and aged at 20° C. for 20 min. The gummy solid turned into a slurry during the reaction. The mixture was diluted with 1 mL of MeCN and dried by speedvac, without heating, for ~20 min. The product was washed with 3×2 mL of MTBE by sonication/centrifugation and dried without heat for 10 min. The solid was dissolved in 1.9 mL of 0.1 N aqueous NaHCO$_3$ containing 100 µL of DMSO, and used to reaction with the fluorophore active ester immediately.

Syntheses of Bacterium Targeting Agents.

Method 1.

A solution of the fluorophore NHS ester (~4 µmol) in 1 mL of DMSO was added to a solution of DABCO-Me or DABCO-Amide (~20 µmol) in 1 mL of 0.1 M sodium bicarbonate. After 30 min, the solution was diluted with water and the product is isolated by loading the solution onto phenyl-resin (2 g), and eluted with a gradient of mixed aqueous triethylamine acetate (triethylamine: 12.5 mM, acetic acid: 25 mM) and acetonitrile (containing 12.5 mM of TEA and 25 mM of acetic acid, 10/90-50/50). Fraction of ~5 mL are collected and analyzed by HPLC.

Method 2.

To the solution of the fluorophore (~4 µmol) and DABCO-Me or DABCO-Amide (40 µmol) in 1:1 DMF/water (1 mL) containing 20 µL of N-ethylmorpholine was added O-(7-Azabenzotriazol-1-yl)-N,N,N',N'-tetramethyluronium hexafluorophosphate (20 µmol). After 2 h, the solution is diluted with 5 mL of water and loaded onto 2 g of phenyl resin. The resin is eluted with a gradient of mixed aqueous triethylamine acetate (triethylamine: 12.5 mM, acetic acid: 25 mM) and acetonitrile (containing 12.5 mM of TEA and 25 mM of acetic acid, 10/90-30/70).

Example 1

Synthesis of exemplary compound 3-((E)-2-((2E,4E,6E)-7-(5-(N-(4-((2-((4-(2-(4-(2-amino-2-oxoethyl)-1,4-diazabicyclo[2.2.2]octan-1,4-diium-1-yl)ethyl)phenyl)amino)-2-oxoethyl)amino)-4-oxobutyl)-N-methylsulfamoyl)-1,3,3-trimethyl-3H-indol-1-ium-2-yl)hepta-2,4,6-trien-1-ylidene)-3,3-dimethylindolin-1-yl)propane-1-sulfonate di-acetate—compound A1

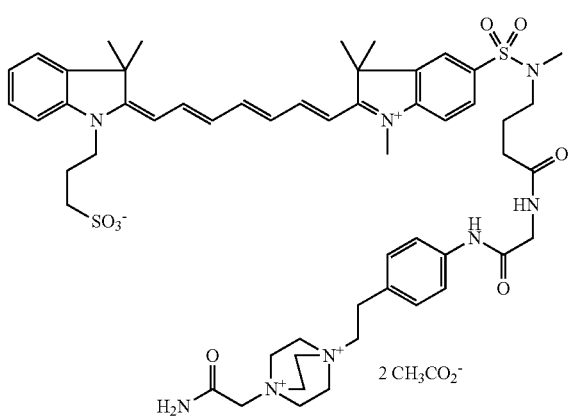

Compound A1 is prepared using Method 1. Fractions with >95% @ 750 nm are combined and dried to a solid.

Example 2

Synthesis of exemplary compound 3-((E)-2-((2E,4Z,6E)-7-(5-(N-(4-((2-((4-(2-(4-(2-amino-2-oxoethyl)-1,4-diazabicyclo[2.2.2]octan-1,4-diium-1-yl)ethyl)phenyl)amino)-2-oxoethyl)amino)-4-oxobutyl)-N-methylsulfamoyl)-1,3,3-trimethyl-3H-indol-1-ium-2-yl)-4-(methylthio)hepta-2,4,6-trien-1-ylidene)-3,3-dimethylindolin-1-yl)propane-1-sulfonate di-acetate—compound A2

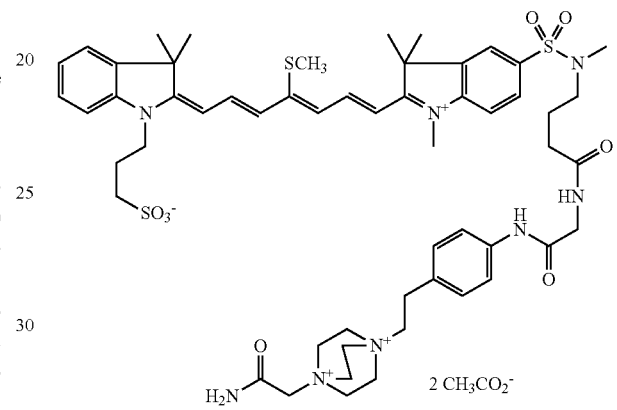

Compound A2 is prepared using Method 1. Fractions with >95% @ 750 nm are combined and dried to a solid.

Example 3

Synthesis of exemplary compound 1-(2-amino-2-oxoethyl)-4-(4-(2-(4-(N,1,3,3-tetramethyl-2-((1E,3E,5E,7E)-7-(1,3,3-trimethylindolin-2-ylidene)hepta-1,3,5-trien-1-yl)-3H-indol-1-ium-5-sulfonamido)butanamido)acetamido)phenethyl)-1,4-diazabicyclo[2.2.2]octane-1,4-diium tri-acetate—compound A3

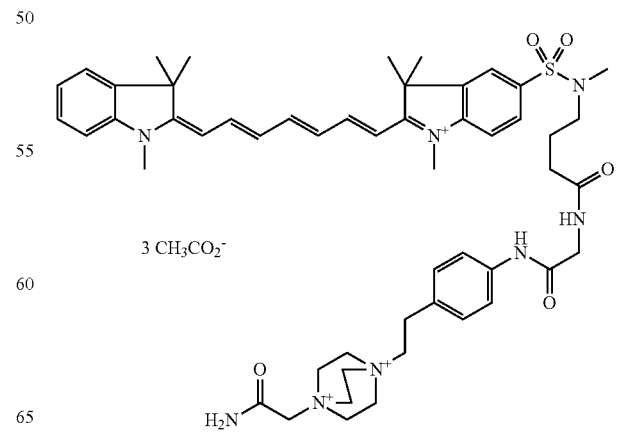

Compound A3 is prepared using Method 1. Fractions with >95% @ 750 nm are combined and dried to a solid.

Example 4

Synthesis of exemplary compound 3-(2-((1E,3Z,5E)-3-(5-((6-((2-((4-(2-(4-(2-amino-2-oxoethyl)-1,4-diazabicyclo[2.2.2]octan-1,4-diium-1-yl)ethyl)phenyl)amino)-2-oxoethyl)amino)-6-oxohexyl)carbamoyl)pyridin-2-yl)-5-(1,3,3-trimethylindolin-2-ylidene)penta-1,3-dien-1-yl)-3,3-dimethyl-3H-indol-1-ium-1-yl)propane-1-sulfonate di-acetate—compound A4

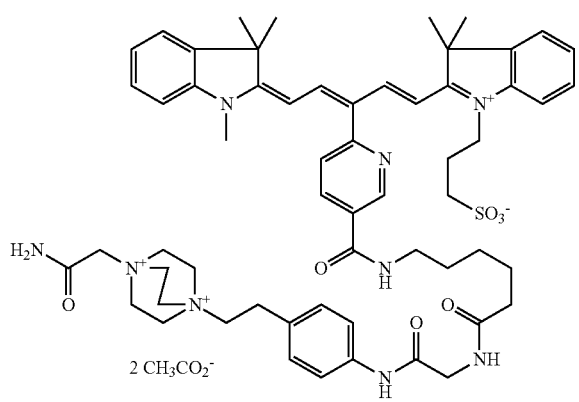

Compound A4 is prepared using Method 2. Fractions with >95% @ 750 nm are combined and dried to a solid.

Example 5

Synthesis of exemplary compound 3-(3,3-dimethyl-5-(N-methyl-N-(4-((2-((4-(2-(4-methyl-1,4-diazabicyclo[2.2.2]octan-1,4-diium-1-yl)ethyl)phenyl)amino)-2-oxoethyl)amino)-4-oxobutyl)sulfamoyl)-2-01E,3E,5E,7E)-7-(1,3,3-trimethylindolin-2-ylidene)hepta-1,3,5-trien-1-yl)-3H-indol-1-ium-1-yl)propane-1-sulfonate di-acetate—compound A5

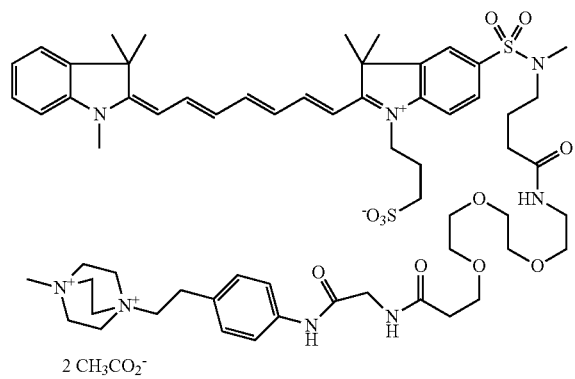

Compound A5 is prepared using Method 1. Fractions with >95% @ 750 nm are combined and dried to a solid.

Example 6

Synthesis of exemplary compound 3-(3,3-dimethyl-2-((E)-3-((E)-(1,3,3-trimethyl-5-(N-methyl-N-(4-((2-((4-(2-(4-methyl-1,4-diazabicyclo[2.2.2]octan-1,4-diium-1-yl)ethyl)phenyl)amino)-2-oxoethyl)amino)-4-oxobutyl)sulfamoyl)indolin-2-ylidene)methyl)cyclopent-2-en-1-ylidene)methyl)-3H-indol-1-ium-1-yl)propane-1-sulfonate di-acetate—compound A6

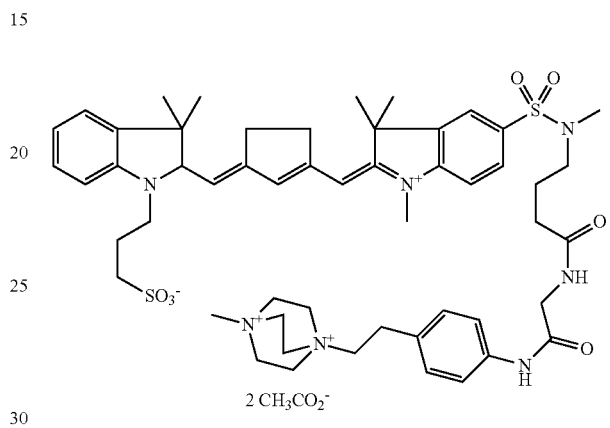

Compound A6 is prepared using Method 1. Fractions with >95% @ 650 nm are combined and dried to a solid.

Example 7

Synthesis of exemplary compound 3-(3,3-dimethyl-2-((1E,3Z,5E)-3-(5-((6-((2-((4-(2-(4-methyl-1,4-diazabicyclo[2.2.2]octan-1,4-diium-1-yl)ethyl)phenyl)amino)-2-oxoethyl)amino)-6-oxohexyl)carbamoyl)pyridin-2-yl)-5-(1,3,3-trimethylindolin-2-ylidene)penta-1,3-dien-1-yl)-3H-indol-1-ium-1-yl)propane-1-sulfonate di-acetate-compound A7

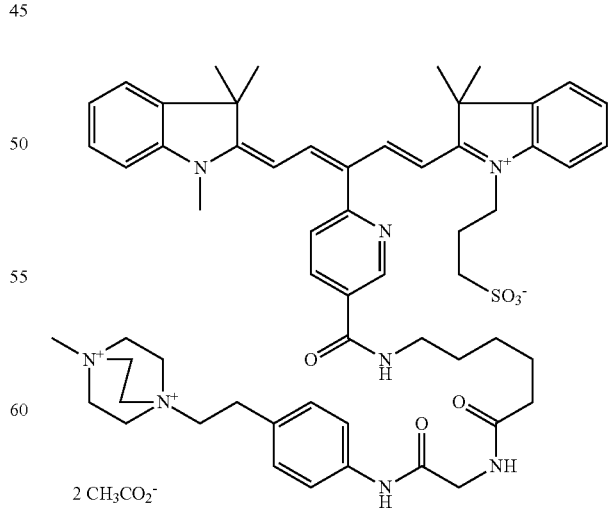

Compound A7 is prepared using Method 1. Fractions with >95% @ 635 nm are combined and dried to a solid.

Example 8

Synthesis of exemplary compound 3-(5-(N-(4-((2-((4-(2-(4-(2-amino-2-oxoethyl)-1,4-diazabicyclo[2.2.2]octan-1,4-diium-1-yl)ethyl)phenyl)amino)-2-oxoethyl)amino)-4-oxobutyl)-N-methylsulfamoyl)-2-01E,3E,5E,7E)-7-(5-(N-(4-((2-β4-(2-(4-(2-amino-2-oxoethyl)-1,4-diazabicyclo[2.2.2]octan-1,4-diium-1-yl)ethyl)phenyl)amino)-2-oxoethyl)amino)-4-oxobutyl)-N-methylsulfamoyl)-3,3-dimethyl-1-(3-sulfonatopropyl)indolin-2-ylidene)hepta-1,3,5-trien-1-yl)-3,3-dimethyl-3H-indol-1-ium-1-yl)propane-1-sulfonate triacetate—compound A8

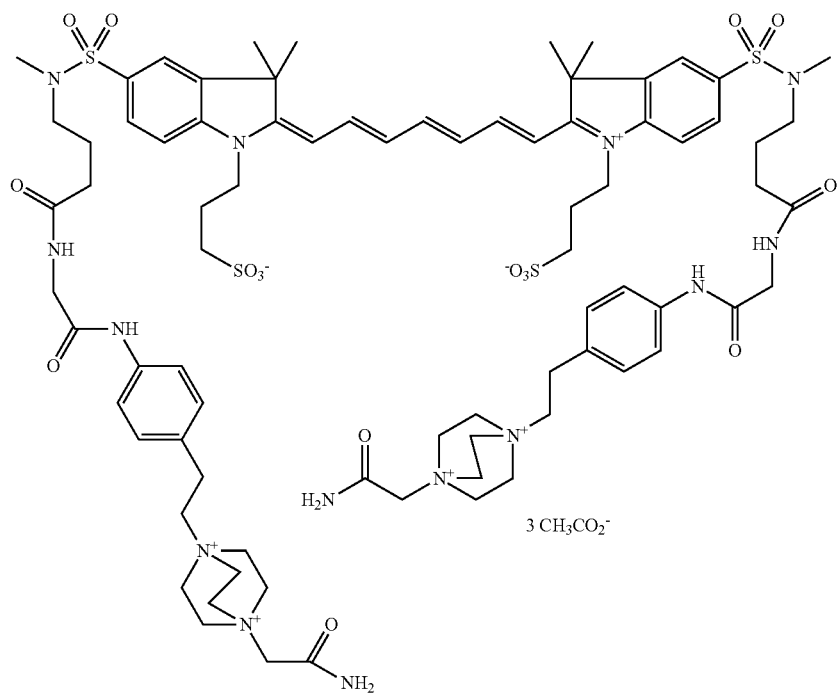

Compound A8 is prepared using Method 2. Fractions with >95% @ 750 nm are combined and dried to a solid.

Example 9

Synthesis of exemplary compound 3-((E)-2-((2E,4E,6E)-7-(3,3-dimethyl-5-(N-methyl-N-(4-((2-((4-(2-(4-methyl-1,4-diazabicyclo[2.2.2]octan-1,4-diium-1-yl)ethyl)phenyl)amino)-2-oxoethyl)amino)-4-oxobutyl)sulfamoyl)-1-(3-sulfonatopropyl)-3H-indol-1-ium-2-yl)hepta-2,4,6-trien-1-ylidene)-3,3-dimethyl-5-(N-methyl-N-(4-((2-((4-(2-(4-methyl-1,4-diazabicyclo[2.2.2]octan-1,4-diium-1-yl)ethyl)phenyl)amino)-2-oxoethyl)amino)-4-oxobutyl)sulfamoyl)indolin-1-yl)propane-1-sulfonate triacetate—compound A9

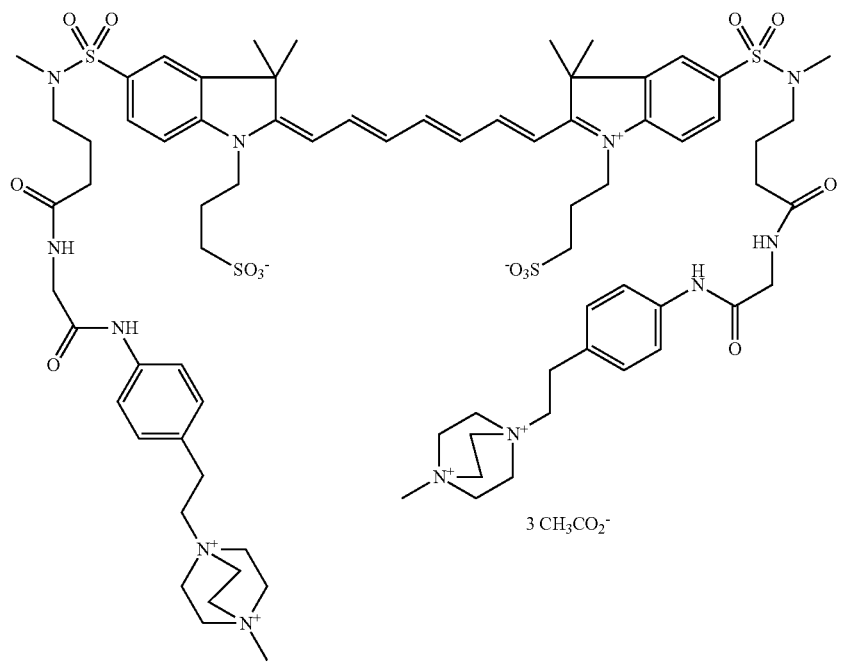

Compound A9 is prepared using Method 2. Fractions with >95% @ 750 nm are combined and dried to a solid.

Example 10

Synthesis of exemplary compound 3-(5-(N-(4-((2-((4-(2-(4-(2-amino-2-oxoethyl)-1,4-diazabicyclo[2.2.2]octan-1,4-diium-1-yl)ethyl)phenyl)amino)-2-oxoethyl)amino)-4-oxobutyl)-N-methylsulfamoyl)-2-01E,3E,5E)-5-(5-(N-(4-((2-((4-(2-(4-(2-amino-2-oxoethyl)-1,4-diazabicyclo[2.2.2]octan-1,4-diium-1-yl)ethyl)phenyl)amino)-2-oxoethyl)amino)-4-oxobutyl)-N-methylsulfamoyl)-3,3-dimethyl-1-(3-sulfonatopropyl)indolin-2-ylidene)penta-1,3-dien-1-yl)-3,3-dimethyl-3H-indol-1-ium-1-yl)propane-1-sulfonate tri-acetate—compound A10

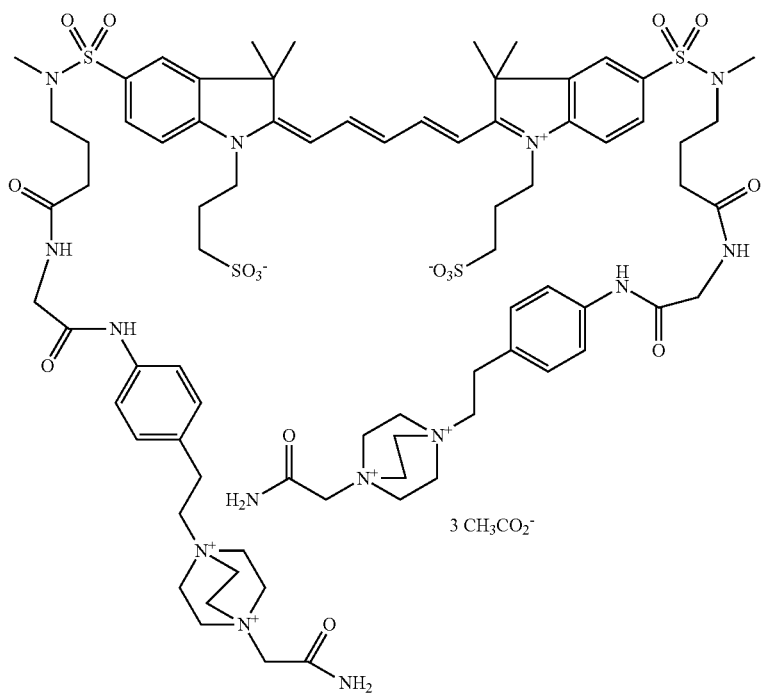

Compound A10 is prepared using Method 2. Fractions with >95% @ 635 nm are combined and dried to a solid.

Example 11

Synthesis of exemplary compound 3-((E)-2-((2E,4E)-5-(3,3-dimethyl-5-(N-methyl-N-(4-((2-((4-(2-(4-methyl-1,4-diazabicyclo[2.2.2]octan-1,4-diium-1-yl)ethyl)phenyl)amino)-2-oxoethyl)amino)-4-oxobutyl)sulfamoyl)-1-(3-sulfonatopropyl)-3H-indol-1-ium-2-yl)penta-2,4-dien-1-ylidene)-3,3-dimethyl-5-(N-methyl-N-(4-((2-((4-(2-(4-methyl-1,4-diazabicyclo[2.2.2]octan-1,4-diium-1-yl)ethyl)phenyl)amino)-2-oxoethyl)amino)-4-oxobutyl)sulfamoyl)indolin-1-yl)propane-1-sulfonate tri-acetate-compound A11

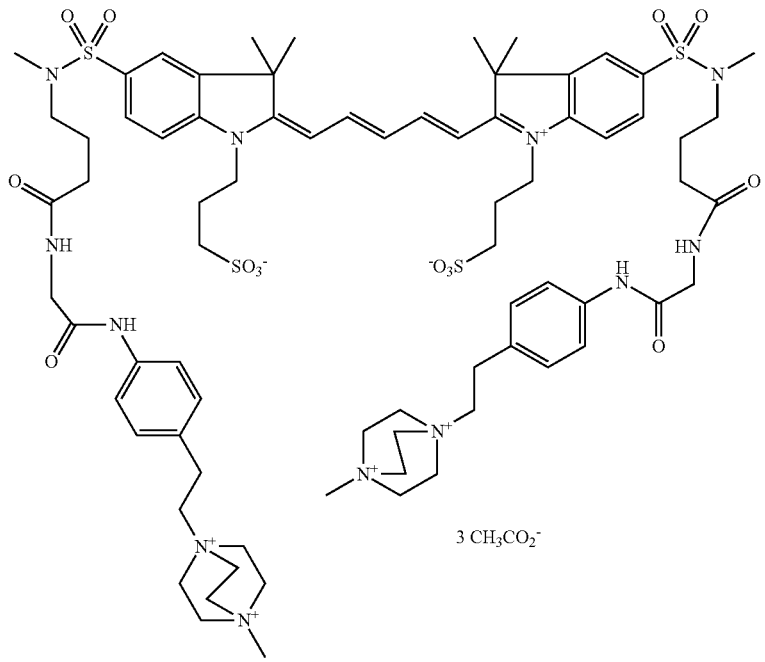

Compound A11 is prepared using Method 2. Fractions with >95% @ 635 nm are combined and dried to a solid.

Example 12

Synthesis of exemplary compound 3-(5-(N-(1-((4-(2-(4-(2-amino-2-oxoethyl)-1,4-diazabicyclo[2.2.2]octan-1,4-diium-1-yl)ethyl)phenyl)amino)-1,4,17-trioxo-7,10,13-trioxa-3,16-diazaicosan-20-yl)-N-methylsulfamoyl)-3,3-dimethyl-2-((1E,3E,5E,7E)-7-(1,3,3-trimethylindolin-2-ylidene)hepta-1,3,5-trien-1-yl)-3H-indol-1-ium-1-yl)propane-1-sulfonate diacetate—compound A12

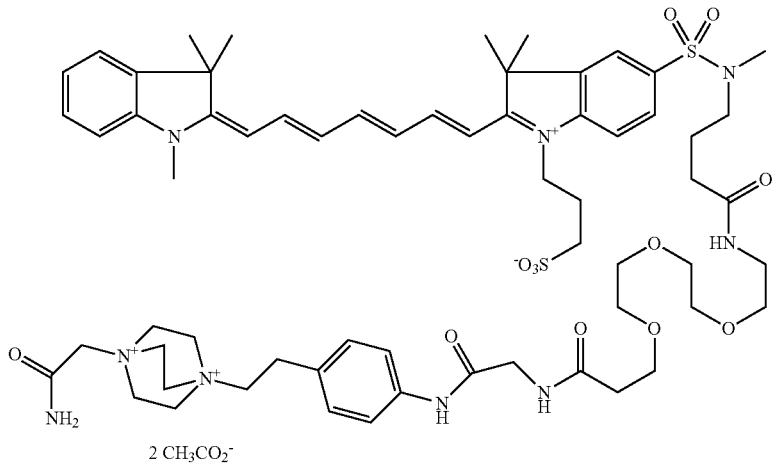

Compound A12 is prepared using Method 1. Fractions with >95% @ 750 nm are combined and dried to a solid.

Example 13

Bacterium Targeting Agents Bind to Bacteria In Vitro

This example demonstrates that the bacterium targeting agents described herein bind to various species of bacteria in vitro. Bacteria were grown at 37° C. to an $OD_{600}$=0.3-0.5 and centrifuged at 3500 rpm for 4 minutes before the subsequent pellets were re-suspended in TES buffer. Bacteria with or without targeting agent were grown under the same conditions. Bacterial targeting agents, compound A7, were incubated with bacterial pellets at a concentration of 10 μM final in TES buffer at RT for 1 hour. Bacteria with agent were centrifuged, re-suspended in TES buffer and analyzed by Flow Cytometry, as seen in FIG. 1A.

Figure 1B:
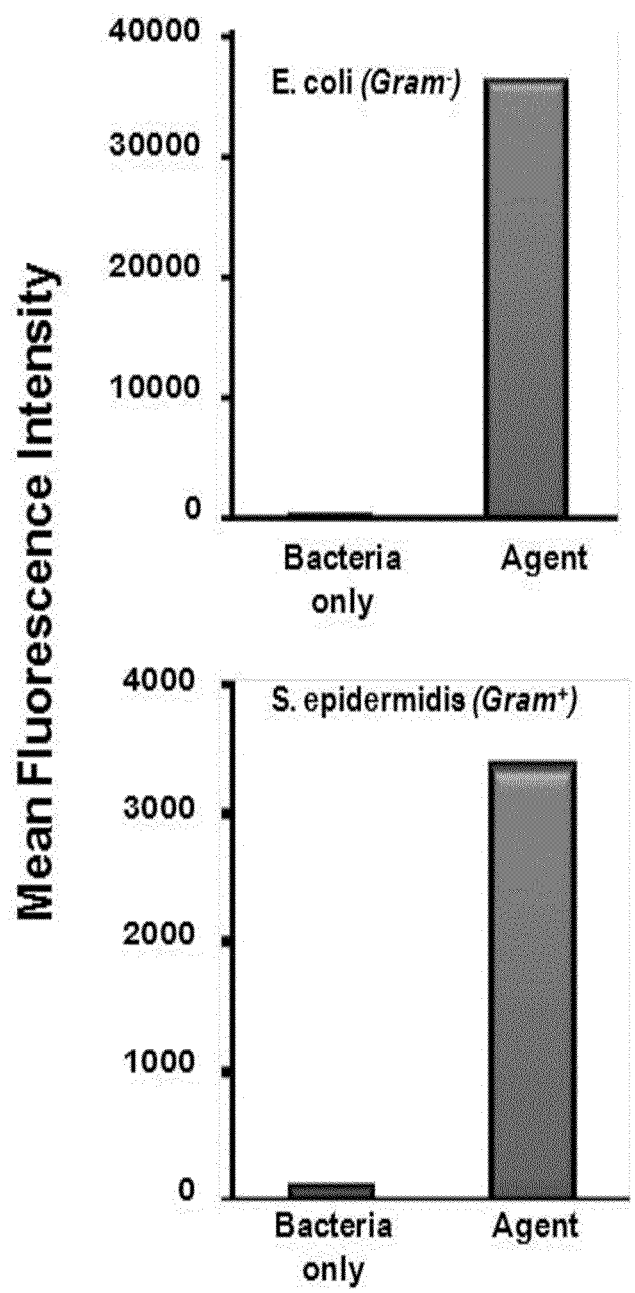
FIG. 1B is a histogram of fluorescence between bacteria unbound and bound by a bacterium targeting agent resulting from the flow cytometry depicted in FIG. 1A.

In this experiment, fluorescence is only associated with bacteria in the presence of the bacterium targeting agent described herein. FIG. 1B displays a histogram comparing mean fluorescence between bacteria alone and bacteria incubated with an exemplary bacteria targeting agent, compound A7. The results, shown in FIGS. 1A and 1B, demonstrate in vitro binding of bacterium targeting agents, such as compound A7, to both *Escherichia coli* and *Staphylococcus epidermidis*.

Example 14

Figure 2A:
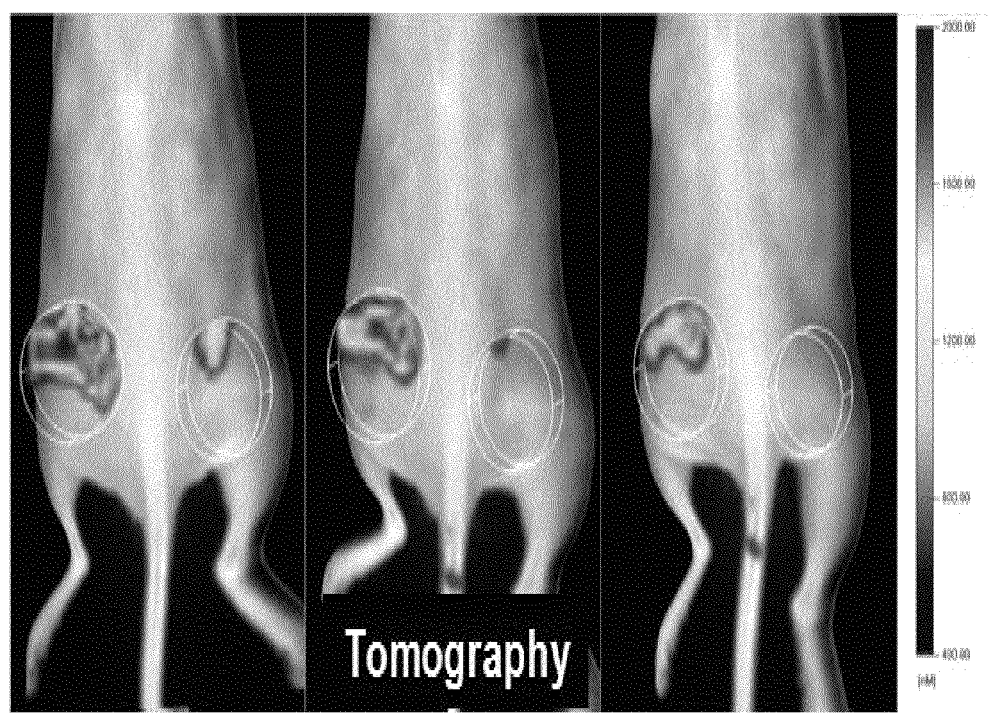
FIG. 2A depicts tomographic images of mice one, two, and three hours post-infection.
Figure 2B:
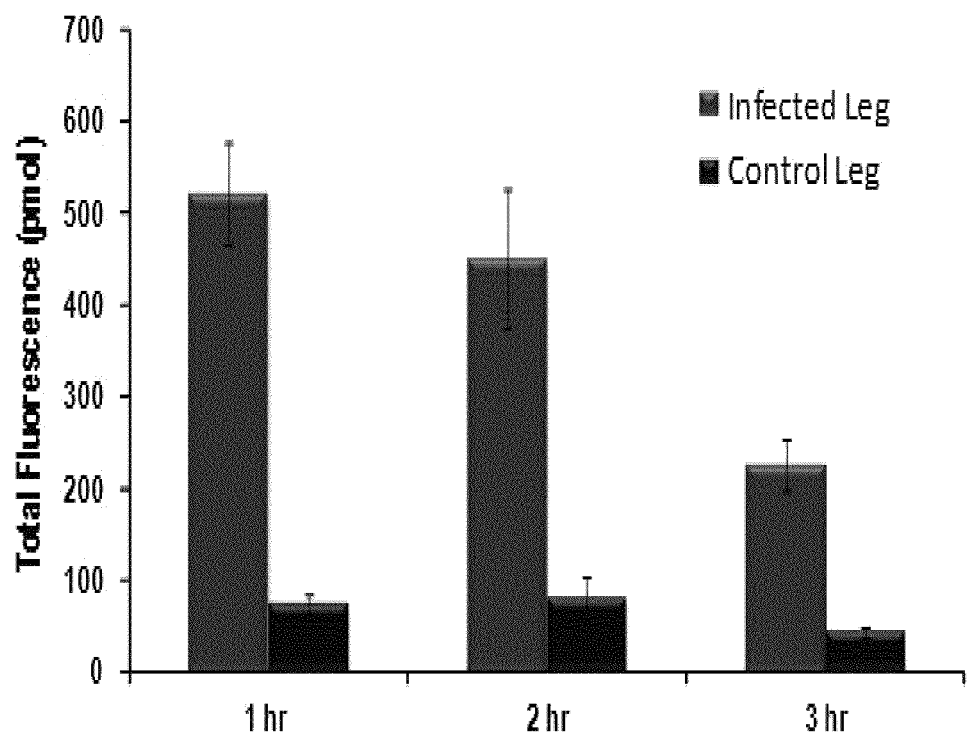
FIG. 2B is a histogram comparing fluorescence between infected and control (un-infected) legs of mice at one, two and three hours post-infection.

In Vivo Imaging of *Staphylococcus epidermidis* Using Bacterium Imaging Agents SKH1-E female mice, aged 6-8 weeks, were injected intramuscularly with $10^8$ CFUs (colony forming units) of *Staphylococcus epidermidis* in the left thigh. Mice were given intravenous injections of 5 nM of bacterium targeting agent, compound A7, approximately 24 hours after the initial bacterial inoculation. As seen in FIG. 2A, Mice were imaged on an FMT2500 (PerkinElmer, Inc., Waltham, Mass.), with emphasis on the thighs, at time points of one, two, and three hours following agent injection. Statistically significant differentiation between infected and uninfected areas was noted at all time points with an optimal imaging time at the one hour time point, depicted in FIG. 2B.

Example 15

In Vivo Imaging of *Escherichia coli* Using Bacterium Imaging Agents

Figure 3:
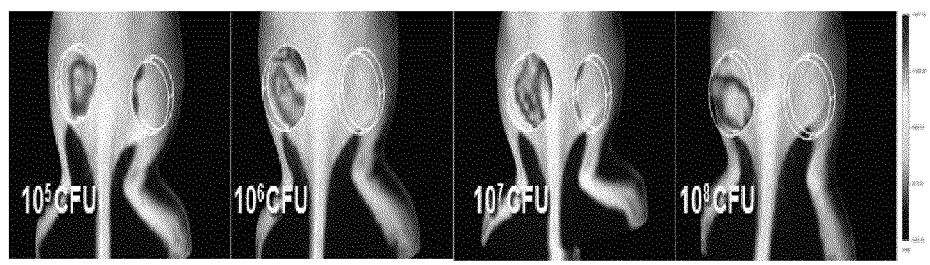
FIG. 3 depicts tomographic images for sites of E. coli bacterial infection in mice using a bacterium targeting agent (compound A7).

SKH1-E female mice, aged 6-8 weeks, were injected intramuscularly in the left thigh with different concentrations of *Escherichia coli* at $10^5$-$10^8$ CFUs. At approximately 24 hours after the initial bacterial inoculation, mice were given intravenous injections of 5 nM of bacterium targeting agent, compound A7. As seen in FIG. 3, one hour following agent injection, mice were imaged on the FMT2500 (PerkinElmer, Inc., Waltham, Mass.), with emphasis on the thigh. The images show clear uptake of the bacterial targeting agent at the site of the infection.

INCORPORATION BY REFERENCE

All publications, patents, and patent applications cited herein are hereby expressly incorporated by reference in their entirety and for all purposes to the same extent as if each was so individually denoted.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A bacterium targeting agent having an absorption and emission maximum between about 600 nm and about 900 nm, wherein the agent is represented by formula (I):

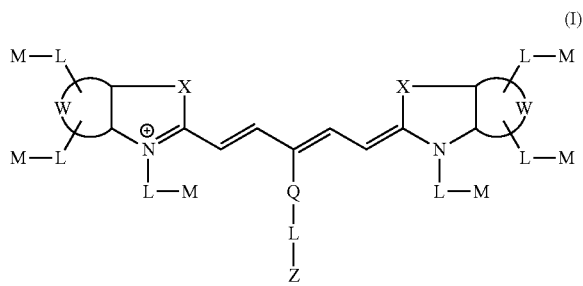

or a salt thereof, wherein:

Z is a bacterium targeting moiety comprising:
(a) a positively charged moiety having the formula:

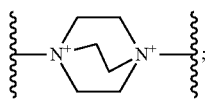

(b) an aliphatic, aromatic or heteroaromatic moiety, each of which is optionally substituted; and
(c) one or more anions as needed to provide a charge-neutral compound;

L is, independently for each occurrence, a linker moiety comprising a diradical of a moiety selected from the group consisting of glycine, alanine, β-alanine, —NH—$(CH_2)_n$—C(=O)— where n=1-8, 4-aminomethylbenzoic acid, cysteic acid, glutamic acid, amino-polyethylene glycol-carboxylic acid, amino-polyethylene glycol amine, ethylenediamine, propylenediamine, spermidine, spermine, hexanediamine, and a diamine-amino acid;

Q is selected from a group consisting of substituted or unsubstituted aryl, substituted or unsubstituted heteroaryl, $C_1$-$C_{18}$ alkyl, alkenyl, alkynyl, alkoxy, or thioalkyl group, or is absent;

W represents a benzo-condensed, a naphtho-condensed, or a pyrido-condensed ring;

X is, independently for each occurrence, selected from the group consisting of $C(CH_2Y_1)(CH_2Y_2)$, O, S, and Se;

$Y_1$ and $Y_2$ are independently selected from the group consisting of H and $C_1$-$C_{20}$ aliphatic group optionally substituted with L-M;

M, independently for each occurrence, is hydrogen or a chemical modifying moiety.

2. A bacterium targeting agent of formula (IV):

$$F-(L)_n-(Z)_m \quad (IV)$$

or a salt thereof, wherein:
n=1-8
m=1, 2, 3, or 4
F is a near infrared fluorochrome having an absorption and emission maximum between about 600 nm and about 900 nm;

L is a linker comprising a diradical of a moiety selected from the group consisting of glycine, alanine, β-alanine, —NH—$(CH_2)_n$—C(=O)— where n=1-8, 4-aminomethylbenzoic acid, cysteic acid, glutamic acid, amino-polyethylene glycol-carboxylic acid, amino-polyethylene glycol amine, ethylenediamine, propylenediamine, spermidine, spermine, hexanediamine, and a diamine-amino acid; and Z represents independently for each occurrence a bacterium targeting moiety comprising:
(a) a positively charged moiety having the formula:

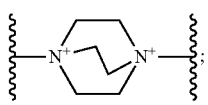

(b) an aliphatic, aromatic, heteroaromatic, or PEG moiety, each of which is optionally substituted; and
(c) one or more anions as needed to provide a charge-neutral compound.

3. The agent of claim 1, wherein M is selected from the group consisting of a hydrogen, alcohol, sulfonate, polysulfonate, cysteic acid, sulfonamide, sulfoxide, sulfone, carboxylate, ketone, phosphonate, phosphate; iminodiacetate, ethylenediamine tetraacetic acid, diethylenetriamine pentaacetic acid, tetraazacyclododecane tetraacetic acid, an amino acid, polyamino acid, oligo ethylene glycol, polyethylene glycol, amine, quaternary ammonium ion, sugar, glucosamine, galactosamine, mannosamine, polyethylene glycol (PEG), alkoxy polyethylene glycol, branched polypropylene glycol, polypropylene glycol, a graft copolymer of poly-lysine and methoxypolyethyleneglycol, peptide, lipid, fatty acid, palmitate, phospholipid, phospholipid-PEG conjugate, carbohydrate, iron oxide nanoparticle, naphthylalanine, phenylalanine, 3,3-diphenylpropylamine, taurine, phosphonate, phosphate, carboxylate and polycarboxylate.

4. The agent of 1, wherein the chemical modifier(s) M reduce the nonspecific cell membrane permeability of the agent.

5. One of the following agents or a salt thereof:

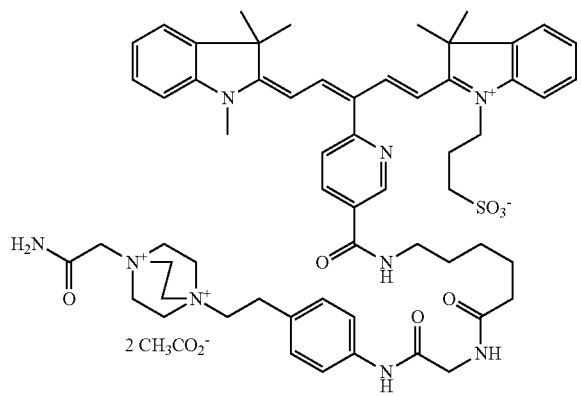

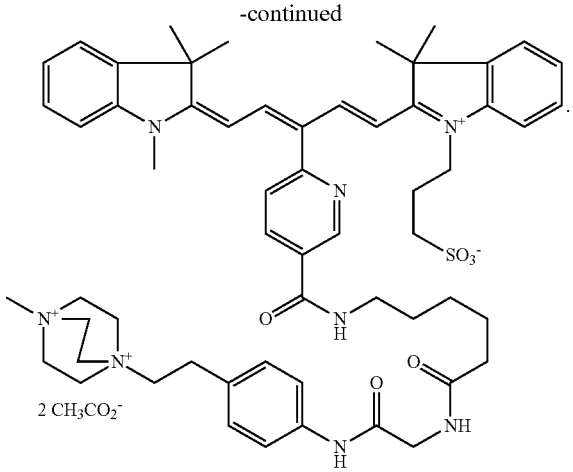

6. A pharmaceutical composition suitable for administration to a subject, comprising an agent of claim 1 and a pharmaceutically acceptable excipient.

7. A method of imaging bacterium infection in a subject, comprising:
   (a) administering an agent of claim 1 to a subject;
   (b) detecting the presence of the agent; and
   (c) producing an image representative of bacterium infection, thereby imaging bacterium infection.

8. The agent of claim 1, wherein the bacterium targeting agent has an affinity for bacterial cell surfaces; and wherein the bacterium targeting agent's affinity for bacterial cell surfaces is greater than the bacterium targeting agent's affinity for healthy mammalian cell surfaces.

9. The agent of claim 2, wherein the bacterium targeting agent has an affinity for bacterial cell surfaces; and wherein the bacterium targeting agent's affinity for bacterial cell surfaces is greater than the bacterium targeting agent's affinity for healthy mammalian cell surfaces.

10. A bacterium targeting agent that is a compound represented by Formula VII:

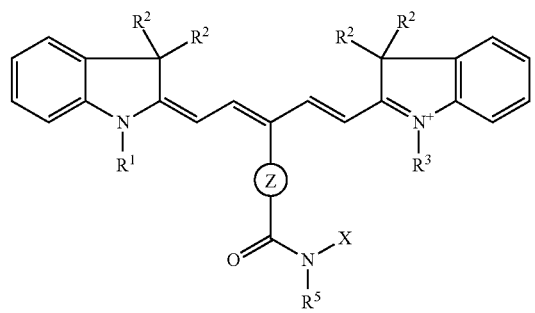

or a salt thereof, wherein:

X is one of the following:
   (a) —($C_1$-$C_6$ alkylene)-C(O)N($R^5$)—Y-(substituted heterocyclyl containing one quaternary ring nitrogen atom)-A;
   (b) —($C_1$-$C_6$ alkylene)-C(O)N($R^5$)—Y-(substituted heterocyclyl containing two quaternary ring nitrogen atoms)-(A)$_2$; or (c)

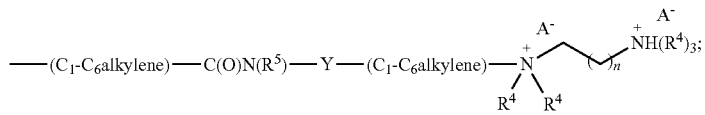

n is 1, 2, 3, or 4;
A is a monvalent anion or absent;
Y is one of the following:
   (a) ψ-alkylene-C(O)N($R^5$)-arylene-alkylene-; or
   (b) ψ-heteroalkylene-C(O)N($R^5$)-alkylene-C(O)N($R^5$)-arylene-alkylene-;
ψ is a bond to the amide nitrogen atom;
Z is

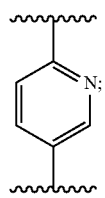 [SMILES: *c1ccc(*)nc1]

$R^1$ and $R^3$ each represent independently alkyl or alkylene-$SO_3^-$ $M^+$;
$R^2$ and $R^4$ each represent independently for each occurrence methyl, ethyl, or propyl;
$R^5$ represents independently for each occurrence hydrogen, methyl, ethyl, or propyl; and
M is a monovalent cation or absent.

11. The agent of claim 10, wherein X is —($C_1$-$C_6$ alkylene)-C(O)N($R^5$)—Y-(substituted heterocyclyl containing two quaternary ring nitrogen atoms)-(A)$_2$.

12. The agent of claim 10, wherein the substituted heterocyclyl containing two quaternary ring nitrogen atoms is one of the following:

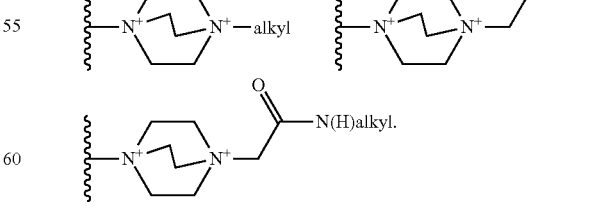

13. The agent of claim 10, wherein Y is ψ-$CH_2$—C(O)N(H)-phenyl-($C_1$-$C_4$)alkylene-.

14. The agent of claim 10, wherein Y is one of the following:

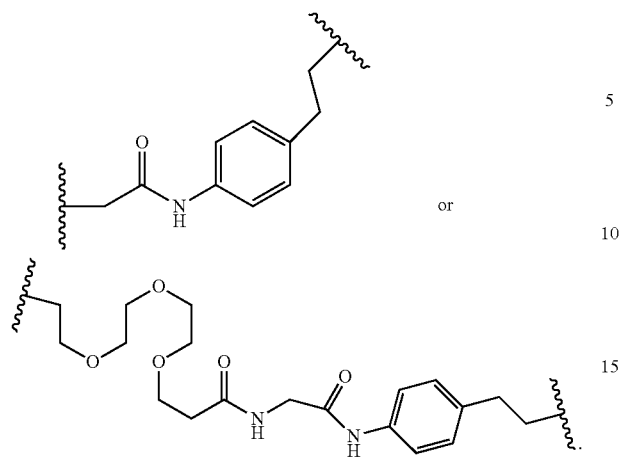

15. The agent of claim 10, wherein $R^1$ is alkyl.

16. The agent of claim 10, wherein $R^3$ is alkylene-$SO_3^-M^+$.

17. The agent of claim 1, wherein the diamine-amino acid is selected from the group consisting of homolysine, lysine, ornithine, diaminobutyric acid and diaminopropionic acid, succinic acid, glutaric acid, suberic acid, adipic acid, amide, triazole, urea and thiourea.

18. The agent of claim 2, wherein the diamine-amino acid is selected from the group consisting of homolysine, lysine, ornithine, diaminobutyric acid and diaminopropionic acid, succinic acid, glutaric acid, suberic acid, adipic acid, amide, triazole, urea and thiourea.

\* \* \* \* \*